United States Patent
Kajita et al.

(10) Patent No.: US 12,091,410 B2
(45) Date of Patent: Sep. 17, 2024

(54) HETEROCYCLIC COMPOUND

(71) Applicant: Takeda Pharmaceutical Company Limited, Osaka (JP)

(72) Inventors: Yuichi Kajita, Kanagawa (JP); Yuhei Miyanohana, Kanagawa (JP); Tatsuki Koike, Kanagawa (JP); Yasutaka Hoashi, Kanagawa (JP); Yasushi Hattori, Kanagawa (JP); Norihito Tokunaga, Kanagawa (JP); Tsuneo Oda, Kanagawa (JP); Tohru Miyazaki, Kanagawa (JP); Dilhumar Uyghur, Kanagawa (JP); Yoshiteru Ito, Kanagawa (JP); Kohei Takeuchi, Kanagawa (JP); Keisuke Imamura, Kanagawa (JP); Takahiro Sugimoto, Kanagawa (JP); Koichiro Fukuda, Kanagawa (JP); Yasuhisa Kohara, Kanagawa (JP); Rei Okamoto, Kanagawa (JP); Taiichi Ohra, Kanagawa (JP); Naoki Miyamoto, Kanagawa (JP); Yoshito Terao, Kanagawa (JP); Masanori Kawasaki, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 742 days.

(21) Appl. No.: 17/413,473

(22) PCT Filed: Dec. 11, 2019

(86) PCT No.: PCT/JP2019/048385
§ 371 (c)(1),
(2) Date: Jun. 11, 2021

(87) PCT Pub. No.: WO2020/122093
PCT Pub. Date: Jun. 18, 2020

(65) Prior Publication Data
US 2022/0017514 A1  Jan. 20, 2022

(30) Foreign Application Priority Data

Dec. 12, 2018  (JP) ................. 2018-232993

(51) Int. Cl.
| | | |
|---|---|---|
| *C07D 471/04* | (2006.01) | |
| *C07D 215/38* | (2006.01) | |
| *C07D 231/56* | (2006.01) | |
| *C07D 277/64* | (2006.01) | |
| *C07D 401/14* | (2006.01) | |

(52) U.S. Cl.
CPC ......... *C07D 471/04* (2013.01); *C07D 215/38* (2013.01); *C07D 231/56* (2013.01); *C07D 277/64* (2013.01); *C07D 401/14* (2013.01)

(58) Field of Classification Search
CPC .. C07D 471/04; C07D 215/38; C07D 231/56; C07D 277/64; C07D 401/14
See application file for complete search history.

(56) References Cited

U.S. PATENT DOCUMENTS

| 9,527,807 B2 | 12/2016 | Fukumoto et al. |
| 10,287,305 B2 | 5/2019 | Fujimoto et al. |
| 10,351,522 B2 | 7/2019 | Nagase et al. |
| 10,428,023 B2 | 10/2019 | Kajita et al. |
| 2010/0150840 A1 | 6/2010 | Yanagisawa |
| 2016/0250224 A1 | 9/2016 | Wan |
| 2016/0271214 A1 | 9/2016 | Ashley et al. |
| 2017/0226103 A1 | 8/2017 | Kamenecka et al. |
| 2017/0226137 A1* | 8/2017 | Fujimoto ............. C07D 417/14 |

(Continued)

FOREIGN PATENT DOCUMENTS

| EP | 0 893 498 A2 | 1/1999 |
| EP | 3 029 024 A1 | 6/2016 |

(Continued)

OTHER PUBLICATIONS

Boss et al., "Orexin research: patent news from 2016," Expert Opinion on Therapeutic Patents, 2017, 27(10):1123-1133.

(Continued)

*Primary Examiner* — Matthew P Coughlin
*Assistant Examiner* — Ashli Ariana Chicks
(74) *Attorney, Agent, or Firm* — Sterne, Kessler, Goldstein & Fox P.L.L.C.

(57) ABSTRACT

The present invention provides a heterocyclic compound having an orexin type 2 receptor agonist activity.
A compound represented by the formula (I):

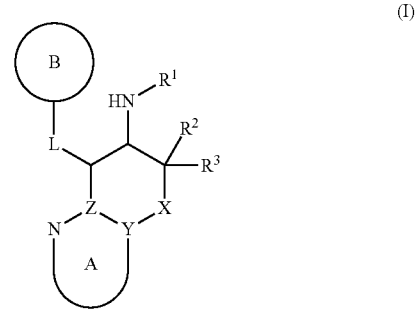

wherein each symbol is as described in the description, or a salt thereof has an orexin type 2 receptor agonist activity, and is useful as an agent for the prophylaxis or treatment of narcolepsy.

13 Claims, No Drawings

(56) References Cited

U.S. PATENT DOCUMENTS

| | | |
|---|---|---|
| 2018/0179151 A1 | 6/2018 | Nagase et al. |
| 2019/0031611 A1 | 1/2019 | Fujimoto et al. |
| 2019/0263843 A1 | 8/2019 | Fujimoto et al. |
| 2020/0255403 A1 | 8/2020 | Bogen et al. |

FOREIGN PATENT DOCUMENTS

| | | |
|---|---|---|
| WO | WO-01/08720 A2 | 2/2001 |
| WO | WO-01/74162 A1 | 10/2001 |
| WO | WO-2004/040000 A2 | 5/2004 |
| WO | WO-2004/054510 A2 | 7/2004 |
| WO | WO-2009/049215 A1 | 4/2009 |
| WO | WO-2012/137982 A2 | 10/2012 |
| WO | WO-2014/170343 A1 | 10/2014 |
| WO | WO-2014/198880 A1 | 12/2014 |
| WO | WO-2015/048091 A1 | 4/2015 |
| WO | WO-2015/073707 A1 | 5/2015 |
| WO | WO-2015/147240 A1 | 10/2015 |
| WO | WO-2016/025669 A1 | 2/2016 |
| WO | WO-2016/199906 A1 | 12/2016 |
| WO | WO-2017/135306 A1 | 8/2017 |
| WO | WO-2018/164191 A1 | 9/2018 |
| WO | WO-2018/164192 A1 | 9/2018 |
| WO | WO-2019/027003 A1 | 2/2019 |
| WO | WO-2019/027058 A1 | 2/2019 |
| WO | WO-2019/112007 A1 | 6/2019 |
| WO | WO-2020/004536 A1 | 1/2020 |
| WO | WO-2020/004537 A1 | 1/2020 |
| WO | WO-2020/122093 A1 | 6/2020 |
| WO | WO-2020/167701 A1 | 8/2020 |
| WO | WO-2020/167706 A1 | 8/2020 |

OTHER PUBLICATIONS

Busquets et al., "Decreased Plasma Levels of Orexin-A in Sleep Apnea," Respiration, 2004, 71:575-579.
Chemelli et al., "Narcolepsy in orexin Knockout Mice: Molecular Genetics of Sleep Regulation," Cell, Aug. 20, 1999, 98:437-451.
Desseilles et al., "Neuroimaging Insights into the Pathophysiology of Sleep Disorders," Sleep, Jun. 1, 2008, 31(6):777-794.
Funato et al., "Enhanced Orexin Receptor-2 Signaling Prevents Diet-Induced Obesity and Improves Leptin Sensitivity," Cell Metabolism, Jan. 7, 2009, 9:64-76.
Jaeger et al., "Effects of orexin-A on memory processing," Peptides, 2002, 23:1683-1688.
Kushikata et al., "Orexinergic Neurons and Barbiturate Anesthesia," Neuroscience, 2003, 121:855-863.
Lin et al., "The Sleep Disorder Canine Narcolepsy is Caused by a Mutation in the Hypocretin (Orexin) Receptor 2 Gene," Cell, Aug. 6, 1999, 98:365-376.
Mieda et al., "Orexin (Hypocretin) Receptor Agonists and Antagonists for Treatment of Sleep Disorders," CNS Drugs, 2013, 27:83-90.
Mieda et al., "Orexin peptides prevent cataplexy and improve wakefulness in an orexin neuron-ablated model of narcolepsy in mice," PNAS, Mar. 30, 2004, 101(13):4649-4654.
Perez et al., "Systems Genomics Identifies a Key Role for Hypocretin/Orexin Receptor-2 in Human Heart Failure," Journal of the American College of Cardiology, 2015, 66(22):2522-2533.
Sakurai et al., "Orexins and Orexin Receptors: A Family of Hypothalamic Neuropeptides and G Protein-Coupled Receptors that Regulate Feeding Behavior," Cell, Feb. 20, 1998, 92:573-585.
Thannickal et al., "Hypocretin (orexin) cell loss in Parkinson's disease," Brain, 2007, 130:1586-1595.
Willie et al., "Distinct Narcolepsy Syndromes in Orexin Receptor-2 and Orexin Null Mice: Molecular Genetic Dissection of Non-REM and REM Sleep Regulatory Processes," Neuron, Jun. 5, 2003, 38:715-730.

* cited by examiner

HETEROCYCLIC COMPOUND

CROSS-REFERENCE TO RELATED APPLICATIONS

This application is the U.S. National Stage of PCT/JP2019/048385, filed Dec. 11, 2019, which claims priority to JP 2018-232993, filed Dec. 12, 2018.

TECHNICAL FIELD

The present invention relates to a heterocyclic compound, particularly, a heterocyclic compound having an orexin type 2 receptor agonist activity.

BACKGROUND OF THE INVENTION

Orexin is a neuropeptide specifically produced in particular neurons located sparsely in the lateral hypothalamus and its surrounding area, and consists of two subtypes, orexin A and orexin B. Both orexin A and orexin B are endogenous ligands of the orexin receptors, which are G protein-coupled receptors mainly present in the brain, and two types of subtypes, type 1 and type 2, are known for the orexin receptors (non-patent document 1).

Since orexin-producing neurons (orexin neurons) are localized in the vicinity of the feeding center, and intraventricular administration of orexin peptide results in an increase in food intake, orexin initially attracted attention as a neuropeptide having a feeding behavioral regulation. Thereafter, however, it was reported that the cause of dog narcolepsy is genetic variation of orexin type 2 receptor (non-patent document 2), and the role of orexin in controlling sleep and wakefulness has been also attracted.

From the studies using a transgenic mouse having denatured orexin neurons and a double transgenic mouse obtained by crossing this mouse with orexin overexpressing transgenic mouse, it was clarified that narcolepsy-like symptoms that appear by degeneration of orexin neurons disappear due to sustained expression of orexin. Similarly, when orexin peptide was intraventricularly administered to a transgenic mouse having denatured orexin neuron, improvement of narcolepsy-like symptoms was also observed (non-patent document 3). Studies of orexin type 2 receptor knockout mice have suggested that orexin type 2 receptor is important for maintaining arousal (non-patent document 4, non-patent document 5). Such background suggests that orexin type 2 receptor agonists become therapeutic drugs for narcolepsy or therapeutic drugs for other sleep disorders exhibiting excessive sleepiness (non-patent document 6).

In addition, it is suggested that a peptidic agonist that selectively acts on the orexin type 2 receptor improves obesity due to high fat diet load in mice (non-patent document 7).

In addition, it is suggested that intraventricular administration of orexin peptide shortens the systemic anesthetic time of rat (non-patent document 8).

In addition, it is suggested that patients with sleep apnea syndrome show low orexin A concentration levels in plasma (non-patent document 9).

In addition, it is suggested that intraventricular administration of orexin peptide improves memory retention of senescence-accelerated model mouse (SAMP8) with cognitive dysfunction (non-patent document 10).

In addition, it is suggested that Orexin type 2 receptor agonist will be a therapeutic drug for cardiac failure (patent document 1, non-patent document 11).

In addition, it is suggested that the daytime sleepiness of Parkinson's disease patients is caused by orexin nerve fallout (non-patent document 12).

In addition, it is suggested that orexin regulates bone formation and bone loss, and orexin type 2 receptor agonist will be a therapeutic drug for diseases related to bone loss such as osteoporosis, rheumatoid arthritis and the like (patent document 2).

In addition, it is suggested that orexin receptor agonist is useful for the prophylaxis or treatment of sepsis, severe sepsis and septic shock, since the mortality was significantly improved by mere continuous administration of orexin from the periphery in septic shock model mouse (patent document 3).

Therefore, a compound having an orexin type 2 receptor agonist activity is expected to be useful as a novel therapeutic drug for narcolepsy, idiopathic hypersomnia, hypersomnia, sleep apnea syndrome, disturbance of consciousness such as coma and the like, narcolepsy syndrome accompanied by narcolepsy-like symptoms, hypersomnia syndrome accompanied by daytime hypersomnia (e.g., Parkinson's disease, Guillain-Barre syndrome and Kleine Levin syndrome), Alzheimer, obesity, insulin resistance syndrome, cardiac failure, diseases related to bone loss, sepsis and the like, further, anesthetic antagonist, a prophylactic or therapeutic drug for side effects and complications due to anesthesia.

As sulfonamide derivatives, a compound represented by the formula

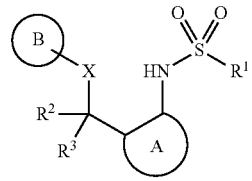

wherein each symbol is as described in the document (Patent Document 4) has been reported.

In addition, as compounds having an orexin type 2 receptor agonist activity, the following compounds have been reported.

A compound represented by the formula

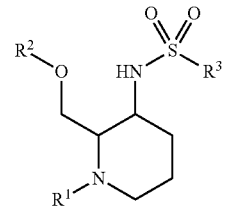

wherein each symbol is as described in the document (Patent Document 5).

A compound represented by the formula

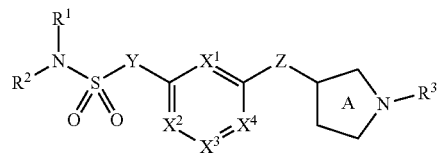

wherein each symbol is as described in the document (Patent Document 6).

A compound represented by the formula

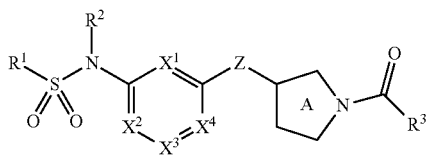

wherein each symbol is as described in the document (Patent Document 7).

A compound represented by the formula

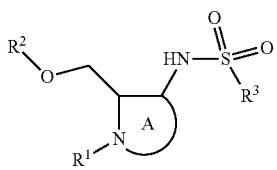

wherein each symbol is as described in the document (Patent Document 8).

A compound represented by the formula

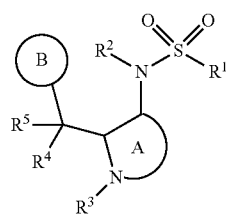

wherein each symbol is as described in the document (Patent Document 9).

However, it is considered that these compounds are not satisfactory in terms of activity, pharmacokinetics or safety, and therefore, development of a compound having an orexin type 2 receptor agonist activity is still desired.

DOCUMENT LIST

Patent Document

Patent Document 1: WO 2015/073707 A1
Patent Document 2: WO 2015/048091 A1
Patent Document 3: WO 2015/147240 A1
Patent Document 4: WO 2012/137982 A9
Patent Document 5: WO 2017/135306 A1
Patent Document 6: WO 2018/164191 A1
Patent Document 7: WO 2018/164192 A1
Patent Document 8: WO 2019/027003 A1
Patent Document 9: WO 2019/027058 A1

Non-Patent Document

Non-Patent Document 1: Cell, Vol. 92, 573-585, 1998
Non-Patent Document 2: Cell, Vol. 98, 365-376, 1999
Non-Patent Document 3: Proc. Natl. Acad. Sci. USA, Vol. 101, 4649-4654, 2004
Non-Patent Document 4: Cell, Vol. 98, 437-451, 1999
Non-Patent Document 5: Neuron, Vol. 38, 715-730, 2003
Non-Patent Document 6: CNS Drugs, Vol. 27, 83-90, 2013
Non-Patent Document 7: Cell Metabolism, Vol. 9, 64-76, 2009
Non-Patent Document 8: Neuroscience, Vol. 121, 855-863, 2003
Non-Patent Document 9: Respiration, Vol. 71, 575-579, 2004
Non-Patent Document 10: Peptides, Vol. 23, 1683-1688, 2002
Non-Patent Document 11: Journal of the American College of Cardiology. Vol. 66, 2015, Pages 2522-2533
[Non-Patent Document 12: Brain. Vol. 130, 2007, Pages 1586-1595

SUMMARY OF THE INVENTION

Problems to be Solved by the Invention

The present invention aims to provide a heterocyclic compound having an orexin type 2 receptor agonist activity.

Means of Solving the Problems

The present inventors have found that a compound represented by the following formula (I) or a salt thereof (sometimes to be referred to as compound (I) in the present specification) has an orexin type 2 receptor agonist activity. As a result of further studies, they have completed the present invention.

Accordingly, the present invention relates to the followings.

[1] A compound represented by the formula:

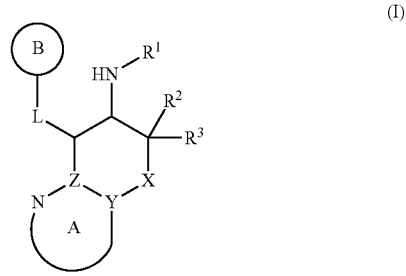

wherein
$R^1$ is an optionally substituted $C_{1-6}$ alkylsulfonyl group, an optionally substituted mono- or di-$C_{1-6}$ alkylaminosulfonyl group, an optionally substituted 3- to 6-membered cyclylsulfonyl group, a formylcarbonyl group, a carboxycarbonyl group, a carbamoylcarbonyl group, an optionally substituted $C_{1-6}$ alkyl-carbonyl group, an optionally substituted $C_{1-6}$ alkoxy-carbonyl group, an optionally substituted mono- or di-$C_{1-6}$ alkyl-carbamoyl group, an optionally substituted $C_{1-6}$ alkyl-carbonyl-carbonyl group, an optionally substituted $C_{1-6}$ alkoxy-carbonyl-carbonyl group, an optionally substituted mono- or di-$C_{1-6}$ alkyl-carbamoyl-carbonyl group or an optionally substituted 3- to 6-membered cyclyl-carbonyl group;
$R^2$ and $R^3$ are each independently a hydrogen atom, an optionally substituted $C_{1-6}$ alkyl group or a halogen atom;

X is an optionally substituted methylene group or an oxygen atom;

Y and Z are each independently a carbon atom or a nitrogen atom;

Ring A is an optionally substituted 5- or 6-membered nitrogen-containing aromatic heterocycle;

L is an optionally substituted methylene group, an oxygen atom, —O-$L^1$-, -$L^1$-O— or -$L^1$-$L^2$-;

$L^1$ and $L^2$ are each independently an optionally substituted methylene group; and Ring B is an optionally further substituted 4- to 7-membered ring, or a salt thereof.

[2] The compound or salt according to the above-mentioned [1], wherein $R^1$ is,
(1) a $C_{1-6}$ alkylsulfonyl group,
(2) a mono- or di-$C_{1-6}$ alkyl-carbamoyl-carbonyl group, or
(3) a 3- to 6-membered non-aromatic heterocyclylcarbonyl group;

$R^2$ and $R^3$ are both hydrogen atoms;

X is a methylene group;

Y and Z are each independently a carbon atom or a nitrogen atom;

Ring A is a 5- or 6-membered aromatic heterocycle optionally substituted by 1 to 3 substituents selected from
  (a) a halogen atom,
  (b) a cyano group,
  (c) a $C_{1-6}$ alkyl group optionally substituted by 1 to 3 hydroxy groups, and
  (d) a mono- or di-$C_{1-6}$ alkyl-carbamoyl group;

L is a methylene group or —O—$CH_2$—; and

Ring B is a 6-membered ring further substituted by 1 to 3 substituents selected from
  (a) a $C_{6-14}$ aryl group optionally substituted by 1 to 3 substituents selected from
    (i) a halogen atom, and
    (ii) a $C_{1-6}$ alkyl group, and
  (b) a 5- or 6-membered monocyclic aromatic heterocyclic group or a 8- to 14-membered fused polycyclic aromatic heterocyclic group, each optionally substituted 1 to 3 substituents selected from
    (i) a halogen atom,
    (ii) a $C_{1-6}$ alkyl group, and
    (iii) a $C_{1-6}$ alkoxy group.

[3] The compound or salt according to the above-mentioned [1], wherein $R^1$ is,
(1) a $C_{1-6}$ alkylsulfonyl group,
(2) a mono- or di-$C_{1-6}$ alkyl-carbamoyl-carbonyl group, or
(3) a tetrahydrofurylcarbonyl group;

$R^2$ and $R^3$ are both hydrogen atoms;

X is a methylene group;

Y and Z are each independently a carbon atom or a nitrogen atom;

Ring A is
(1) a pyrazole ring optionally substituted by 1 to 3 substituents selected from
  (a) a halogen atom,
  (b) a cyano group,
  (c) a $C_{1-6}$ alkyl group optionally substituted by 1 to 3 hydroxy groups, and
  (d) a mono- or di-$C_{1-6}$ alkyl-carbamoyl group, (2) a triazole ring optionally substituted by 1 to 3 $C_{1-6}$ alkyl groups,
(3) an imidazole ring optionally substituted by 1 to 3 $C_{1-6}$ alkyl groups,
(4) a thiazole ring optionally substituted by 1 to 3 $C_{1-6}$ alkyl groups, or
(5) a pyridine ring optionally substituted by 1 to 3 $C_1$-6 alkyl groups;

L is a methylene group or —O—$CH_2$—; and

Ring B is
(1) a cyclohexane ring further substituted by 1 to 3 $C_{6-14}$ aryl groups,
(2) a piperidine ring further substituted by 1 to 3 substituents selected from
  (a) a $C_{6-14}$ aryl group optionally substituted by 1 to 3 halogen atoms, and
  (b) a pyridyl group, a pyrimidinyl group or a quinazolinyl group, each optionally substituted 1 to 3 substituents selected from
    (i) a halogen atom,
    (ii) a $C_{1-6}$ alkyl group, and
    (iii) a $C_{1-6}$ alkoxy group,
(3) a benzene ring further substituted by 1 to 3 substituents selected from
  (a) a $C_{6-14}$ aryl group optionally substituted by 1 to 3 substituents selected from
    (i) a halogen atom, and
    (ii) a $C_{1-6}$ alkyl group, and
  (b) a pyridyl group optionally substituted by 1 to 3 $C_1$-6 alkyl groups, or
(4) a pyridine ring further substituted by 1 to 3 $C_{6-14}$ aryl groups optionally substituted by 1 to 3 halogen atoms.

[4] The compound or salt according to the above-mentioned [1], wherein $R^1$ is a $C_1$-6 alkylsulfonyl group;

$R^2$ and $R^3$ are both hydrogen atoms;

X is a methylene group;

Y and Z are each independently a carbon atom or a nitrogen atom;

Ring A is a pyrazole ring optionally substituted by 1 to 3 $C_{1-6}$ alkyl groups;

L is —O—$CH_2$—; and

Ring B is a piperidine ring further substituted by 1 to 3 pyrimidinyl groups optionally substituted by 1 to 3 halogen atoms.

[5] N-[7-({[1-(5-Fluoropyrimidin-2-yl)piperidin-4-yl]oxy}methyl)-2-(propan-2-yl)-4,5,6,7-tetrahydropyrazolo[1,5-a]pyridin-6-yl]methanesulfonamide or a salt thereof.

[6] N-[2-Ethyl-7-({[1-(5-fluoropyrimidin-2-yl)piperidin-4-yl]oxy}methyl)-4,5,6,7-tetrahydropyrazolo[1,5-a]pyridin-6-yl]methanesulfonamide or a salt thereof.

[7] N-[2-(Propan-2-yl)-7-({[1-(pyrimidin-2-yl)piperidin-4-yl]oxy}methyl)-4,5,6,7-tetrahydropyrazolo[1,5-a]pyridin-6-yl]methanesulfonamide or a salt thereof.

[8] A medicament comprising the compound or salt according to the above-mentioned [1].

[9] The medicament according to the above-mentioned [8], which is an orexin type 2 receptor agonist.

[10] The medicament according to the above-mentioned [8], which is an agent for the prophylaxis or treatment of narcolepsy.

[11] The compound or salt according to the above-mentioned [1] for use in the prophylaxis or treatment of narcolepsy.

[12] A method for activating an orexin type 2 receptor in a mammal, which comprises administering an effective amount of the compound or salt according to the above-mentioned [1] to the mammal.

[13] A method for preventing or treating narcolepsy in a mammal, which comprises administering an effective amount of the compound or salt according to the above-mentioned [1] to the mammal.

[14] Use of the compound or salt according to the above-mentioned [1] for the manufacture of an agent for the prophylaxis or treatment of narcolepsy.

Effect of the Invention

The compound of the present invention has an orexin type 2 receptor agonist activity, and is useful as an agent for the prophylaxis or treatment of narcolepsy.

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ arylcarbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent Group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl)($C_{1-6}$ alkyl-carbonyl) amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),

(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi- or tri-cyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi- or tri-cyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent Group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxycarbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent Group A".

Preferable examples of the optionally substituted amino group include an amino group, a mono- or di-(optionally halogenated $C_{1-6}$ alkyl) amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl) amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) amino group (e.g., N-acetyl-N-methylamino) and a ($C_{1-6}$ alkyl) ($C_{6-14}$ aryl-carbonyl) amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ arylcarbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxy group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent Group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent Group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., alkylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent Group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi- or tri-cyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and 9- to 14-membered fused polycyclic (preferably bi- or tri-cyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a heterocycle containing at least one nitrogen atom as a ring-constituting atom, from among the "heterocycle".

In the present specification, examples of the "5- or 6-membered nitrogen-containing aromatic heterocycle" include 5- to 6-membered groups containing at least nitrogen atom as ring constituting atom, from among the "5- or 6-membered monocyclic aromatic heterocycle".

In the present specification, examples of the "4- to 7-membered ring" include a 04-7 cycloalkane, benzene, a 5- or 6-membered monocyclic aromatic heterocycle and a 4- to 7-membered monocyclic non-aromatic heterocycle.

In the present specification, examples of the "04-7 cycloalkane" include 4- to 7-membered groups from among the "$C_{3-10}$ cycloalkane".

In the present specification, examples of the "4- to 7-membered monocyclic non-aromatic heterocycle" include 4- to 7-membered groups from among the "3- to 8-membered monocyclic non-aromatic heterocycle".

In the present specification, examples of the "3- to 6-membered cyclic group" include a 03-6 cycloalkyl group, phenyl, a 5- or 6-membered monocyclic aromatic heterocyclic group and a 3- to 6-membered monocyclic non-aromatic heterocyclic group.

In the present specification, examples of the "$C_{3-6}$ cycloalkyl group" include 3- to 6-membered groups from among the "$C_{3-10}$ cycloalkyl group".

In the present specification, examples of the "3- to 6-membered monocyclic non-aromatic heterocyclic group" include 3- to 6-membered groups from among the "3- to 8-membered monocyclic non-aromatic heterocyclic group".

In the present specification, the "mono- or di-$C_{1-6}$ alkylaminosulfonyl group" means a sulfonyl group to which the "mono- or di-$C_{1-6}$ alkylamino group" is bonded.

In the present specification, the "3- to 6-membered cyclylsulfonyl group" means a sulfonyl group to which the "3- to 6-membered cyclic group" is bonded.

In the present specification, the "$C_{1-6}$ alkyl-carbonyl-carbonyl group" means a carbonyl group to which the "$C_{1-6}$ alkyl-carbonyl group" is bonded.

In the present specification, the "$C_{1-6}$ alkoxy-carbonyl-carbonyl group" means a carbonyl group to which the "$C_{1-6}$ alkoxy-carbonyl group" is bonded.

In the present specification, the "mono- or di-$C_{1-6}$ alkyl-carbamoyl-carbonyl group" means a carbonyl group to which the "mono- or di-$C_{1-6}$ alkyl-carbonyl group" is bonded.

In the present specification, the "3- to 6-membered cyclyl-carbonyl group" means a carbonyl group to which the "3- to 6-membered cyclic group" is bonded.

The definition of each symbol used in the formula (I) is explained in detail.

$R^1$ is an optionally substituted $C_{1-6}$ alkylsulfonyl group, an optionally substituted mono- or di-$C_{1-6}$ alkylaminosulfonyl group, an optionally substituted 3- to 6-membered cyclylsulfonyl group, a formylcarbonyl group, a carboxycarbonyl group, a carbamoylcarbonyl group, an optionally substituted $C_{1-6}$ alkyl-carbonyl group, an optionally substituted $C_{1-6}$ alkoxy-carbonyl group, an optionally substituted mono- or di-$C_{1-6}$ alkyl-carbamoyl group, an optionally substituted $C_{1-6}$ alkyl-carbonyl-carbonyl group, an optionally substituted $C_{1-6}$ alkoxy-carbonyl-carbonyl group, an optionally substituted mono- or di-$C_{1-6}$ alkyl-carbamoyl-carbonyl group or an optionally substituted 3- to 6-membered cyclyl-carbonyl group.

Examples of the substituent of the above-mentioned "optionally substituted $C_{1-6}$ alkylsulfonyl group", "optionally substituted mono- or di-$C_{1-6}$ alkylaminosulfonyl group", "optionally substituted 3- to 6-membered cyclylsulfonyl group", "optionally substituted $C_{1-6}$ alkyl-carbonyl group", "optionally substituted $C_{1-6}$ alkoxy-carbonyl group", "optionally substituted mono- or di-$C_{1-6}$ alkyl-carbamoyl group", "optionally substituted $C_{1-6}$ alkyl-carbonyl-carbonyl group", "optionally substituted $C_{1-6}$ alkoxy-carbonyl-carbonyl group", "optionally substituted mono- or di-$C_{1-6}$ alkyl-carbamoyl-carbonyl group" and "optionally substituted 3- to 6-membered cyclylcarbonyl group" include substituents selected from Substituent Group A. The number of the substituents is preferably 1 to 3. When the number of the substituents is 2 or more, the respective substituents may be the same or different.

$R^1$ is preferably
(1) an optionally substituted $C_{1-6}$ alkylsulfonyl group,
(2) an optionally substituted mono- or di-$C_{1-6}$ alkyl-carbamoyl-carbonyl group, or
(3) an optionally substituted 3- to 6-membered cyclylcarbonyl group (preferably a 3- to 6-membered non-aromatic heterocyclylcarbonyl group).

$R^1$ is more preferably
(1) a $C_{1-6}$ alkylsulfonyl group (e.g., methylsulfonyl, ethylsulfonyl),
(2) a mono- or di-$C_{1-6}$ alkyl-carbamoyl-carbonyl group (e.g., dimethylcarbamoylcarbonyl), or
(3) a 3- to 6-membered non-aromatic heterocyclylcarbonyl group (e.g., tetrahydrofurylcarbonyl).

$R^1$ is particularly preferably a $C_{1-6}$ alkylsulfonyl group (e.g., methylsulfonyl).

$R^2$ and $R^3$ are each independently a hydrogen atom, an optionally substituted $C_{1-6}$ alkyl group or a halogen atom.

Examples of the substituent of the "optionally substituted $C_{1-6}$ alkyl group" for $R^2$ or $R^3$ include substituents selected from Substituent Group A. The number of the substituents is preferably 1 to 3. When the number of the substituents is 2 or more, the respective substituents may be the same or different.

$R^2$ and $R^3$ are preferably both hydrogen atoms.

X is an optionally substituted methylene group or an oxygen atom.

Examples of the substituent of the "optionally substituted methylene group" for X include substituents selected from Substituent Group A. The number of the substituents is preferably 1 to 3. When the number of the substituents is 2 or more, the respective substituents may be the same or different.

X is preferably an optionally substituted methylene group.

X is particularly preferably a methylene group.

Y and Z are each independently a carbon atom or a nitrogen atom.

Ring A is an optionally substituted 5- or 6-membered nitrogen-containing aromatic heterocycle.

The "optionally substituted 5- or 6-membered nitrogen-containing aromatic heterocycle" for Ring A optionally has substituent(s). Example of the substituent include the above-mentioned "substituent". The number of the substituents is preferably 1 to 3. When the number of the substituents is 2 or more, the respective substituents may be the same or different.

Ring A is preferably a 5- or 6-membered aromatic heterocycle (e.g., pyrazole, triazole (e.g., 1,2,3-triazole, 1,2,4-triazole), imidazole, thiazole, pyridine) optionally substituted by 1 to 3 substituents selected from
(a) a halogen atom (e.g., a chlorine atom, a bromine atom),
(b) a cyano group,
(c) a $C_{1-6}$ alkyl group (e.g., methyl, ethyl, isopropyl) optionally substituted by 1 to 3 hydroxy groups, and
(d) a mono- or di-$C_{1-6}$ alkyl-carbamoyl group (e.g., dimethylcarbamoyl).

Ring A is more preferably
(1) a pyrazole ring optionally substituted by 1 to 3 substituents selected from
  (a) a halogen atom (e.g., a chlorine atom, a bromine atom),
  (b) a cyano group,
  (c) a $C_{1-6}$ alkyl group (e.g., methyl, ethyl, isopropyl) optionally substituted by 1 to 3 hydroxy groups, and
  (d) a mono- or di-$C_{1-6}$ alkyl-carbamoyl group (e.g., dimethylcarbamoyl),
(2) a triazole ring (e.g., 1,2,3-triazole, 1,2,4-triazole) optionally substituted by 1 to 3 $C_{1-6}$ alkyl groups (e.g., methyl, ethyl, isopropyl),
(3) an imidazole ring optionally substituted by 1 to 3 $C_{1-6}$ alkyl groups (e.g., methyl),
(4) a thiazole ring optionally substituted by 1 to 3 $C_{1-6}$ alkyl groups (e.g., methyl), or
(5) a pyridine ring optionally substituted by 1 to 3 $C_{1-6}$ alkyl groups (e.g., methyl).

Ring A is further more preferably a pyrazole ring optionally substituted by 1 to 3 $C_{1-6}$ alkyl groups (e.g., ethyl, isopropyl).

Ring A is particularly preferably a pyrazole ring substituted by one $C_{1-6}$ alkyl group (e.g., ethyl, isopropyl).

The ring structure for Ring A represented by

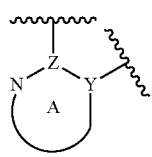

is preferably the following ring structures (a) to (g).

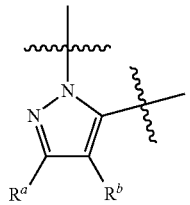
(a)

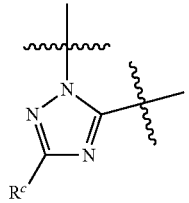
(b)

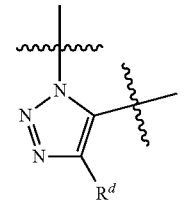
(c)

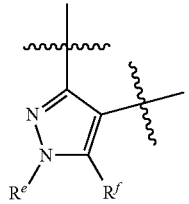
(d)

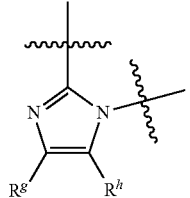
(e)

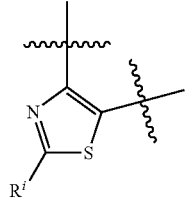
(f)

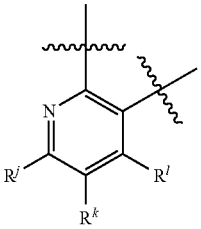
(g)

wherein $R^a$, $R^b$, $R^c$, $R^d$, $R^e$, $R^f$, $R^g$, $R^h$, $R^i$, $R^j$, $R^k$ and $R^l$ are each independently a hydrogen atom or a substituent.

Examples of the "substituent" for $R^a$, $R^b$, $R^c$, $R^d$, $R^e$, $R^f$, $R^g$, $R^h$, $R^i$, $R^j$, $R^k$ or $R^l$ include the above-mentioned "substituent".

In (a),
$R^a$ is preferably
(1) a hydrogen atom,
(2) a cyano group,
(3) a $C_{1-6}$ alkyl group (e.g., methyl, ethyl, isopropyl) optionally substituted by 1 to 3 hydroxy groups, or
(4) a mono- or di-$C_{1-6}$ alkyl-carbamoyl group (e.g., dimethylcarbamoyl).
$R^a$ is more preferably a $C_{1-6}$ alkyl group (e.g., ethyl, isopropyl).
$R^b$ is preferably
(1) a hydrogen atom,
(2) a halogen atom (e.g., a chlorine atom, a bromine atom), or
(3) a $C_{1-6}$ alkyl group (e.g., methyl).
$R^b$ is more preferably a hydrogen atom.
In (b),
$R^c$ is preferably
(1) a hydrogen atom, or
(2) a $C_{1-6}$ alkyl group (e.g., methyl, ethyl, isopropyl).
In (c),
$R^d$ is preferably a $C_{1-6}$ alkyl group (e.g., methyl).
In (d),
$R^e$ is preferably a $C_{1-6}$ alkyl group (e.g., methyl, ethyl, isopropyl).
$R^f$ is preferably a hydrogen atom.
In (e),
$R^g$ is preferably a $C_{1-6}$ alkyl group (e.g., methyl).
$R^h$ is preferably a hydrogen atom.
In (f),
$R^i$ is preferably a $C_{1-6}$ alkyl group (e.g., methyl).
In (g),
$R^j$ is preferably
(1) a hydrogen atom, or
(2) a $C_{1-6}$ alkyl group (e.g., methyl).
$R^k$ is preferably a hydrogen atom.
$R^l$ is preferably a hydrogen atom.
The ring structure for Ring A represented by

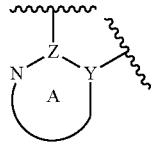

is more preferably the following ring structure (a).

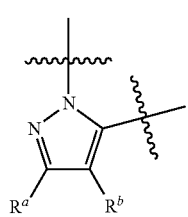

(a)

In (a),
$R^a$ is more preferably a $C_{1-6}$ alkyl group (e.g., ethyl, isopropyl).
$R^b$ is more preferably a hydrogen atom.

L is an optionally substituted methylene group, an oxygen atom, —O-$L^1$-, -$L^1$-O— or -$L^1$-$L^2$-. $L^1$ and $L^2$ are each independently an optionally substituted methylene group.

Examples of the substituent of the "optionally substituted methylene group" for L, $L^1$ or $L^2$ include substituents selected from Substituent Group A. The number of the substituents is preferably 1 to 3. When the number of the substituents is 2 or more, the respective substituents may be the same or different.

L is preferably an optionally substituted methylene group or —O-$L^1$- wherein $L^1$ is as defined above.

L is more preferably a methylene group or —O—$CH_2$—.

L is particularly preferably —O—$CH_2$—.

Ring B is an optionally further substituted 4- to 7-membered ring.

The "optionally further substituted 4- to 7-membered ring" for Ring B optionally has additional substituent(s) in addition to -L-6-membered ring (containing X, Y and Z) of the formula (I). Examples of the substituent include the above-mentioned "substituent". The number of the substituents is preferably 1 to 3. When the number of the substituents is 2 or more, the respective substituents may be the same or different.

Ring B is preferably a 4- to 7-membered ring (preferably a 6-membered ring (e.g., cyclohexane, piperidine, benzene, pyridine)) further substituted by 1 to 3 substituents selected from
(a) a $C_{6-14}$ aryl group (e.g., phenyl) optionally substituted by 1 to 3 substituents selected from
(i) a halogen atom (e.g., a fluorine atom), and
(ii) a $C_{1-6}$ alkyl group (e.g., methyl), and
(b) a 5- to 14-membered aromatic heterocyclic group (preferably a 5- or 6-membered monocyclic aromatic heterocyclic group (e.g., pyridyl, pyrimidinyl) or a 8- to 14-membered fused polycyclic (preferably bi- or tricyclic) aromatic heterocyclic group (e.g., quinazolinyl)) optionally substituted by 1 to 3 substituents selected from
(i) a halogen atom (e.g., a fluorine atom),
(ii) a $C_{1-6}$ alkyl group (e.g., methyl), and
(iii) a $C_{1-6}$ alkoxy group (e.g., methoxy).

Ring B is more preferably
(1) a cyclohexane ring further substituted by 1 to 3 $C_{6-14}$ aryl groups (e.g., phenyl),
(2) a piperidine ring further substituted by 1 to 3 substituents selected from
(a) a $C_{6-14}$ aryl group (e.g., phenyl) optionally substituted by 1 to 3 halogen atoms (e.g., a fluorine atom), and
(b) a 5- to 14-membered aromatic heterocyclic group (preferably a 5- or 6-membered monocyclic aromatic heterocyclic group (e.g., pyridyl, pyrimidinyl) or a 8- to 14-membered fused polycyclic (preferably bi- or tri-cyclic) aromatic heterocyclic group (e.g., quinazolinyl)) optionally substituted by 1 to 3 substituents selected from
(i) a halogen atom (e.g., a fluorine atom),
(ii) a $C_{1-6}$ alkyl group (e.g., methyl), and
(iii) a $C_{1-6}$ alkoxy group (e.g., methoxy),
(3) a benzene ring further substituted by 1 to 3 substituents selected from
(a) a $C_{6-14}$ aryl group (e.g., phenyl) optionally substituted by 1 to 3 substituents selected from
(i) a halogen atom (e.g., a fluorine atom)), and
(ii) a $C_{1-6}$ alkyl group (e.g., methyl), and
(b) a 5- to 14-membered aromatic heterocyclic group (preferably a 5- or 6-membered monocyclic aromatic heterocyclic group (e.g., pyridyl)) optionally substituted by 1 to 3 $C_{1-6}$ alkyl groups (e.g., methyl), or (4) a pyridine ring further substituted by 1 to 3 $C_{6-14}$ aryl groups (e.g., phenyl) optionally substituted by 1 to 3 halogen atoms (e.g., a fluorine atom).

Ring B is further more preferably a piperidine ring further substituted by 1 to 3 of 5- or 6-membered monocyclic aromatic heterocyclic groups (e.g., pyrimidinyl) optionally substituted by 1 to 3 halogen atoms (e.g., a fluorine atom).

Ring B is particularly preferably a piperidine ring further substituted by one pyrimidinyl optionally substituted by 1 to 3 halogen atoms (e.g., a fluorine atom).

In compound (I), the configuration based on the carbon atom that —$NHR^1$ is bonded to and the carbon atom that -L-Ring B is bonded to is preferably cis-form. That is, compound (I) is preferably represented by the formula (IA) or (IB):

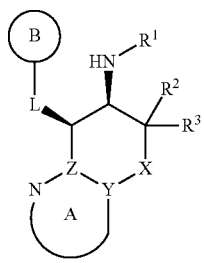

(IA)

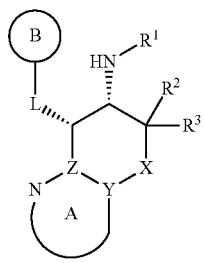

(IB)

wherein each symbol is as defined above,
more preferably represented by the formula (IA):

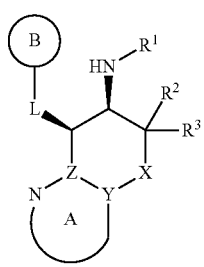

(IA)

wherein each symbol is as defined above.

Preferable embodiments of compound (I) include the following compounds. These compounds are preferably represented by the above formula (IA) or (IB), more preferably represented by the formula (IA).

[Compound A]
Compound (I) wherein
$R^1$ is
(1) an optionally substituted $C_{1-6}$ alkylsulfonyl group,
(2) an optionally substituted mono- or di-$C_{1-6}$ alkylcarbamoyl-carbonyl group, or
(3) an optionally substituted 3- to 6-membered cyclylcarbonyl group (preferably a 3- to 6-membered non-aromatic heterocyclylcarbonyl group);
$R^2$ and $R^3$ are both hydrogen atoms;
X is an optionally substituted methylene group;
Y and Z are each independently a carbon atom or a nitrogen atom;
Ring A is an optionally substituted 5- or 6-membered nitrogen-containing aromatic heterocycle;
L is an optionally substituted methylene group or —O-$L^1$- wherein $L^1$ is as defined above; and
Ring B is an optionally further substituted 4- to 7-membered ring.

[Compound B]
Compound (I) wherein
$R^1$ is
(1) a $C_{1-6}$ alkylsulfonyl group (e.g., methylsulfonyl, ethylsulfonyl),
(2) a mono- or di-$C_{1-6}$ alkyl-carbamoyl-carbonyl group (e.g., dimethylcarbamoylcarbonyl), or
(3) a 3- to 6-membered non-aromatic heterocyclylcarbonyl group (e.g., tetrahydrofurylcarbonyl);
$R^2$ and $R^3$ are both hydrogen atoms;
X is a methylene group;
Y and Z are each independently a carbon atom or a nitrogen atom;
Ring A is a 5- or 6-membered aromatic heterocycle (e.g., pyrazole, triazole (e.g., 1,2,3-triazole, 1,2,4-triazole), imidazole, thiazole, pyridine) optionally substituted by 1 to 3 substituents selected from
(a) a halogen atom (e.g., a chlorine atom, a bromine atom),
(b) a cyano group,
(c) a $C_{1-6}$ alkyl group (e.g., methyl, ethyl, isopropyl) optionally substituted by 1 to 3 hydroxy groups, and
(d) a mono- or di-$C_{1-6}$ alkyl-carbamoyl group (e.g., dimethylcarbamoyl);
L is a methylene group or —O—$CH_2$—; and
Ring B is a 4- to 7-membered ring (preferably a 6-membered ring (e.g., cyclohexane, piperidine, benzene, pyridine)) further substituted by 1 to 3 substituents selected from
(a) a $C_{6-14}$ aryl group (e.g., phenyl) optionally substituted by 1 to 3 substituents selected from
(i) a halogen atom (e.g., a fluorine atom), and
(ii) a $C_{1-6}$ alkyl group (e.g., methyl), and
(b) a 5- to 14-membered aromatic heterocyclic group (preferably a 5- or 6-membered monocyclic aromatic heterocyclic group (e.g., pyridyl, pyrimidinyl) or a 8- to 14-membered fused polycyclic (preferably bi- or tri-cyclic) aromatic heterocyclic group (e.g., quinazolinyl)) optionally substituted by 1 to 3 substituents selected from
(i) a halogen atom (e.g., a fluorine atom),
(ii) a $C_{1-6}$ alkyl group (e.g., methyl), and
(iii) a $C_{1-6}$ alkoxy group (e.g., methoxy).

[Compound C]
Compound (I) wherein
R¹ is
(1) a $C_{1-6}$ alkylsulfonyl group (e.g., methylsulfonyl, ethylsulfonyl),
(2) a mono- or alkyl-carbamoyl-carbonyl group (e.g., dimethylcarbamoylcarbonyl), or
(3) a 3- to 6-membered non-aromatic heterocyclylcarbonyl group (e.g., tetrahydrofurylcarbonyl);
R² and R³ are both hydrogen atoms;
X is a methylene group;
Y and Z are each independently a carbon atom or a nitrogen atom;
Ring A is
(1) a pyrazole ring optionally substituted by 1 to 3 substituents selected from
  (a) a halogen atom (e.g., a chlorine atom, a bromine atom),
  (b) a cyano group,
  (c) a $C_{1-6}$ alkyl group (e.g., methyl, ethyl, isopropyl) optionally substituted by 1 to 3 hydroxy groups, and
  (d) a mono- or di-$C_{1-6}$ alkyl-carbamoyl group (e.g., dimethylcarbamoyl),
(2) a triazole ring (e.g., 1,2,3-triazole, 1,2,4-triazole) optionally substituted by 1 to 3 $C_1$-6 alkyl groups (e.g., methyl, ethyl, isopropyl),
(3) an imidazole ring optionally substituted by 1 to 3 $C_{1-6}$ alkyl groups (e.g., methyl),
(4) a thiazole ring optionally substituted by 1 to 3 $C_{1-6}$ alkyl groups (e.g., methyl), or
(5) a pyridine ring optionally substituted by 1 to 3 $C_{1-6}$ alkyl groups (e.g., methyl);
L is a methylene group or —O—CH₂—; and
Ring B is
(1) a cyclohexane ring further substituted by 1 to 3 $C_{6-14}$ aryl groups (e.g., phenyl),
(2) a piperidine ring further substituted by 1 to 3 substituents selected from
  (a) a $C_{6-14}$ aryl group (e.g., phenyl) optionally substituted by 1 to 3 halogen atoms (e.g., a fluorine atom), and
  (b) a 5- to 14-membered aromatic heterocyclic group (preferably a 5- or 6-membered monocyclic aromatic heterocyclic group (e.g., pyridyl, pyrimidinyl) or a 8- to 14-membered fused polycyclic (preferably bi- or tri-cyclic) aromatic heterocyclic group (e.g., quinazolinyl)) optionally substituted by 1 to 3 substituents selected from
    (i) a halogen atom (e.g., a fluorine atom),
    (ii) a $C_{1-6}$ alkyl group (e.g., methyl), and
    (iii) a $C_{1-6}$ alkoxy group (e.g., methoxy),
(3) a benzene ring further substituted by 1 to 3 substituents selected from
  (a) a $C_{6-14}$ aryl group (e.g., phenyl) optionally substituted by 1 to 3 substituents selected from
    (i) a halogen atom (e.g., a fluorine atom), and
    (ii) a $C_{1-6}$ alkyl group (e.g., methyl), and
  (b) a 5- to 14-membered aromatic heterocyclic group (preferably a 5- or 6-membered monocyclic aromatic heterocyclic group (e.g., pyridyl)) optionally substituted by 1 to 3 $C_{1-6}$ alkyl groups (e.g., methyl), or
(4) a pyridine ring further substituted by 1 to 3 $C_{6-14}$ aryl groups (e.g., phenyl) optionally substituted by 1 to 3 halogen atoms (e.g., a fluorine atom).

[Compound Ca]
[Compound B] or [Compound C] wherein the ring structure for Ring A represented by

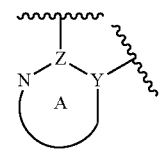

is the following ring structures (a) to (g)

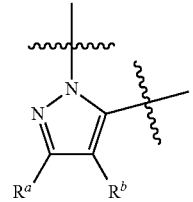
(a)

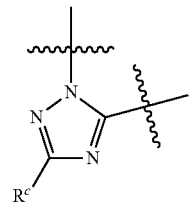
(b)

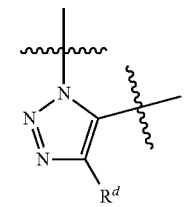
(c)

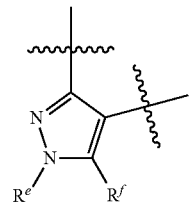
(d)

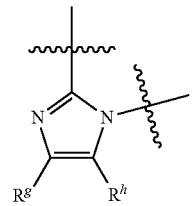
(e)

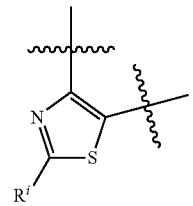
(f)

-continued

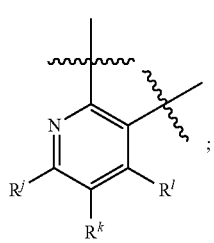
(g)

in (a),
$R^a$ is
(1) a hydrogen atom,
(2) a cyano group,
(3) a $C_{1-6}$ alkyl group (e.g., methyl, ethyl, isopropyl) optionally substituted by 1 to 3 hydroxy groups, or
(4) a mono- or di-$C_{1-6}$ alkyl-carbamoyl group (e.g., dimethylcarbamoyl); and
$R^b$ is
(1) a hydrogen atom,
(2) a halogen atom (e.g., a chlorine atom, a bromine atom), or
(3) a $C_{1-6}$ alkyl group (e.g., methyl);
in (b),
$R^c$ is
(1) a hydrogen atom, or
(2) a $C_{1-6}$ alkyl group (e.g., methyl, ethyl, isopropyl);
in (c),
$R^d$ is a $C_{1-6}$ alkyl group (e.g., methyl);
in (d),
$R^e$ is a $C_{1-6}$ alkyl group (e.g., methyl, ethyl, isopropyl); and
$R^f$ is a hydrogen atom;
in (e),
$R^g$ is a $C_{1-6}$ alkyl group (e.g., methyl); and
$R^h$ is a hydrogen atom;
in (f),
$R^i$ is a $C_{1-6}$ alkyl group (e.g., methyl);
in (g),
$R^j$ is
(1) a hydrogen atom, or
(2) a $C_{1-6}$ alkyl group (e.g., methyl);
$R^k$ is a hydrogen atom; and
$R^l$ is a hydrogen atom.

[Compound D]
Compound (I) wherein
$R^1$ is a $C_{1-6}$ alkylsulfonyl group (e.g., methylsulfonyl);
$R^2$ and $R^3$ are both hydrogen atoms;
X is a methylene group;
Y and Z are each independently a carbon atom or a nitrogen atom;
Ring A is a pyrazole ring optionally substituted by 1 to 3 $C_{1-6}$ alkyl groups (e.g., ethyl, isopropyl);
L is —O—CH$_2$—; and
Ring B is a piperidine ring further substituted by 1 to 3 of 5- or 6-membered monocyclic aromatic heterocyclic groups (e.g., pyrimidinyl) optionally substituted by 1 to 3 halogen atoms (e.g., a fluorine atom).

[Compound Da]
[Compound D] wherein
the ring structure for Ring A represented by

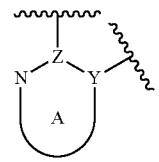

is the following ring structure (a)

(a)

in (a),
$R^a$ is a $C_{1-6}$ alkyl group (e.g., ethyl, isopropyl); and
$R^b$ is a hydrogen atom.

Specific examples of compound (I) include the compounds of the below-mentioned Examples 1 to 63.

Specifically, compound (I) is preferably N-[7-({[1-(5-fluoropyrimidin-2-yl)piperidin-4-yl]oxy}methyl)-2-(propan-2-yl)-4,5,6,7-tetrahydropyrazolo[1,5-a]pyridin-6-yl] methanesulfonamide or a salt thereof (Example 24); N-[2-ethyl-7-({[1-(5-fluoropyrimidin-2-yl)piperidin-4-yl] oxy}methyl)-4,5,6,7-tetrahydropyrazolo[1,5-a]pyridin-6-yl] methanesulfonamide or a salt thereof (Example 33); or, N-[2-(propan-2-yl)-7-({[1-(pyrimidin-2-yl)piperidin-4-yl] oxy}methyl)-4,5,6,7-tetrahydropyrazolo[1,5-a]pyridin-6-yl] methanesulfonamide or a salt thereof (Example 56).

As a salt of a compound represented by the formula (I), a pharmacologically acceptable salt is preferable, and examples of such salt include a salt with inorganic base, a salt with organic base, a salt with inorganic acid, a salt with organic acid, a salt with basic or acidic amino acid and the like.

Preferable examples of the salt with inorganic base include alkali metal salts such as sodium salt, potassium salt and the like, alkaline earth metal salts such as calcium salt, magnesium salt and the like, aluminum salt, ammonium salt and the like.

Preferable examples of the salt with organic base include salts with trimethylamine, triethylamine, pyridine, picoline, ethanolamine, diethanolamine, triethanolamine, tromethamine[tris(hydroxymethyl)methylamine], tert-butylamine, cyclohexylamine, benzylamine, dicyclohexylamine, N,N-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

The production method of the compound of the present invention is explained below.

The raw material compound and reagent used and the compound obtained in each step in the following production method may be each in a form of a salt, and examples of such salt include those similar to the salts of the compound represented by the formula (I), and the like.

When the compound obtained in each step is a free form, it can be converted to the objective salt according to a method known per se. When the compound obtained in each step is a salt, it can be converted to the objective free form or the other salt according to a method known per se.

The compound obtained in each step can be used directly as the reaction mixture or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, column chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally −78° C.-300° C., preferably −78° C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature −300° C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents-20 equivalents, preferably 0.8 equivalents-5 equivalents, relative to the substrate, unless otherwise specified. When the reagent is used as a catalyst, the reagent is used in an amount of 0.001 equivalent-1 equivalent, preferably 0.01 equivalent-0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.

alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; water.

The above-mentioned solvent can be used in a mixture of two or more kinds thereof in an appropriate ratio.

When a base is used for the reaction in each step, examples thereof include those described in Examples and the following bases.

inorganic bases: sodium hydroxide, magnesium hydroxide, sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like;
metal amides: sodium amide, lithium diisopropylamide, lithium hexamethyldisilazide and the like;
organic lithiums: n-butyllithium and the like.

When an acid or an acid catalyst is used for the reaction in each step, examples thereof include those described in Examples and the following acids and acid catalysts.

inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like;
Lewis acid: boron trifluoride diethyl ether complex, zinc iodide, anhydrous aluminum chloride, anhydrous zinc chloride, anhydrous iron chloride and the like.

Unless otherwise specified, the reaction in each step is carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & Sons Inc.); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, the protection or deprotection reaction of an functional group is carried out according to a method known per se, for example, the method described in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski), or the like, or the method described in Examples.

Examples of the protecting group for a hydroxy group of an alcohol and the like and a phenolic hydroxy group include ether-type protecting groups such as methoxymethyl ether, benzyl ether, tert-butyldimethylsilyl ether, tetrahydropyranyl ether and the like; carboxylate ester-type protecting groups such as acetate ester and the like; sulfonate ester-type protecting groups such as methanesulfonate ester and the like; carbonate ester-type protecting groups such as tert-butylcarbonate and the like, and the like.

Examples of the protecting group for a carbonyl group of an aldehyde include acetal-type protecting groups such as dimethylacetal and the like; cyclic acetal-type protecting groups such as 1,3-dioxane and the like, and the like.

Examples of the protecting group for a carbonyl group of a ketone include ketal-type protecting groups such as dimethylketal and the like; cyclic ketal-type protecting groups such as 1,3-dioxane and the like; oxime-type protecting groups such as O-methyloxime and the like; hydrazone-type protecting groups such as N,N-dimethylhydrazone and the like, and the like.

Examples of the protecting group for a carboxyl group include ester-type protecting groups such as methyl ester and the like; amide-type protecting groups such as N,N-dimethylamide and the like, and the like.

Examples of the protecting group for a thiol include ether-type protecting groups such as benzyl thioether and the like; ester-type protecting groups such as thioacetate ester, thiocarbonate, thiocarbamate and the like, and the like.

Examples of the protecting group for an amino group and an aromatic heterocycle such as imidazole, pyrrole, indole and the like include carbamate-type protecting groups such as benzyl carbamate and the like; amide-type protecting groups such as acetamide and the like; alkyl amine-type protecting groups such as N-triphenylmethylamine and the like; sulfonamide-type protecting groups such as methanesulfonamide and the like, and the like.

The protecting groups can be removed according to a method known per se, for example, by employing a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like.

When reduction reaction is carried out in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When carbon-carbon double bond or triple bond is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (mCPBA), hydrogen peroxide, tert-butylhydroperoxide and the like; perchlorates such as tetrabutylammonium perchlorate and the like; chlorates such as sodium chlorate and the like; chlorites such as sodium chlorite and the like; periodates such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, a combination of a Lewis acid and an acid chloride or a combination of a Lewis acid and an alkylating agent (e.g., an alkyl halide, an alcohol, an olefin etc.) is used as a reagent. Alternatively, an organic acid or an inorganic acid can also be used instead of a Lewis acid, and an anhydride such as acetic anhydride and the like can also be used instead of an acid chloride.

When aromatic nucleophilic substitution reaction is carried out in each step, a nucleophile (e.g., an amine, imidazole etc.) and a base (e.g., an organic base etc.) are used as a reagent.

When nucleophilic addition reaction by a carbo anion, nucleophilic 1,4-addition reaction (Michael addition reaction) by a carbo anion or nucleophilic substitution reaction by a carbo anion is carried out in each step, and examples of the base to be used for generation of the carbo anion include organic lithiums, metal alkoxides, inorganic bases, organic bases and the like.

When Grignard reaction is carried out in each step, examples of the Grignard reagent to be used include arylmagnesium halides such as phenylmagnesium bromide and the like; and alkylmagnesium halides such as methylmagnesium bromide and the like. The Grignard reagent can be prepared according to a method known per se, for example, by reacting an alkyl halide or an aryl halide with a metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, and the like are employed.

When reductive amination reaction is carried out in each step, examples of the reducing agent to be used include sodium triacetoxyborohydride, sodium cyanoborohydride, hydrogen, formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, an azodicarboxylate (e.g., diethyl azodicarboxylate (DEAD), diisopropyl azodicarboxylate (DIAD) etc.) and triphenylphosphine are used as a reagent.

When esterification reaction, amidation reaction or urea formation reaction is carried out in each step, examples of the reagent to be used include acyl halides such as acid chlorides, acid bromides and the like; activated carboxylic acids such as acid anhydrides, activated esters, sulfates and the like. Examples of the activating agent of the carboxylic acid include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride n-hydrate (DMT-MM) and the like; carbonate condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; 0-(7-azabenzotriazol-1-yl)-N,N,N',N'-tetramethyluronium hexafluorophosphorate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocenepalladium(II) chloride and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base can be added to the reaction system, and examples thereof include inorganic bases and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis(4-methoxyphenyl)-1,3,2,4-dithiadiphosphetane-2,4-disulfide (Lawesson reagent) etc.) can also be used instead of phosphorus pentasulfide.

When Wohl-Ziegler reaction is carried out in each step, examples of the halogenating agent to be used include N-iodosuccinimide, N-bromosuccinimide (NBS), N-chlorosuccinimide (NCS), bromine, sulfuryl chloride and the like. In addition, the reaction can be accelerated by subjecting a radical initiator such as heat, light, benzoyl peroxide, azobisisobutyronitrile and the like to the reaction system reaction.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method for producing an alkyl halide by reacting an alcohol with triphenylphosphine and carbon tetrachloride or carbon tetrabromide or the like can be employed. Alternatively, a method for producing an alkyl halide via two steps comprising converting an alcohol to the corresponding sulfonate, and then reacting the sulfonate with lithium bromide, lithium chloride or sodium iodide can also be employed.

When Arbuzov reaction is carried out in each step, examples of the reagent to be used include alkyl halides such as ethyl bromoacetate and the like; and phosphites such as triethyl phosphite, tri(isopropyl) phosphite and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride and the like.

When hydrolysis reaction is carried out in each step, an acid or a base is used as a reagent. For acid hydrolysis reaction of tert-butyl ester, formic acid, triethylsilane and the like may be added to reductively-trap tert-butyl cation which is by-produced.

When dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid and the like.

Among compound (9) used in the below-mentioned Scheme 2, compound (9)-1 can be produced from compound (1) according to the method shown in the following Scheme 1. In the scheme, $LG^1$ and $LG^2$ are each independently a leaving group, $P^1$ is a protecting group, Hal is a halogen atom, $R^4$ is an optionally substituted $C_{1-6}$ alkyl group or an optionally substituted $C_{3-10}$ cycloalkyl group, and the other symbols are as defined above.

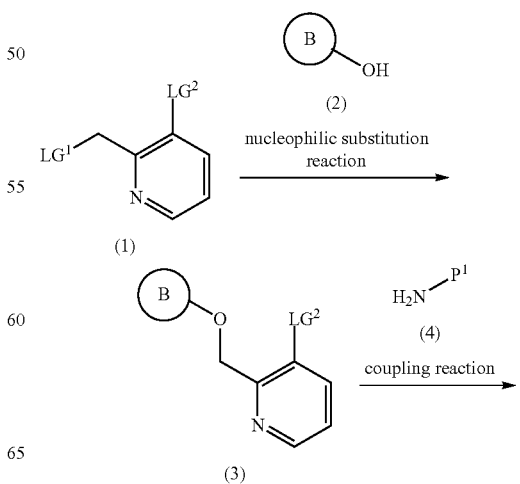

Scheme 1

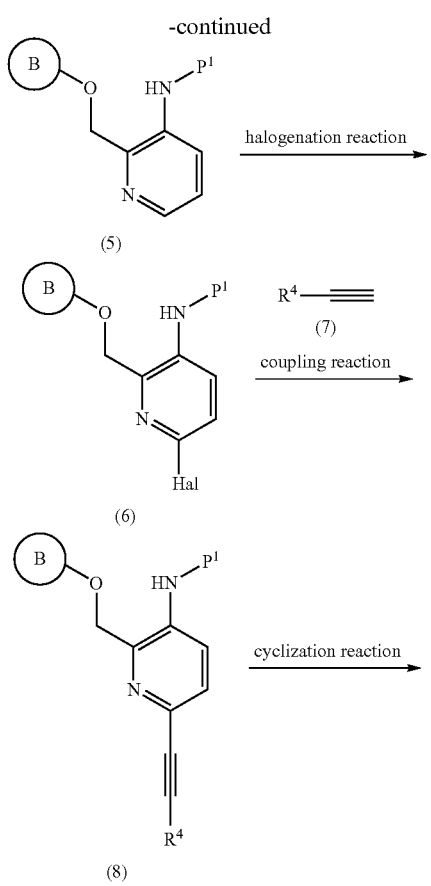

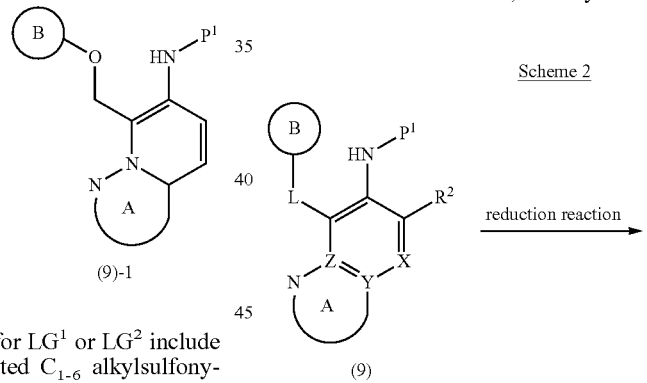

Scheme 2

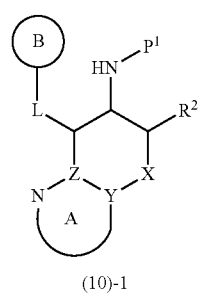

in the presence of a base. Examples of the base to be used include alkali metal hydrides, organic lithiums and the like. Compound (2) may be a commercially available product, or can be produced according to a method known per se or a method analogous thereto.

Compound (5) can be produced by subjecting compound (3) to a coupling reaction with compound (4). Compound (4) may be a commercially available product, or can be produced according to a method known per se or a method analogous thereto.

Compound (6) can be produced by subjecting compound (5) to a halogenation reaction. Examples of the halogenating reagent to be used include N-chlorosuccinimide (NCS), N-bromosuccinimide (NBS), bromine and the like.

Compound (8) can be produced by subjecting compound (6) to a coupling reaction with compound (7). Compound (7) may be a commercially available product, or can be produced according to a method known per se or a method analogous thereto.

Compound (9)-1 can be produced by subjecting compound (8) to a cyclization reaction in the presence of an aminating reagent and a base. Examples of the aminating reagent to be used include 2-[(aminooxy)sulfonyl]-1,3,5-trimethylbenzene and the like. Examples of the base to be used include inorganic bases, organic bases, alkali metal hydrides and the like.

Among compound (10) used in the below-mentioned Scheme 3, compound (10)-1 can be produced from compound (9) according to the method shown in the following Scheme 2. In the scheme, each symbol is as defined above.

Examples of the "leaving group" for $LG^1$ or $LG^2$ include halogen atoms, optionally halogenated $C_{1-6}$ alkylsulfonyloxy groups (e.g., methanesulfonyloxy, ethanesulfonyloxy, trifluoromethanesulfonyloxy), $C_{6-14}$ arylsulfonyloxy groups optionally substituted by $C_{1-6}$ alkyl group(s) (e.g., benzenesulfonyloxy, toluenesulfonyloxy) and the like.

Examples of the "protecting group" for $P^1$ include those exemplified as the above-mentioned "protecting group for an amino group and an aromatic heterocycle such as imidazole, pyrrole, indole and the like".

Examples of the substituent of the "optionally substituted $C_{1-6}$ alkyl group" and "optionally substituted $C_{3-10}$ cycloalkyl group" for $R^4$ include substituents selected from Substituent Group A. The number of the substituents is preferably 1 to 3. When the number of the substituents is 2 or more, the respective substituents may be the same or different.

Compound (1) may be a commercially available product, or can be produced according to a method known per se or a method analogous thereto.

Compound (3) can be produced by subjecting compound (1) to a nucleophilic substitution reaction with compound (2)

Compound (I) can be produced from compound (10) according to the method shown in the following Scheme 3. In the scheme, $LG^3$ is a leaving group, and the other symbols are as defined above.

Scheme 3

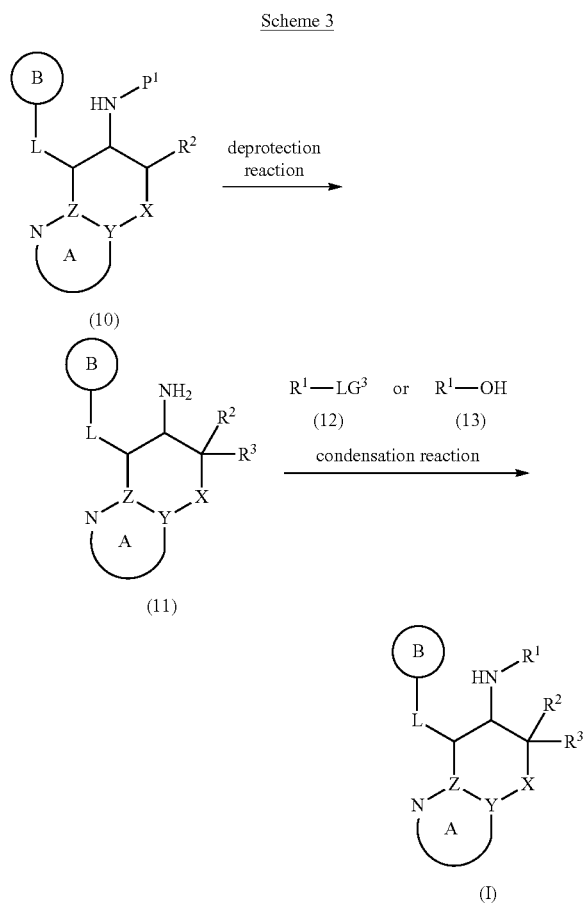

Examples of the "leaving group" for LG³ include those exemplified as the "leaving group" for LG¹ or LG².

Compound (I) can be produced by subjecting compound (11) to a condensation reaction with compound (12) or compound (13). The condensation reaction includes amidation reaction, urea formation reaction, carbamation reaction, sulfonamidation reaction, sulfamidation reaction, sulfamatation reaction and the like. Examples of compound (13) to be used include acyl halides such as acid chlorides, acid bromides, alkyl chloroformates, carbamoyl chlorides and the like, sulfonyl chlorides, sulfamoyl chlorides, alkyl chlorosulfates and the like. Compound (12) and compound (13) may be a commercially available product, or can be produced according to a method known per se or a method analogous thereto.

In the thus-obtained compound (I), an intramolecular functional group can also be converted to an object functional group by a combination of chemical reactions known per se. Examples of the chemical reaction include oxidation reaction, reduction reaction, alkylation reaction, acylation reaction, ureation reaction, hydrolysis reaction, amination reaction, esterification reaction, aryl coupling reaction, deprotection reaction and the like.

In the above-mentioned production method, when a starting compound has an amino group, a carboxyl group, a hydroxy group, a carbonyl group or a mercapto group as a substituent, a protecting group generally used in the peptide chemistry may be introduced into these groups, and the object compound can be obtained by removing the protecting group as necessary after the reaction.

Compound (I) obtained by the above-mentioned production method can be isolated and purified by a known means, such as solvent extraction, liquid conversion, phase transfer, crystallization, recrystallization, chromatography and the like.

When compound (I) contains optical isomer, stereoisomer, regio isomer and rotamer, these compounds are also included in compound (I), and each can be obtained as a single product by a synthesis method or a separation method known per se. For example, when an optical isomer exists in compound (I), an optical isomer resolved from the compound is also encompassed in compound (I).

Here, an optical isomer can be produced by a method known per se.

Compound (I) may be a crystal.

A crystal of compound (I) (hereinafter sometimes to be abbreviated as the crystal of the present invention) can be produced by crystallizing compound (I), by applying a crystallization method known per se.

In the present specification, the melting point means a melting point measured, for example, by micro melting point apparatus (Yanako, MP-500D or Buchi, B-545), DSC (differential scanning calorimetry analysis) apparatus (METTLER TOLEDO, DSC1) and the like.

Generally, the melting point sometimes varies depending on the measurement device, measurement condition and the like. The crystal in the present specification may be a crystal showing a melting point different from the values described in the present specification as long as the difference is within a general error range.

The crystal of the present invention is superior in the physicochemical properties (e.g., melting point, solubility, stability) and biological properties (e.g., pharmacokinetics (absorbability, distribution, metabolism, excretion), efficacy expression), and is extremely useful as a medicament.

Compound (I) may be used as a prodrug. A prodrug of the compound (I) means a compound which is converted to the compound (I) of the present invention with a reaction due to an enzyme, an gastric acid, etc. under the physiological condition in the living body, that is, a compound which is converted to the compound (I) of the present invention with oxidation, reduction, hydrolysis, etc. according to an enzyme; a compound which is converted to the compound (I) of the present invention by hydrolysis etc. due to gastric acid, etc.

A prodrug of compound (I) may be
a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation, dimethylaminomethylcarbonylation, etc.); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Any of these compounds can be produced from compound (I) by a method known per se.

A prodrug for compound (I) may also be one which is converted into compound (I) under a physiological condition, such as those described in IYAKUHIN no KAIHATSU (Development of Pharmaceuticals), Vol. 7, Design of Molecules, p. 163-198, Published by HIROKAWA SHOTEN (1990).

In the present specification, a prodrug may form a salt, and as such salt, those exemplified as a salt of the compound represented by the above-mentioned formula (I) can be mentioned.

Compound (I) may be labeled with an isotope (e.g., $^3$H, $^{13}$C, $^{14}$C, $^{18}$F, $^{35}$S, $^{125}$I) and the like.

Compound (I) labeled with or substituted by an isotope can be used, for example, as a tracer used for Positron Emission Tomography (PET) (PET tracer), and is useful in the field of medical diagnosis and the like.

Furthermore, compound (I) may be a hydrate or a non-hydrate, or a non-solvate (e.g., anhydride), or a solvate (e.g., hydrate).

Compound (I) also encompasses a deuterium conversion form wherein $^1$H is converted to $^2$H(D).

Furthermore, compound (I) may be a pharmaceutically acceptable cocrystal or cocrystal salt. The cocrystal or cocrystal salt means a crystalline substance constituted with two or more special solids at room temperature, each having different physical properties (e.g., structure, melting point, melting heat, hygroscopicity, solubility and stability). The cocrystal or cocrystal salt can be produced by a cocrystallization method known per se.

Compound (I) or a prodrug thereof (hereinafter sometimes to be simply abbreviated as the compound of the present invention) can be used as it is or in the form of a pharmaceutical composition (also referred to as a medicament) by mixing with a pharmacologically acceptable carrier etc. to mammals (e.g., human, mouse, rat, rabbit, dog, cat, bovine, horse, swine, monkey) as an agent for the prophylaxis or treatment of various diseases mentioned below.

As pharmacologically acceptable carriers, various organic or inorganic carrier substances conventionally used as preparation materials can be used. These are incorporated as excipient, lubricant, binder and disintegrant for solid preparations; or solvent, solubilizing agent, suspending agent, isotonicity agent, buffer and soothing agent for liquid preparations; and the like; and preparation additives such as preservative, antioxidant, colorant, sweetening agent and the like can be added as necessary.

Preferable examples of the excipient include lactose, sucrose, D-mannitol, D-sorbitol, starch, gelatinated starch, dextrin, crystalline cellulose, low-substituted hydroxypropylcellulose, sodium carboxymethylcellulose, gum arabic, pullulan, light anhydrous silicic acid, synthetic aluminum silicate and magnesium alumino metasilicate.

Preferable examples of the lubricant include magnesium stearate, calcium stearate, talc and colloidal silica.

Preferable examples of the binder include gelatinated starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, croscarmellose sodium, sodium carboxymethyl starch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionate, lecithin, benzalkonium chloride, benzethonium chloride, glycerol monostearate and the like; hydrophilic polymers such as poly(vinyl alcohol), polyvinylpyrrolidone, carboxymethylcellulose sodium, methylcellulose, hydroxymethylcellulose, hydroxyethylcellulose, hydroxypropylcellulose and the like, polysorbates; and polyoxyethylene hydrogenated castor oil.

Preferable examples of the isotonicity agent include sodium chloride, glycerol, D-mannitol, D-sorbitol and glucose.

Preferable examples of the buffer include buffers of phosphate, acetate, carbonate, citrate etc.

Preferable examples of the soothing agent include benzyl alcohol.

Preferable examples of the preservative include p-oxybenzoate esters, chlorobutanol, benzyl alcohol, phenethyl alcohol, dehydroacetic acid and sorbic acid.

Preferable examples of the antioxidant include sulfite salts and ascorbate salts.

Preferable examples of the colorant include aqueous food tar colors (e.g., food colors such as Food Color Red Nos. 2 and 3, Food Color Yellow Nos. 4 and 5, Food Color Blue Nos. 1 and 2 and the like food colors), water insoluble lake dyes (e.g., aluminum salt of the above-mentioned aqueous food tar color), natural dyes (e.g., β-carotene, chlorophyll, red iron oxide) and the like.

Preferable examples of the sweetening agent include saccharin sodium, dipotassium glycyrrhizinate, aspartame and stevia.

Examples of the dosage form of the above-mentioned pharmaceutical composition include oral preparations such as tablet (including sugar-coated tablet, film-coated tablet, sublingual tablet, orally disintegrating tablet, buccal tablet), capsule (including soft capsule, microcapsule), pill, granule, powder, troche, syrup, liquid, emulsion, suspension, aerosol, films (e.g., orally disintegrable films, oral mucosa-adhesive film) and the like; and parenteral agents such as injection (e.g., subcutaneous injection, intravenous injection, intramuscular injection, intraperitoneal injection, drip infusion), external preparation (e.g., transdermal absorption type preparation, ointment, lotion, adhesive preparation), suppository (e.g., rectal suppository, vaginal suppository), pellet, nasal preparation, pulmonary preparation (inhalant), eye drop and the like. The compound and medicament of the present invention can be respectively safely administered orally or parenterally (e.g., intrarectal, intravenous, intraarterial, intramuscular, subcutaneous, intraorgan, intranasal, intradermal, instillation, intracerebral, intravaginal, intraperitoneal, intratumoral, proximal tumor administrations, and administration to the lesion).

These preparations may be a release control preparation (e.g., sustained-release microcapsule) such as an immediate-release preparation, a sustained-release preparation and the like.

The pharmaceutical composition can be produced according to a method conventionally used in the field of pharmaceutical formulation, for example, the method described in the Japanese Pharmacopoeia, and the like.

While the content of the compound of the present invention in the pharmaceutical composition of the present invention varies depending on the dosage form, dose of the compound of the present invention and the like, it is, for example, about 0.1 to 100 wt %.

When an oral preparation is produced, coating may be applied where necessary for the purpose of taste masking, enteric solubility or sustainability.

Examples of the coating base used for coating include sugar coating base, water-soluble film coating base, enteric film coating base, and sustained-release film coating base.

As the sugar coating base, sucrose is used, and one or more kinds selected from talc, and the precipitated calcium carbonate, gelatin, gum arabic, pullulan, carnauba wax and the like may be further used in combination.

Examples of the water-soluble film coating base include cellulose polymers such as hydroxypropylcellulose, hydroxypropylmethylcellulose, hydroxyethylcellulose, methylhydroxyethylcellulose and the like; synthetic polymers such as polyvinyl acetal diethylaminoacetate, aminoalkylmethacrylate copolymer E [Eudragit E (trade name)], polyvinylpyrrolidone and the like; and polysaccharides such as pullulan and the like.

Examples of the enteric film coating base include cellulose polymers such as hydroxypropylmethylcellulose phthalate, hydroxypropylmethylcellulose acetate succinate, carboxymethylethylcellulose, cellulose acetate phthalate and the like; acrylic acid polymers such as methacrylic acid copolymer L [Eudragit L (trade name)], methacrylic acid copolymer LD [Eudragit L-30D-55 (trade name)], methacrylic acid copolymer S [Eudragit S (trade name)] and the like; and naturally-occurring substances such as shellac and the like.

Examples of the sustained-release film coating base include cellulose polymers such as ethylcellulose and the like; and acrylic acid polymers such as aminoalkylmethacrylate copolymer RS [Eudragit RS (trade name)], ethyl acrylate-methyl methacrylate copolymer suspension [Eudragit NE (trade name)] and the like.

Two or more kinds of the above-mentioned coating bases may be used in a mixture at an appropriate ratio. In addition, for example, light shielding agents such as titanium oxide, red ferric oxide and the like may also be used during coating.

Since the compound of the present invention shows low toxicity (e.g., acute toxicity, chronic toxicity, genetic toxicity, reproductive toxicity, cardiotoxicity, carcinogenicity) and less side effects, it can be used as a prophylactic or therapeutic agent, or diagnostic agent for various diseases in mammals (e.g., human, bovine, horse, dog, cat, monkey, mouse, rat).

The compound of the present invention has an excellent an orexin type 2 receptor agonist activity, and may treat, prevent or ameliorate the risk of various neurological and psychiatric diseases associated with an orexin type 2 receptor. The compound of the present invention is useful as an agent for the prophylaxis or treatment of various diseases such as narcolepsy, idiopathic hypersomnia, hypersomnia, sleep apnea syndrome, narcolepsy syndrome accompanied by narcolepsy-like symptoms, hypersomnia syndrome accompanied by daytime hypersomnia (e.g., Kleine Levin syndrome, major depression with hypersomnia, Lewy body dementia, Parkinson's disease, progressive supranuclear paralysis, Prader-Willi syndrome, Moebius syndrome, hypoventilation syndrome, Niemann-Pick disease type C, brain contusion, cerebral infarction, brain tumor, muscular dystrophy, multiple sclerosis, acute disseminated encephalomyelitis, Guillain-Barre syndrome, Rasmussen's encephalitis, Wernicke's encephalitis, limbic encephalitis, Hashimoto's encephalopathy), coma, loss of consciousness, obesity (e.g., malignant mastocytosis, exogenous obesity, hyperinsulinar obesity, hyperplasmic obesity, hypop hyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity), insulin resistance syndrome, Alzheimer's disease, disturbance of consciousness such as coma and the like, side effects and complications due to anesthesia, sleep disturbance, sleep problem, insomnia, Intermittent sleep, nocturnal myoclonus, REM sleep interruption, jet lag, jet lag syndrome, sleep disorder of alternating worker, sleep disorder, night terror, depression, major depression, sleepwalking disease, enuresis, sleep disorder, Alzheimer's dusk, diseases associated with circadian rhythm, fibromyalgia, condition arising from decline in the quality of sleep, overeating, obsessive compulsive eating disorder, obesity-related disease, hypertension, diabetes, elevated plasma insulin concentration and insulin resistance, hyperlipidemia, hyperlipemia, endometrial cancer, breast cancer, prostate cancer, colorectal cancer, cancer, osteoarthritis, obstructive sleep apnea, cholelithiasis, gallstones, cardiac disease, abnormal heartbeat, arrhythmia, myocardial infarction, congestive cardiac failure, cardiac failure, coronary heart disease, cardiovascular disorder, sudden death, polycysticovarian disease, craniopharingioma, Froelich's syndrome, growth hormone deficient, normal mutant short stature, Turner's syndrome, children suffering from acute lymphoblastic leukemia, syndrome X, reproductive hormone abnormality, declining fertility, infertility, male gonadal function decline, sexual and reproductive dysfunction such as female male hirsutism, fetal defects associated with pregnant women obesity, gastrointestinal motility disorders such as obesity-related gastroesophageal reflux, obesity hypoventilation syndrome (Pickwick syndrome), respiratory diseases such as dyspnea, inflammation such as systemic inflammation of the vascular system, arteriosclerosis, hypercholesterolemia, hyperuricemia, lower back pain, gall bladder disease, gout, kidney cancer, risk of secondary outcomes of obesity such as lowering the risk of left ventricular hypertrophy, migraine pain, headache, neuropathic pain, Parkinson's disease, psychosis, schizophrenia, facial flushing, night sweats, diseases of the genital/urinary system, diseases related to sexual function or fertility, dysthymic disorder, bipolar disorder, bipolar I disorder, bipolar II disorder, cyclothymic disorder, acute stress disorder, agoraphobia, generalized anxiety disorder, obsessive disorder, panic attack, panic disorder, posttraumatic stress disorder, separation anxiety disorder, social phobia, anxiety disorder, acute neurological and psychiatric disorders such as cardiac bypass surgery and post-transplant cerebral deficit, stroke, ischemic stroke, cerebral ischemia, spinal cord trauma, head trauma, perinatal hypoxia, cardiac arrest, hypoglycemic nerve injury, Huntington's disease, amyotrophic lateral sclerosis, multiple sclerosis, eye damage, retinopathy, cognitive impairment, muscle spasm, tremor, epilepsy, disorders associated with muscle spasticity, delirium, amnestic disorder, age-related cognitive decline, schizoaffective disorder, delusional disorder, drug addiction, dyskinesia, chronic fatigue syndrome, fatigue, medication-induced Parkinsonism syndrome, Jill-do La Tourette's syndrome, chorea, myoclonus, tic, restless legs syndrome, dystonia, dyskinesia, attention deficit hyperactivity disorder (ADHD), behavior disorder, urinary incontinence, withdrawal symptoms, trigeminal neuralgia, hearing loss, tinnitus, nerve damage, retinopathy, macular degeneration, vomiting, cerebral edema, pain, bone pain, arthralgia, toothache, cataplexy, and traumatic brain injury.

Particularly, the compound of the present invention is useful as an agent for the prophylaxis or treatment of narcolepsy, idiopathic hypersomnia, hypersomnia, sleep apnea syndrome, narcolepsy syndrome accompanied by narcolepsy-like symptoms, hypersomnia syndrome accompanied by daytime hypersomnia (e.g., Parkinson's disease, Guillain-Barre syndrome and Kleine Levin syndrome), Alzheimer's disease, obesity, insulin resistance syndrome, cardiac failure, diseases related to bone loss, sepsis, disturbance of consciousness such as coma and the like, side effects and complications due to anesthesia, and the like, or anesthetic antagonist.

While the dose of the compound of the present invention varies depending on the subject of administration, administration route, target disease, symptom and the like, for example, when the compound of the present invention is administered orally or parenterally to an adult patient, its dose is for example, about 0.01 to 100 mg/kg body weight per dose, preferably 0.1 to 50 mg/kg body weight per dose and more preferably 0.5 to 20 mg/kg body weight per dose. This amount is desirably administered in one to 3 portions daily.

The compound of the present invention can be used in combination with other drugs (hereinafter to be abbreviated as concomitant drug).

By combining the compound of the present invention and a concomitant drug, a superior effect, for example, (1) the dose can be reduced as compared to single administration of the compound of the present invention or a concomitant drug,
(2) the drug to be combined with the compound of the present invention can be selected according to the condition of patients (mild case, severe case and the like),
(3) the period of treatment can be set longer by selecting a concomitant drug having different action and mechanism from the compound of the present invention,
(4) a sustained treatment effect can be designed by selecting a concomitant drug having different action and mechanism from the compound of the present invention,
(5) a synergistic effect can be afforded by a combined use of the compound of the present invention and a concomitant drug, and the like, can be achieved.

In the present specification, the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof, or the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the combination agent of the present invention and the concomitant drug is not particularly limited, and the compound of the present invention and the concomitant drug only need to be combined on administration. Examples of such administration mode include the following: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The dose of the concomitant drug can be appropriately determined based on the dose employed in clinical situations. The mixing ratio of the compound of the present invention and a concomitant drug can be appropriately determined depending on the administration subject, administration route, target disease, symptom, combination and the like.

For example, the content of the compound of the present invention in the combination agent of the present invention differs depending on the form of a preparation, and usually from about 0.01 to about 100 wt %, preferably from about 0.1 to about 50 wt %, further preferably from about 0.5 to about 20 wt %, based on the whole preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the whole preparation.

The content of additives such as a carrier and the like in the combination agent of the present invention differs depending on the form of a preparation, and usually from about 1 to about 99.99 wt %, preferably from about 10 to about 90 wt %, based on the preparation.

Similar contents may be employed even when the compound of the present invention and a concomitant drug are separately formulated into preparations.

Examples of the concomitant drug include the followings. A therapeutic drug for narcolepsy (e.g., methylphenidate, amphetamine, pemoline, phenelzine, protriptyline, sodium oxybate, modafinil, caffeine), antiobesity drug (amphetamine, benzfetamine, bromocriptine, bupropion, diethylpropion, exenatide, fenfluramine, liothyronine, liraglutide, mazindol, methamphetamine, octreotide, octreotide, orlistat, phendimetrazine, phendimetrazine, phenmetrazine, phentermine, Qnexa (registered trade mark), phenylpropanolamine, pramlintide, propylhexedrine, recombinant leptin, sibutramine, topiramate, zimelidine, zonisamide, Lorcaserin, metformin), acetylcholine esterase inhibitor (e.g., donepezil, rivastigmine, galanthamine, zanapezil, idebenone, tacrine), antidementia agent (e.g., memantine), inhibitor of β amyloid protein production, secretion, accumulation, aggregation and/or deposition, β secretase inhibitor (e.g., 6-(4-biphenylyl)methoxy-2-[2-(N,N-dimethylamino)ethyl]tetralin, 6-(4-biphenylyl)methoxy-2-(N,N-dimethylamino)methyltetralin, 6-(4-biphenylyl)methoxy-2-(N,N-dipropylamino)methyltetralin, 2-(N,N-dimethylamino)methyl-6-(4'-methoxybiphenyl-4-yl)methoxytetralin, 6-(4-biphenylyl)methoxy-2-[2-(N,N-diethylamino)ethyl]tetralin, 2-[2-(N,N-dimethylamino)ethyl]-6-(4'-methylbiphenyl-4-yl)methoxytetralin, 2-[2-(N,N-dimethylamino)ethyl]-6-(4'-methoxybiphenyl-4-yl)methoxytetralin, 6-(2',4'-dimethoxybiphenyl-4-yl)methoxy-2-[2-(N,N-dimethylamino)ethyl]tetralin, 6-[4-(1,3-benzodioxol-5-yl)phenyl]methoxy-2-[2-(N,N-dimethylamino)ethyl]tetralin, 6-(3',4'-dimethoxybiphenyl-4-yl)methoxy-2-[2-(N,N-dimethylamino)ethyl]tetralin, an optically active form thereof, a salt thereof and a hydrate thereof, OM99-2 (WO01/00663)), γ secretase inhibitor, β amyloid protein aggregation inhibitor (e.g., PTI-00703, ALZHEMED (NC-531), PPI-368 (National Publication of International Patent Application No. 11-514333), PPI-558 (National Publication of International Patent Application No. 2001-500852), SKF-74652 (Biochem. J. (1999), 340(1), 283-289)), β amyloid vaccine, β amyloid-degrading enzyme and the like, brain function enhancer (e.g., aniracetam, nicergoline), therapeutic drug for Parkinson's disease [(e.g., dopamine receptor agonist (e.g., L-DOPA, bromocriptine, pergolide, talipexole, pramipexole, cabergoline, amantadine), monoamine oxidase enzyme (MAO) inhibitor (e.g., deprenyl, selegiline, remacemide, riluzole), anticholinergic agent (e.g., trihexyphenidyl, biperiden), COMT inhibitor (e.g., entacapone)], therapeutic drug for amyotrophic lateral sclerosis (e.g., riluzole etc., neurotrophic factor), therapeutic drug for abnormal behavior accompanying progress of dementia, wandering and the like (e.g., sedative, anti-anxiety drug), apoptosis inhibitor (e.g., CPI-1189, IDN-6556, CEP-1347), neuronal differentiation-regenerate promoter (e.g., leteprinim, xaliproden; SR-57746-A), SB-216763, Y-128, VX-853, prosaptide, 5,6-dimethoxy-2-[2,2,4,6,7-pentamethyl-3-(4-methylphenyl)-2,3-dihydro-1-benzofuran-5-yl]isoindoline, 5,6-dimethoxy-2-[3-(4-isopropylphenyl)-2,2,4,6,7-pentamethyl-2,3-dihydro-1-benzofuran-5-yl]isoindoline, 6-[3-(4-isopropylphenyl)-2,2,4,6,7-pentamethyl-2,3-dihydro-1-benzofuran-5-yl]-6,7-dihydro-5H-[1,3]dioxolo[4,5-f]isoindole and an optically active form, salt or hydrate thereof), non-steroidal antiinflammatory agents (meloxicam, tenoxicam, indomethacin, ibuprofen, celecoxib, rofecoxib, aspirin, indomethacin etc.), steroid drug (dexamethasone, hexestrol, cortisone acetate etc.), disease-modifying anti-rheumatic drug (DMARDs), anti-cytokine drug (e.g., TNF inhibitor, MAP kinase inhibitor), therapeutic agent for incontinence, frequent urination (e.g., flavoxate hydrochloride, oxybutynin hydrochloride, propiverine hydrochloride), phosphodiesterase inhibitor (e.g., sildenafil(citrate)), dopamine agonist (e.g., apomorphine), antiarrhythmic drugs (e.g., mexiletine), sex hormone or a derivative thereof (e.g., progesterone, estradiol, estradiol benzoate), therapeutic agent for osteoporosis (e.g., alfacalcidol, calcitriol, elcatonin, calcitonin salmon, estriol, ipriflavone, pamidronate disodium, alendronate sodium hydrate, incadronate disodium), parathyroid hormone (PTH), calcium receptor antagonists, therapeutic drug for insomnia (e.g., benzodiazepines medicament, non-benzodiazepines medicament, melatonin agonist, orexin receptor antagonists), therapeutic drug for schizophrenia (e.g., typical antipsychotic agents such as haloperidol and the like; atypical antipsychotic agents such as clozapine, olanzapine, risperidone, aripiprazole and the like; medicament acting on metabotropic glutamate receptor or ion channel conjugated-type glutamate receptor; phosphodiesterase inhibitor), benzodiazepines medicament (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), mirtazapine, trazodone hydrochloride, nefazodone hydrochloride, bupropion hydrochloride, setiptiline maleate, $5\text{-}HT_{1A}$ agonist, (buspirone hydrochloride, tandospirone citrate, osemozotan hydrochloride etc.), $5\text{-}HT_{2A}$ antagonist, $5\text{-}HT_{2A}$ inverse agonist, $5\text{-}HT_{3}$ antagonist (cyamemazine etc.), heart non-selective β inhibitor (propranolol hydrochloride, oxprenolol hydrochloride etc.), histamine $H_1$ antagonist (hydroxyzine hydrochloride etc.), CRF antagonist, other antianxiety drug (meprobamate etc.), tachykinin antagonist (MK-869, saredutant etc.), medicament that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine moiety agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for spasm, therapeutic drug for fibromyalgia syndrome, therapeutic drug for headache, therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for lipid abnormality such as cholesterol-lowering drug (statin series (pravastatin sodium, atorvastatin, simvastatin, rosuvastatin etc.), fibrate (clofibrate etc.), squalene synthetase inhibitor), therapeutic drug for abnormal behavior or suppressant of dromomania due to dementia (sedatives, antianxiety drug etc.), therapeutic drug for diabetes, therapeutic agent for diabetic complications, therapeutic drug for hypertension, therapeutic drug for hypotension, diuretic, chemotherapeutic agent, immunotherapeutic agent, antithrombotic agent, anti-cancer agent and the like.

Two or more kinds of the above-mentioned concomitant drug may be used in a mixture at an appropriate ratio.

When the compound of the present invention is applied to each of the above-mentioned diseases, it can also be used in combination with biologics (e.g., antibody drug, nucleic acid or nucleic acid derivative, aptamer drug, vaccine preparation), or can be used in combination with a gene therapy method and the like, or can also be used in combination with a treatment in psychiatric field without using drugs.

Examples of the antibody drug and vaccine preparation include vaccine preparation against angiotensin II, vaccine preparation against CETP, CETP antibody, antibody against TNFα antibody and other cytokines, amyloid p vaccine preparation, vaccine for type 1 diabetes (e.g., DIAPEP-277 of Peptor), anti-HIV antibody and HIV vaccine preparation, as well as antibodies or vaccine preparations against cytokines, renin-angiotensin type enzymes and products thereof, antibodies or vaccine preparations against enzymes or proteins involved in blood lipid metabolism, antibodies or vaccines relating to enzymes and proteins involved in blood coagulation or fibrinolysis system, antibodies or vaccine preparations against proteins involved in sugar metabolism and insulin resistance, and the like. In addition, it can be used in combination with biologics relating to growth factors such as GH, IGF and the like.

Examples of the gene therapy method include a treatment method using gene relating to cytokine, renin-angiotensin type enzyme and product thereof, G protein, G protein conjugated receptor and phosphorylating enzyme thereof, a treatment method using a DNA decoy such as NFκB decoy and the like, a treatment method using antisense, a treatment method using a gene relating to an enzyme or protein involved in blood lipid metabolism (e.g., a gene relating to metabolism, excretion and absorption of cholesterol or triglyceride or HDL-cholesterol or blood phospholipid), a treatment method using a gene relating to an enzyme or protein involved in angiogenesis therapy for peripheral vascular obstruction and the like (e.g., growth factors such as HGF, VEGF etc.), a treatment method using a gene relating to a protein involved in glucose metabolism and insulin resistance, antisense against cytokines such as TNF etc., and the like.

Examples of the treatment method in the psychiatric field without using drug include modified electroconvulsive therapy, deep brain stimulation therapy, repetitive transcranial magnetic stimulation therapy, psychotherapy including cognitive behavioral therapy and the like.

The compound of the present invention can also be used in combination with various organ regeneration methods such as cardiac regeneration, renal regeneration, pancreatic regeneration, revascularization and the like, cell transplantation therapy utilizing bone marrow cells (bone marrow-derived mononuclear cell, myelogenic stem cell), or artificial organ utilizing tissue engineering (e.g., artificial blood vessel, cardiomyocyte sheet).

EXAMPLES

The present invention is explained in detail in the following by referring to Examples, Experimental Examples and Formulation Examples. However, the examples do not limit the present invention and the examples can be modified within the scope of the present invention.

The "room temperature" in the following Examples is generally about 10° C. to about 35° C. The ratio for mixed solvent is, unless otherwise specified, a volume mixing ratio and % means wt % unless otherwise specified.

The elution by column chromatography in the Examples was performed under the observation by TLC (Thin Layer Chromatography) unless otherwise specified. In the observation by TLC, 60 $F_{254}$ manufactured by Merck was used as a TLC plate, the solvent used as an elution solvent in column chromatography was used as an eluent, and UV detector was used for the detection. In silica gel column chromatography, the indication of NH means use of aminopropylsilane-bonded silica gel and the indication of DIOL means use of 3-(2,3-dihydroxypropoxy)propylsilane-bonded silica gel. In preparative HPLC (high performance liquid chromatography), the indication of C18 means use of octadecyl-bonded silica gel. The ratio for elution solvent is, unless otherwise specified, a volume mixing ratio.

$^1$H NMR was measured by Fourier transform NMR. For the analysis of $^1$H NMR, ACD/SpecManager (trade name) software and the like were used. Peaks of a hydroxyl group, an amino group and the like, having very mild proton peak, are not sometimes described.

MS was measured by LC/MS. As the ionization method, ESI method, or APCI method was used. The data indicates actual measured value (found). While molecular ion peak is generally observed, a fragment ion is sometimes observed. In the case of a salt, a molecular ion peak or fragment ion peak of free form is generally observed.

In the following Examples, the following abbreviations are used.

MS: mass spectrum
M: mol concentration
N: normality
$CDCl_3$: deuterochloroform
DMSO-$d_6$: deuterodimethyl sulfoxide
$^1$H NMR: proton nuclear magnetic resonance
LC/MS: liquid chromatograph mass spectrometer
ESI: electrospray ionization
APCI: atmospheric pressure chemical ionization
SFC: supercritical fluid chromatography
$Pd_2(dba)_3$: tris(dibenzylideneacetone)dipalladium(0)
TFA: trifluoroacetic acid
DIPEA: N,N-diisopropylethylamine
DMF: N,N-dimethylformamide
THF: tetrahydrofuran
$CH_3CN$: acetonitrile
DME: 1,2-dimethoxyethane
MeOH: methanol
EtOH: ethanol
$Pd(PPh_3)_4$: palladium-triphenylphosphine (1:4)
AcOH: acetic acid
TEA: triethylamine
$T_3P$: 2,4,6-tripropyl-1,3,5,2,4,6-trioxatriphosphinane 2,4,6-trioxide
HATU: O-(7-azabenzotriazol-1-yl)-N,N,N',N'-tetramethyluronium hexafluorophosphate
NBS: N-bromosuccinimide
NMP: N-methyl-2-pyrrolidone
LDA: lithium diisopropylamide
TBAF: tetrabutylammonium fluoride
Xantphos: 4,5-bis(diphenylphosphino)-9,9-dimethylxanthene
tBu: tert-butyl
Boc: tert-butoxycarbonyl

Example 1 rac-N-[(6S,7R)-2-methyl-7-({[(1s,4S)-4-phenylcyclohexyl]oxy}methyl)-4,5,6,7-tetrahydropyrazolo[1,5-a]pyridin-6-yl]methanesulfonamide

A) 3-bromo-2-({[(1s,4s)-4-phenylcyclohexyl]oxy}methyl)pyridine

To a mixture of (1s,4S)-4-phenylcyclohexan-1-ol (7.00 g) and THF (100 ml) was added 60% sodium hydride (2.38 g) little by little under nitrogen atmosphere at 0° C. The reaction mixture was stirred at 0° C. for 30 min, and 3-bromo-2-(bromomethyl)pyridine (12.0 g) was added thereto at 0° C. The mixture was stirred at 70° C. for 13.5 hr. To the mixture was added saturated aqueous ammonium chloride solution, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/petroleum ether) and preparative HPLC (column: Phenomenex Gemini C18, mobile phase: water/acetonitrile (containing 0.05% aqueous ammonia)) to give the title compound (8.80 g).

MS: [M+H]$^+$346.0

B) ethyl 6-bromo-2-methyl-7-({[(1s,4s)-4-phenylcyclohexyl]oxy}methyl)pyrazolo[1,5-a]pyridine-3-carboxylate To a mixture of 3-bromo-2-({[(1s,4s)-4-phenylcyclohexyl]oxy}methyl)pyridine (0.89 g) in dichloromethane (10 ml) was added dropwise ca. 0.47 M 2-[(aminooxy)sulfonyl]-1,3,5-trimethylbenzene dichloromethane solution (15 ml) prepared separately at 0° C. The mixture was stirred at 0° C. for 1 hr. The mixture was concentrated under reduced pressure, and the residue was dissolved in DMF (30 ml). To the mixture were added ethyl pent-2-ynoate (0.43 g) and potassium carbonate (1.07 g) at 20° C. The mixture was stirred at 20° C. for 12 hr. To the mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/petroleum ether) to give the title compound (0.23 g).

MS: [M+H]$^+$471.1

C) 6-bromo-2-methyl-7-({[(1s,4s)-4-phenylcyclohexyl]oxy}methyl)pyrazolo[1,5-a]pyridine-3-carboxylic acid A mixture of ethyl 6-bromo-2-methyl-7-({[(1s,4s)-4-phenylcyclohexyl]oxy}methyl)pyrazolo[1,5-a]pyridine-3-carboxylate (280 mg), sodium hydroxide (95.0 mg), EtOH (4 ml), THF (4 ml) and water (4 ml) was stirred at 80° C. for 3 hr. The reaction solution was concentrated under reduced pressure, and the residue was adjusted to pH 2-3 with 2M hydrochloric acid. The obtained solid was collected by filtration, washed with water, and dried to give the title compound (250 mg). MS: [M+H]$^+$443.0

D) 6-bromo-2-methyl-7-({[(1s,4s)-4-phenylcyclohexyl]oxy}methyl)pyrazolo[1,5-a]pyridine A mixture of 6-bromo-2-methyl-7-({[(1s,4s)-4-phenylcyclohexyl]oxy}methyl)pyrazolo[1,5-a]pyridine-3-carboxylic acid (190 mg), silver acetate (215 mg), potassium carbonate (178 mg) and NMP (8 ml) was stirred at 125° C. for 4 hr. To the reaction solution was added ethyl acetate, and the insoluble substance was removed by filtration. To the filtrate was added saturated brine, and the mixture was extracted with ethyl acetate. The organic layer was separated, washed with water, dried over anhydrous sodium sulfate, and concentrated under reduced pressure. The residue was purified by preparative TLC (ethyl acetate/petroleum ether) to give the title compound (132 mg).

MS: [M+H]$^+$399.1

E) N-[2-methyl-7-({[(1s,4s)-4-phenylcyclohexyl]oxy}methyl)pyrazolo[1,5-a]pyridin-6-yl]methanesulfonamide A mixture of 6-bromo-2-methyl-7-({[(1s,4s)-4-phenylcyclohexyl]oxy}methyl)pyrazolo[1,5-a]pyridine (132 mg), methanesulfonamide (47.2 mg), Pd$_2$(dba)$_3$ (30.3 mg), cesium carbonate (215 mg) and DME (8 ml) was stirred under nitrogen atmosphere at 85° C. for 4 hr. The reaction solution was filtered, the insoluble substance was washed with ethyl acetate, and the filtrate was concentrated under reduced pressure. The residue was purified by silica gel column chromatography (ethyl acetate/petroleum ether) to give the title compound (125 mg).

MS: [M+H]$^+$414.1

F) rac-N-[(6S,7R)-2-methyl-7-({[(1s,4S)-4-phenylcyclohexyl]oxy}methyl)-4,5,6,7-tetrahydropyrazolo[1,5-a]pyridin-6-yl]methanesulfonamide To a mixture of N-[2-methyl-7-({[(1s,4s)-4-phenylcyclohexyl]oxy}methyl)pyrazolo[1,5-a]pyridin-6-yl]methanesulfonamide (60.0 mg), MeOH (2.5 ml) and acetic acid (2.5 ml) was added platinum(IV) oxide (9.88 mg) under nitrogen atmosphere at 25° C. The mixture was degassed, and stirred under 3 MPa hydrogen pressure at 50° C. for 16 hr. The catalyst was removed by filtration, and the filtrate was concentrated under reduced pressure. The residue was purified by preparative TLC (ethyl acetate/petroleum ether) and preparative HPLC (column: Phenomenex Gemini, mobile phase: water/acetonitrile (containing 0.05% aqueous ammonia)) to give the title compound (19.0 mg).

$^1$H NMR (400 MHz, DMSO-d$_6$) δ 1.26-1.37 (3H, m), 1.40-1.64 (3H, m), 1.73-1.93 (3H, m), 2.08 (3H, s), 2.30-2.33 (1H, m), 2.40-2.43 (1H, m), 2.74-2.90 (2H, m), 3.02 (3H, s), 3.49-3.51 (1H, m), 3.80-3.82 (1H, m), 3.93-4.02 (2H, m), 4.29-4.31 (1H, m), 5.79 (1H, s), 7.09-7.19 (3H, m), 7.20-7.30 (2H, m), 7.44 (1H, brs).

Example 22 rac-N-{(7S,8S)-8-[([1,1'-biphenyl]-3-yl)methyl]-5,6,7,8-tetrahydroquinolin-7-yl}methanesulfonamide

A) 5,6-dihydroquinoline

A mixture of 5,6,7,8-tetrahydroquinolin-8-ol (2.00 g) and polyphosphoric acid (20.0 g) was stirred at 120° C. for 30 min. The reaction solution was poured into water at 0° C., adjusted to pH 10 with sodium hydroxide, and extracted with ethyl acetate. The organic layer was separated, washed with water and saturated brine, dried over anhydrous sodium sulfate, and concentrated under reduced pressure to give the title compound (1.36 g).

¹H NMR (400 MHz, CDCl₃) δ 2.31-2.41 (2H, m), 2.83 (2H, t, J=8.4 Hz), 6.28-6.35 (1H, m), 6.60-6.66 (1H, m), 7.00 (1H, dd, J=7.6, 5.2 Hz), 7.35 (1H, dd, J=7.2, 0.4 Hz), 8.34 (1H, dd, J=4.8, 0.8 Hz).

B) 7-bromo-5,6,7,8-tetrahydroquinolin-8-yl acetate

To a mixture of N-bromoacetamide (1.43 g), lithium acetate (1.70 g) and acetic acid (20 ml) was added 5,6-dihydroquinoline (1.36 g) at 0° C. The mixture was stirred at 10-20° C. for 13 hr, and concentrated under reduced pressure. The residue was poured into 2 M aqueous sodium carbonate solution, and the mixture was extracted with ethyl acetate. The organic layer was concentrated under reduced pressure, and the residue was purified by silica gel column chromatography (ethyl acetate/petroleum ether) to give the title compound (2 g).
¹H NMR (400 MHz, CDCl₃) δ 2.12 (3H, s), 2.20-2.32 (1H, m), 2.38-2.50 (1H, m), 2.83-2.95 (1H, m), 3.07-3.19 (1H, m), 4.06-4.15 (1H, m), 6.10 (1H, d, J=4.0 Hz), 7.22 (1H, dd, J=7.6, 4.4 Hz), 7.50 (1H, d, J=7.6 Hz), 8.53 (1H, dd, J=4.8, 0.8 Hz).

C) 1a,2,3,7b-tetrahydrooxireno[h]quinoline

To a mixture of 7-bromo-5,6,7,8-tetrahydroquinolin-8-yl acetate (2.00 g) and THF (20 ml) was added sodium methanolate (2.00 g), and the mixture was stirred under nitrogen atmosphere at 15° C. for 5 hr. The mixture was poured into water, and extracted with dichloromethane. The organic layer was separated, washed with water and saturated brine, dried over anhydrous sodium sulfate, and concentrated under reduced pressure to give the title compound (1.00 g).
1H NMR (400 MHz, CDCl₃) δ 1.70-1.81 (1H, m), 2.41-2.59 (2H, m), 2.75-2.88 (1H, m), 3.79 (1H, t, J=3.6 Hz), 4.07 (1H, d, J=4.4 Hz), 7.18 (1H, dd, J=7.6, 5.2 Hz), 7.38 (1H, d, J=7.6 Hz), 8.38-8.45 (1H, m).

D) rac-(7R,8R)-8-[([1,1T-biphenyl]-3-yl)methyl]-5,6,7,8-tetrahydroquinolin-7-ol

To a mixture of magnesium (132 mg) and diethyl ether (5 ml) was added 1,2-dibromoethane (102 mg). To the reaction solution was added a mixture of 3-(bromomethyl)biphenyl (1.34 g) and diethyl ether (20 ml) at 25° C., and the mixture was stirred at 25° C. for 2 hr. To the obtained reaction solution was added dropwise a solution of 1a,2,3,7b-tetrahydrooxireno[h]quinoline (400 mg) in THF (8 ml) under nitrogen atmosphere at −78° C. The mixture was stirred under nitrogen atmosphere at −78° C. for 1 hr, and then at 25° C. for 16 hr. To the mixture was added saturated aqueous ammonium chloride solution, and the mixture was extracted with ethyl acetate. The organic layer was separated, dried over anhydrous sodium sulfate, and concentrated under reduced pressure. The residue was purified by silica gel column chromatography (ethyl acetate/petroleum ether) to give the title compound (351 mg).
MS: [M+H]⁺316.0.

E) rac-(7R,8R)-8-[([1,1'-biphenyl]-3-yl)methyl]-5,6,7,8-tetrahydroquinolin-7-yl methanesulfonate To a mixture of rac-(7R,8R)-8-[([1,1'-biphenyl]-3-yl)methyl]-5,6,7,8-tetrahydroquinolin-7-ol (380 mg), TEA (244 mg) and dichloromethane (5 ml) was added dropwise methanesulfonyl chloride (166 mg) at 0° C. The mixture was stirred under nitrogen atmosphere at 0° C. for 1 hr. The reaction solution was concentrated under reduced pressure, and the residue was purified by silica gel column chromatography (ethyl acetate/petroleum ether) to give the title compound (251 mg).
MS: [M+H]⁺394.0.

F) rac-(7S,8S)-7-azido-8-[([1,1'-biphenyl]-3-yl)methyl]-5,6,7,8-tetrahydroquinoline To a mixture of rac-(7R,8R)-8-[([1,1'-biphenyl]-3-yl)methyl]-5,6,7,8-tetrahydroquinolin-7-yl methanesulfonate (251 mg) and DMF (5 ml) was added sodium azide (207 mg) at 25° C. The mixture was stirred at 100° C. for 15 hr. The mixture was poured into water, and extracted with ethyl acetate. The organic layer was separated, washed with water, dried over anhydrous sodium sulfate, and concentrated under reduced pressure to give the title compound (198 mg).
MS: [M+H]⁺341.1.

G) rac-(7S,8S)-8-[([1,1'-biphenyl]-3-yl)methyl]-5,6,7,8-tetrahydroquinolin-7-amine To a mixture of rac-(7S,8S)-7-azido-8-[([1,1'-biphenyl]-3-yl)methyl]-5,6,7,8-tetrahydroquinoline (198 mg) and MeOH (8 ml) was added 10% palladium on carbon (20 mg). The mixture was degassed, and stirred under hydrogen atmosphere at 25° C. for 3 hr. The catalyst was removed by filtration, and washed with MeOH, and the filtrate was concentrated under reduced pressure. The residue was purified by preparative TLC (ethyl acetate/petroleum ether) to give the title compound (20 mg).
MS: [M+H]⁺315.0.

H) rac-N-{(7S,8S)-8-[([1,1'-biphenyl]-3-yl)methyl]-5,6,7,8-tetrahydroquinolin-7-yl}methanesulfonamide To a mixture of rac-(7S,8S)-8-[([1,1'-biphenyl]-3-yl)methyl]-5,6,7,8-tetrahydroquinolin-7-amine (20 mg) and dichloromethane (2 ml) was added methanesulfonyl chloride (9 mg) at 0° C. The mixture was stirred at 0° C. for 1 hr, and concentrated under reduced pressure. The residue was purified by HPLC (mobile phase: water/acetonitrile (containing 0.225% formic acid)) to give the title compound (2 mg).
¹H NMR (400 MHz, CDCl₃) δ 1.89-2.01 (1H, m), 2.17-2.31 (1H, m), 2.74 (3H, s), 2.83-2.96 (2H, m), 2.97-3.12 (1H, m), 3.50-3.65 (1H, m), 3.83-3.96 (2H, m), 4.16 (1H, d, J=8.4 Hz), 7.13-7.19 (1H, m), 7.28-7.52 (8H, m) 7.58 (2H, d, J=7.2 Hz), 8.49 (1H, d, J=4.8 Hz).

Example 24 rel-N-[(6S,7R)-7-({[1-(5-fluoropyrimidin-2-yl)piperidin-4-yl]oxy}methyl)-2-(propan-2-yl)-4,5,6,7-tetrahydropyrazolo[1,5-a]pyridin-6-yl]methanesulfonamide with shorter retention time A) tert-butyl 4-[(3-bromopyridin-2-yl)methoxy]piperidine-1-carboxylate To a mixture of 60% sodium hydride (3.19 g) and THF (100 ml) was added tert-butyl 4-hydroxypiperidine-1-carboxylate (10.4 g) little by little at 0° C. The reaction mixture was stirred at room temperature for 1.5 hr, and cooled again to 0° C., and 3-bromo-2-(bromomethyl)pyridine (10.0 g) was added thereto. The mixture was stirred at room temperature for 15 hr. The mixture was poured into ice water, and extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (13.8 g).

MS: [M+H]$^+$371.2.

B) tert-butyl 4-({3-[(methanesulfonyl)amino]pyridin-2-yl}methoxy)piperidine-1-carboxylate A mixture of tert-butyl 4-[(3-bromopyridin-2-yl)methoxy]piperidine-1-carboxylate (2.4 g), methanesulfonamide (0.738 g), di-tert-butyl(2',4',6'-triisopropylbiphenyl-2-yl)phosphine (0.275 g), Pd$_2$(dba)$_3$ (0.296 g), cesium carbonate (3.16 g) and THF (18 mL) was irradiated with microwave at 120° C. for 1 hr. To the mixture was added saturated brine, and the mixture was extracted with ethyl acetate/THF. The organic layer was separated, dried over anhydrous magnesium sulfate, and concentrated under reduced pressure. The residue was purified by silica gel column chromatography (NH, NeOH/ethyl acetate/hexane) to give the title compound (2.36 g).

MS: [M+H]$^+$386.3.

C) tert-butyl 4-({6-bromo-3-[(methanesulfonyl)amino]pyridin-2-yl}methoxy)piperidine-1-carboxylate To a mixture of tert-butyl 4-({3-[(methanesulfonyl)amino]pyridin-2-yl}methoxy)piperidine-1-carboxylate (4.40 g) and CH$_3$CN (80 ml) was added NES (2.44 g) little by little under nitrogen atmosphere at 20° C. The mixture was stirred at 20° C. for 2 hr. The reaction solution was concentrated under reduced pressure, and the residue was purified by silica gel column chromatography (ethyl acetate/petroleum ether) to give the title compound (4.17 g).

MS: [M+Na]$^+$486.1.

D) tert-butyl 4-({3-[(methanesulfonyl)amino]-6-(3-methylbut-1-yn-1-yl)pyridin-2-yl}methoxy)piperidine-1-carboxylate A mixture of tert-butyl 4-({6-bromo-3-[(methanesulfonyl)amino]pyridin-2-yl}methoxy)piperidine-1-carboxylate (1.50 g), 3-methylbut-1-yne (0.66 g), Pd(PPh$_3$)$_4$ (0.37 g), copper(I) iodide (0.18 g), TEA (0.65 g) and THF (25 ml) was stirred under nitrogen atmosphere at 20° C. for 24 hr. To the reaction solution was added saturated brine, and the insoluble substance was removed by filtration, and the filtrate was extracted with ethyl acetate. The organic layer was separated, washed with saturated brine, dried over anhydrous sodium sulfate, and concentrated under reduced pressure. The residue was purified by silica gel column chromatography (ethyl acetate/petroleum ether) to give the title compound (1.25 g).

MS: [M+H]$^+$452.2.

E) tert-butyl 4-({6-[(methanesulfonyl)amino]-2-(propan-2-yl)pyrazolo[1,5-a]pyridin-7-yl}methoxy)piperidine-1-carboxylate To a mixture of tert-butyl 4-({3-[(methanesulfonyl)amino]-6-(3-methylbut-1-yn-1-yl)pyridin-2-yl}methoxy)piperidine-1-carboxylate (650 mg) and dichloromethane (8 ml) was added 2-[(aminooxy)sulfonyl]-1,3,5-trimethylbenzene (620 mg) with a syringe at 0° C. The mixture was stirred at 0° C. for 1 hr, warmed to 20° C., and stirred for 2 hr. The reaction solution was concentrated under reduced pressure, and the residue was dissolved in DMF (8 ml). To the mixture was added potassium carbonate (398 mg) at 20° C. The reaction mixture was stirred at 20° C. for 15 hr, and TEA (728 mg) and Boc$_2$O (942 mg) were added thereto with a syringe at 20° C. The mixture was stirred at 20° C. for 15 hr. To the mixture was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/petroleum ether) to give the title compound (150 mg).

MS: [M+H]$^+$467.2.

F) rac-tert-butyl 4-{[(6S,7R)-6-[(methanesulfonyl)amino]-2-(propan-2-yl)-4,5,6,7-tetrahydropyrazolo[1,5-a]pyridin-7-yl]methoxy}piperidine-1-carboxylate To a mixture of tert-butyl 4-({6-[(methanesulfonyl)amino]-2-(propan-2-yl)pyrazolo[1,5-a]pyridin-7-yl}methoxy)piperidine-1-carboxylate (150 mg), NeOH (2 ml) and acetic acid (2 ml) was added platinum(IV) oxide (67.9 mg) under nitrogen atmosphere at 20° C. The reaction solution was degassed, and stirred under 3.5 Mpa hydrogen pressure at 70° C. for 16 hr. The catalyst was removed by filtration, and the insoluble substance was washed with MeOH, and the filtrate was concentrated under reduced pressure. To the mixture was added saturated aqueous sodium hydrogencarbonate solution, and the mixture was extracted with ethyl acetate. The organic layer was separated, washed with saturated brine, dried over anhydrous sodium sulfate, and concentrated under reduced pressure. The residue was purified by HPLC (mobile phase: water/acetonitrile (5 mM containing ammonium bicarbonate)) to give the title compound (40.6 mg).

MS: [M+H]$^+$471.3.

G) rac-N-[(6S,7R)-7-{[(piperidin-4-yl)oxy]methyl}-2-(propan-2-yl)-4,5,6,7-tetrahydropyrazolo[1,5-a]pyridin-6-yl]methanesulfonamide hydrochloride To a mixture of rac-tert-butyl 4-{[(6S,7R)-6-[(methanesulfonyl)amino]-2-(propan-2-yl)-4,5,6,7-tetrahydropyrazolo[1,5-a]pyridin-7-yl]methoxy}piperidine-1-carboxylate (70.0 mg) and ethyl acetate (3 ml) was added 4 M hydrogen chloride/ethyl acetate solution (3.00 ml) at 20° C. The mixture was stirred at 20° C. for 2 hr. The reaction solution was concentrated under reduced pressure to give the title compound (60.0 mg).

MS: [M+H]$^+$371.2.

H) rac-N-[(6S,7R)-7-({[1-(5-fluoropyrimidin-2-yl)piperidin-4-yl]oxy}methyl)-2-(propan-2-yl)-4,5,6,7-tetrahydropyrazolo[1,5-a]pyridin-6-yl]methanesulfonamide A mixture of rac-N-[(6S,7R)-7-{[(piperidin-4-yl)oxy]methyl}-2-(propan-2-yl)-4,5,6,7-tetrahydropyrazolo[1,5-a]pyridin-6-yl]methanesulfonamide hydrochloride (60.0 mg), 2-chloro-5-fluoropyrimidine (39.1 mg), potassium carbonate (61.1 mg) and DMF (2 ml) was stirred under nitrogen atmosphere at 110° C. for 16 hr. The reaction solution was filtered, and the insoluble substance was washed with MeOH, and the filtrate was concentrated under reduced pressure. The residue was purified by HPLC (column: Xtimate C18, mobile phase: water/acetonitrile (containing 0.05% aqueous ammonia)) to give the title compound (26.9 mg).

MS: [M+H]$^+$467.2.

I) rel-N-[(6S,7R)-7-({[1-(5-fluoropyrimidin-2-yl) piperidin-4-yl]oxy}methyl)-2-(propan-2-yl)-4,5,6,7-tetrahydropyrazolo[1,5-a]pyridin-6-yl]methanesulfonamide with shorter retention time rac-N-[(6S,7R)-7-({[1-(5-Fluoropyrimidin-2-yl)piperidin-4-yl]oxy}methyl)-2-(propan-2-yl)-4,5,6,7-tetrahydropyrazolo[1,5-a]pyridin-6-yl]methanesulfonamide (850 mg) was resolved by SFC ((column: CHIRALPAK OJ-H, 30 mmID×250 mmL, manufactured by Daicel Chemical Industries, mobile phase: carbon dioxide/MeOH (containing 0.1% aqueous ammonia)) to give the title compound with shorter retention time (193 mg).

$^1$H NMR (400 MHz, CDCl$_3$) δ 1.20-1.26 (6H, m), 1.43-1.53 (1H, m), 1.54-1.64 (1H, m), 1.76-1.84 (1H, m), 1.88-1.98 (1H, m), 2.02-2.11 (1H, m), 2.20-2.32 (1H, m), 2.78-2.86 (1H, m), 2.88-2.99 (2H, m), 3.03 (3H, s), 3.33-3.47 (2H, m), 3.56-3.64 (1H, m), 3.95-4.03 (1H, m), 4.07-4.16 (3H, m), 4.18-4.23 (1H, m), 4.48-4.54 (1H, m), 5.66 (1H, d, J=7.6 Hz), 5.81 (1H, s), 8.17 (2H, s).

Example 33 rel-N-[(6S,7R)-2-ethyl-7-({[1-(5-fluoropyrimidin-2-yl)piperidin-4-yl]oxy}methyl)-4,5,6,7-tetrahydropyrazolo[1,5-a]pyridin-6-yl]methanesulfonamide with longer retention time A) tert-butyl 4-({6-(but-1-yn-1-yl)-3-[(methanesulfonyl)amino]pyridin-2-yl}methoxy)piperidine-1-carboxylate A mixture of tert-butyl 4-({6-bromo-3-[(methanesulfonyl)amino]pyridin-2-yl}methoxy)piperidine-1-carboxylate (500 mg), (but-1-yn-1-yl)(trimethyl)silane (680 mg), Pd(PPh$_3$)$_4$ (124 mg), copper(I) iodide (61.5 mg), 1 M TBAF THF solution (5.38 ml) and diisopropylamine (10 ml) was stirred in a sealed tube under nitrogen atmosphere at 70° C. for 16 hr. To the reaction solution was added ethyl acetate, and the mixture was washed with water and saturated brine, dried over anhydrous sodium sulfate, and concentrated under reduced pressure. The residue was purified by silica gel column chromatography (ethyl acetate/petroleum ether) to give the title compound (100 mg).

MS: [M+H]$^+$438.1.

B) tert-butyl 4-({2-ethyl-6-[(methanesulfonyl) amino]pyrazolo[1,5-a]pyridin-7-yl}methoxy)piperidine-1-carboxylate To a mixture of tert-butyl 4-({6-(but-1-yn-1-yl)-3-[(methanesulfonyl)amino]pyridin-2-yl}methoxy)piperidine-1-carboxylate (100 mg) and dichloromethane (3 ml) was added 2-[(aminooxy)sulfonyl]-1,3,5-trimethylbenzene (98.4 mg) with a syringe at 0° C. The mixture was stirred at 0° C. for 1 hr, warmed to 20° C., and stirred for 2 hr. The reaction solution was concentrated under reduced pressure, and the residue was dissolved in DMF (3 ml). To the mixture was added potassium carbonate (63.2 mg) at 20° C. The reaction mixture was stirred at 20° C. for 15 hr. To the mixture was added water, and the mixture was extracted with ethyl acetate. The organic layer was separated, washed with saturated brine, dried over anhydrous sodium sulfate, and concentrated under reduced pressure. The residue was purified by preparative TLC (ethyl acetate/petroleum ether) to give the title compound (35.0 mg).

MS: [M+H]$^+$453.1.

C) rac-tert-butyl 4-({(6S,7R)-2-ethyl-6-[(methanesulfonyl)amino]-4,5,6,7-tetrahydropyrazolo[1,5-a] pyridin-7-yl}methoxy)piperidine-1-carboxylate To a mixture of tert-butyl 4-({2-ethyl-6-[(methanesulfonyl)amino]pyrazolo[1,5-a]pyridin-7-yl}methoxy)piperidine-1-carboxylate (70.0 mg), MeOH (1 ml) and acetic acid (1 ml) was added platinum(IV) oxide (32.7 mg) under nitrogen atmosphere at 20° C. The reaction solution was degassed, and stirred under 3.5 Mpa hydrogen pressure at 70° C. for 48 hr. The catalyst was removed by filtration, and the insoluble substance was washed with MeOH, and the filtrate was concentrated under reduced pressure. To the mixture was added saturated aqueous sodium hydrogencarbonate solution, and the mixture was extracted with ethyl acetate. The organic layer was separated, washed with saturated brine, dried over anhydrous sodium sulfate, and concentrated under reduced pressure. The residue was purified by HPLC (mobile phase: water/acetonitrile (containing ammonium bicarbonate)) to give the title compound (40.0 mg).

MS: [M+H]$^+$457.3.

D) rac-N-[(6S,7R)-2-ethyl-7-{[(piperidin-4-yl)oxy] methyl}-4,5,6,7-tetrahydropyrazolo[1,5-a]pyridin-6-yl]methanesulfonamide hydrochloride To a mixture of rac-tert-butyl 4-({(6S,7R)-2-ethyl-6-[(methanesulfonyl)amino]-4,5,6,7-tetrahydropyrazolo[1,5-a]pyridin-7-yl}methoxy)piperidine-1-carboxylate (40.0 mg) and ethyl acetate (2 ml) was added 4 M hydrogen chloride/ethyl acetate solution (2.00 ml) with a syringe at 20° C. The mixture was stirred at 20° C. for 2 hr. The reaction solution was concentrated under reduced pressure to give the title compound (34.0 mg).

MS: [M+H]$^+$357.1.

E) rac-N-[(6S,7R)-2-ethyl-7-({[1-(5-fluoropyrimidin-2-yl)piperidin-4-yl]oxy}methyl)-4,5,6,7-tetrahydropyrazolo[1,5-a]pyridin-6-yl]methanesulfonamide A mixture of rac-N-[(6S,7R)-2-ethyl-7-{[(piperidin-4-yl)oxy]methyl}-4,5,6,7-tetrahydropyrazolo[1,5-a]pyridin-6-yl]methanesulfonamide hydrochloride (34.0 mg), 2-chloro-5-fluoropyrimidine (25.3 mg), potassium carbonate (39.6 mg) and DMF (2 ml) was stirred under nitrogen atmosphere at 110° C. for 16 hr. The reaction solution was filtered, and the insoluble substance was washed with MeOH, and the filtrate was concentrated under reduced pressure. The residue was purified by HPLC (mobile phase: water/acetonitrile (containing 0.05% aqueous ammonia)) to give the title compound (9.92 mg).

MS: [M+H]$^+$453.2.

F) rel-N-[(6S,7R)-2-ethyl-7-({[1-(5-fluoropyrimidin-2-yl)piperidin-4-yl]oxy}methyl)-4,5,6,7-tetrahydropyrazolo[1,5-a]pyridin-6-yl]methanesulfonamide with longer retention time rac-N-[(6S,7R)-2-Ethyl-7-({[1-(5-fluoropyrimidin-2-yl) piperidin-4-yl]oxy}methyl)-4,5,6,7-tetrahydropyrazolo[1,5- a]pyridin-6-yl]methanesulfonamide (490 mg) was resolved by SFC ((column: CHIRALPAK AD-H, 30 mmID×250 mmL, manufactured by Daicel Chemical Industries, mobile phase: MeOH (containing 0.1% aqueous ammonia)) to give the title compound (219 mg).

$^1$H NMR (400 MHz, DMSO-$d_6$) δ 1.11 (3H, t, J=7.6 Hz), 1.24-1.36 (1H, m), 1.39-1.51 (1H, m), 1.55-1.70 (1H, m), 1.71-1.91 (2H, m), 2.13-2.28 (1H, m), 2.44-2.48 (2H, m), 2.72-2.90 (2H, m), 2.98 (3H, s), 3.36-3.52 (3H, m), 3.65-3.75 (1H, m), 3.79-3.90 (2H, m), 3.92-4.00 (1H, m), 4.07-4.15 (1H, m), 4.21-4.31 (1H, m), 5.79 (1H, s), 7.42 (1H, brs), 8.40 (2H, s).

Example 56 rel-N-[(6S,7R)-2-(propan-2-yl)-7-({[1-(pyrimidin-2-yl)piperidin-4-yl]oxy}methyl)-4,5,6,7-tetrahydropyrazolo[1,5-a]pyridin-6-yl]methanesulfonamide with longer retention time A) rac-N-[(6S,7R)-2-(propan-2-yl)-7-({[1-(pyrimidin-2-yl)piperidin-4-yl]oxy}methyl)-4,5,6,7-tetrahydropyrazolo[1,5-a]pyridin-6-yl]methanesulfonamide A mixture of rac-N-[(6S,7R)-7-{[(piperidin-4-yl)oxy]methyl}-2-(propan-2-yl)-4,5,6,7-tetrahydropyrazolo[1,5-a]pyridin-6-yl]methanesulfonamide (200 mg), 2-chloropyrimidine (124 mg), DIPEA (279 mg) and DMSO (1 ml) was stirred at 100° C. for 3 hr. To the mixture was added water, and the mixture was extracted with ethyl acetate. The organic layer was separated, and concentrated under reduced pressure. The residue was purified by silica gel column chromatography (ethyl acetate) to give the title compound (189 mg).

MS: [M+H]$^+$449.2.

B) rel-N-[(6S,7R)-2-(propan-2-yl)-7-({[1-(pyrimidin-2-yl)piperidin-4-yl]oxy}methyl)-4,5,6,7-tetrahydropyrazolo[1,5-a]pyridin-6-yl]methanesulfonamide with longer retention time rac-N-[(6S,7R)-2-(Propan-2-yl)-7-({[1-(pyrimidin-2-yl)piperidin-4-yl]oxy}methyl)-4,5,6,7-tetrahydropyrazolo[1,5-a]pyridin-6-yl]methanesulfonamide (189 mg) was resolved by HPLC ((column: CHIRALPAK ID, 50 mmID×500 mmL, manufactured by Daicel Chemical Industries, mobile phase: hexane/EtOH/diethylamine=650/350/1) to give the title compound (81.0 mg).

$^1$H NMR (300 MHz, CDCl$_3$) δ 1.22 (6H, dd, J=6.8, 0.8 Hz), 1.39-1.67 (2H, m), 1.75-2.13 (3H, m), 2.18-2.34 (1H, m), 2.74-2.98 (3H, m), 3.02 (3H, s), 3.33-3.51 (2H, m), 3.55-3.67 (1H, m), 4.01-4.25 (5H, m), 4.50 (1H, ddd, J=6.9, 5.0, 3.2 Hz), 5.63 (1H, d, J=8.0 Hz), 5.80 (1H, s), 6.45 (1H, t, J=4.7 Hz), 8.28 (2H, d, J=4.9 Hz).

Example 63

(2S)—N-[(7S*,8S*)-8-({[1-(5-fluoropyrimidin-2-yl)piperidin-4-yl]oxy}methyl)-2-methyl-5,6,7,8-tetrahydroimidazo[1,2-a]pyridin-7-yl]oxolane-2-carboxamide with shorter retention time A) ethyl 4-bromo-2-fluoropyridine-3-carboxylate To a mixture of 4-bromo-2-fluoropyridine (16.0 g) and THF (200 ml) was added dropwise 2 M LDA THF solution (59.1 ml). The mixture was stirred at −78° C. for 30 min, and to the reaction solution was added ethyl carbonochloridate (11.8 g) at −78° C. The mixture was stirred at 25° C. for 1 hr. To the reaction solution was added water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/petroleum ether) to give the title compound (21.0 g).

MS: [M+H]$^+$248.0.

B) ethyl 2-amino-4-bromopyridine-3-carboxylate

A mixture of ethyl 4-bromo-2-fluoropyridine-3-carboxylate (21.0 g), aqueous ammonia (20 ml) and DMSO (40 ml) was degassed, the atmosphere was replaced with argon atmosphere, and the mixture was stirred under nitrogen atmosphere at 100° C. for 3 hr. To the reaction solution was added water, and the resulting solid was collected by filtration, and dried to give the title compound (16.0 g).

$^1$H NMR (400 MHz, DMSO-$d_6$) δ 1.30 (3H, t, J=7.2 Hz), 4.27-4.36 (2H, m), 6.52 (2H, s), 6.83 (1H, d, J=5.2 Hz), 7.87 (1H, d, J=5.2 Hz).

C) ethyl 7-bromo-2-methylimidazo[1,2-a]pyridine-8-carboxylate

A mixture of ethyl 2-amino-4-bromopyridine-3-carboxylate (12.0 g), 1-bromopropan-2-one (13.4 g), EtOH (50 ml) and dioxane (50 ml) was stirred at 90° C. for 12 hr. To the reaction solution was added TEA (14.9 g), and the mixture was stirred at 90° C. for 1 hr. The mixture was concentrated under reduced pressure, and the residue was purified by silica gel column chromatography (ethyl acetate/petroleum ether) to give the title compound (11.0 g).

MS: [M+H]$^+$283.0.

D) (7-bromo-2-methylimidazo[1,2-a]pyridin-8-yl)methanol

To a mixture of ethyl 7-bromo-2-methylimidazo[1,2-a]pyridine-8-carboxylate (6.00 g), calcium chloride (3.53 g), THF (50 ml) and MeOH (10 ml) was added sodium tetrahydroborate (1.60 g). The mixture was stirred under nitrogen atmosphere at 25° C. for 1 hr. To the reaction solution was added MeOH, the mixture was filtered, and the filtrate was concentrated under reduced pressure. To the residue was added water, and the mixture was adjusted to pH 10 with saturated aqueous sodium carbonate solution, and extracted with dichloromethane/MeOH. The organic layer was separated, washed with saturated brine, dried over anhydrous sodium sulfate, and concentrated under reduced pressure to give the title compound (4.30 g).

MS: [M+H]$^+$241.0.

E) 7-bromo-8-(chloromethyl)-2-methylimidazo[1,2-a]pyridine

To a mixture of (7-bromo-2-methylimidazo[1,2-a]pyridin-8-yl)methanol (4.30 g) and dichloromethane (40 ml) was added thionyl chloride (21.2 g). The mixture was stirred at 25° C. for 12 hr, and concentrated under reduced pressure. To the residue was added water, and the mixture was adjusted to pH 10 with saturated aqueous sodium carbonate solution, and extracted with ethyl acetate. The organic layer was separated, washed with saturated brine, dried over anhydrous sodium sulfate, and concentrated under reduced pressure. The residue was purified by silica gel column chromatography (ethyl acetate/petroleum ether) to give the title compound (4.10 g). MS, found: 260.9.

F) tert-butyl 4-[(7-bromo-2-methylimidazo[1,2-a]pyridin-8-yl)methoxy]piperidine-1-carboxylate To a mixture of tert-butyl 4-hydroxypiperidine-1-carboxylate (9.31 g) and THF (40 ml) was added sodium hydride (1.66 g) under nitrogen atmosphere at 0° C. 60%. The mixture was stirred at 0° C. for 1 hr, and to the reaction solution was added a solution of 7-bromo-8-(chloromethyl)-2-methylimidazo[1,2-a]pyridine (6.00 g) in THF (30 ml) under nitrogen atmosphere at 0° C. The mixture was stirred under nitrogen atmosphere at 25° C. for 1 hr. To the reaction solution was added water, and the mixture was extracted with ethyl acetate. The organic layer was separated, dried over anhydrous sodium sulfate, and concentrated under reduced pressure. The residue was purified by silica gel column chromatography (ethyl acetate/petroleum ether) to give the title compound (7.35 g).

MS: $[M+H]^+$424.1.

G) tert-butyl 4-({7-[(diphenylmethylidene)amino]-2-methylimidazo[1,2-a]pyridin-8-yl}methoxy)piperidine-1-carboxylate A mixture of tert-butyl 4-[(7-bromo-2-methylimidazo[1,2-a]pyridin-8-yl)methoxy]piperidine-1-carboxylate (3.00 g), diphenylmethanimine (1.92 g), cesium carbonate (4.61 g), $Pd_2(dba)_3$ (647 mg), Xantphos (818 mg) and dioxane (30 ml) was degassed, the atmosphere was replaced with argon atmosphere, and the mixture was stirred under nitrogen atmosphere at 90° C. for 3 hr. The reaction solution was filtered, and the filtrate was concentrated under reduced pressure. The residue was purified by silica gel column chromatography (dichloromethane/MeOH) to give the title compound (2.70 g).

MS: $[M+H]^+$525.2.

H) tert-butyl 4-[(7-amino-2-methylimidazo[1,2-a]pyridin-8-yl)methoxy]piperidine-1-carboxylate To a mixture of tert-butyl 4-({7-[(diphenylmethylidene)amino]-2-methylimidazo[1,2-a]pyridin-8-yl}methoxy)piperidine-1-carboxylate (20.9 g), $CH_3CN$ (2000 ml) and water (300 ml) was added TFA (11.4 g). The mixture was stirred at 25° C. for 12 hr. The reaction solution was adjusted to pH 7 with saturated aqueous sodium hydrogencarbonate solution, and the $CH_3CN$ was evaporated under reduced pressure. The residue was extracted with ethyl acetate, and the organic layer was washed with saturated brine, dried over anhydrous sodium sulfate, and concentrated under reduced pressure. The residue was purified by silica gel column chromatography (dichloromethane/MeOH) to give the title compound (12.5 g).

MS: $[M+H]^+$361.2.

I) tert-butyl 4-[(2-methyl-7-([(2S)-oxolane-2-carbonyl]amino}imidazo[1,2-a]pyridin-8-yl)methoxy]piperidine-1-carboxylate To a mixture of tert-butyl 4-[(7-amino-2-methylimidazo[1,2-a]pyridin-8-yl)methoxy]piperidine-1-carboxylate (4.00 g), (2S)-oxolane-2-carboxylic acid (3.87 g), TEA (11.2 g) and ethyl acetate (100 ml) was added 50% $T_3P$ ethyl acetate solution (21.2 g). The mixture was stirred at 25° C. for 12 hr. To the reaction solution was added water, and the mixture was extracted with ethyl acetate. The organic layer was separated, washed with saturated aqueous ammonium chloride solution, dried over anhydrous sodium sulfate, and concentrated under reduced pressure. The residue was purified by silica gel column chromatography (ethyl acetate/petroleum ether) to give the title compound (2.42 g).

MS: $[M+H]^+$459.4.

J) tert-butyl 4-{[(7SR,8SR)-2-methyl-7-{[(2S)-oxolane-2-carbonyl]amino}-5,6,7,8-tetrahydroimidazo[1,2-a]pyridin-8-yl]methoxy}piperidine-1-carboxylate To a mixture of tert-butyl 4-[(2-methyl-7-{[(2S)-oxolane-2-carbonyl]amino}imidazo[1,2-a]pyridin-8-yl)methoxy]piperidine-1-carboxylate (1.90 g) and EtOH (50 ml) was added platinum(IV) oxide (376 mg) under nitrogen atmosphere. The reaction solution was degassed, the atmosphere was replaced with hydrogen atmosphere, and the mixture was stirred under 50 psi hydrogen pressure at 60° C. for 12 hr. The catalyst was removed by filtration, and the filtrate was concentrated under reduced pressure. The residue was purified by HPLC (column: Xbridge BEH C18, mobile phase: water/acetonitrile (containing aqueous ammonia)) to give the title compound (1.00 g).

MS: $[M+H]^+$463.2.

K) tert-butyl 4-{[(7S*,8S*)-2-methyl-7-{[(2S)-oxolane-2-carbonyl]amino}-5,6,7,8-tetrahydroimidazo[1,2-a]pyridin-8-yl]methoxy}piperidine-1-carboxylate with longer retention time tert-Butyl 4-{[(7SR,8SR)-2-methyl-7-{[(2S)-oxolane-2-carbonyl]amino}-5,6,7,8-tetrahydroimidazo[1,2-a]pyridin-8-yl]methoxy}piperidine-1-carboxylate (160 mg) was dissolved in $CH_3CN$ (10 ml), and the solution was concentrated under reduced pressure. The residue was resolved by SFC ((column: CHIRALPAK IC, 30 mmID×250 mmL, manufactured by Daicel Chemical Industries, mobile phase: carbon dioxide/EtOH (containing aqueous ammonia)) to give the title compound with longer retention time (32.0 mg).

MS: $[M+H]^+$463.2.

L) (2S)—N-[(7S*,8S*)-8-({[1-(5-fluoropyrimidin-2-yl)piperidin-4-yl]oxy}methyl)-2-methyl-5,6,7,8-tetrahydroimidazo[1,2-a]pyridin-7-yl]oxolane-2-carboxamide derived from tert-butyl 4-{[(7S*,8S*)-2-methyl-7-{[(2S)-oxolane-2-carbonyl]amino}-5,6,7,8-tetrahydroimidazo[1,2-a]pyridin-8-yl]methoxy}piperidine-1-carboxylate with longer retention time To a mixture of tert-butyl 4-{[(7S*,8S*)-2-methyl-7-{[(2S)-oxolane-2-carbonyl]amino}-5,6,7,8-tetrahydroimidazo[1,2-a]pyridin-8-yl]methoxy}piperidine-1-carboxylate with longer retention time (32.0 mg) and ethyl acetate (1 ml) was added 4 M hydrogen chloride/ethyl acetate solution (1 ml). The mixture was stirred at 25° C. for 1 hr, and concentrated under reduced pressure. A mixture of the obtained residue (28.0 mg), 2-chloro-5-fluoropyrimidine (10.2 mg), DIPEA (9.98 mg) and $CH_3CN$ (5 ml) was stirred at 90° C. 10 hr. To the reaction solution was added water, and the mixture was extracted with ethyl acetate. The organic layer was separated, dried over anhydrous sodium sulfate, and concentrated under reduced pressure. The residue was purified by HPLC (column: Xbridge BEH C18, mobile phase: water/acetonitrile (containing aqueous ammonia)) to give the title compound (9.54 mg).

¹H NMR (400 MHz, CDCl₃) δ 1.54-1.62 (2H, m), 1.78-1.95 (5H, m), 1.96-2.06 (1H, m), 2.19 (3H, s), 2.23-2.37 (1H, m), 2.45-2.56 (1H, m), 3.03-3.12 (1H, m), 3.36-3.50 (2H, m), 3.54-3.65 (1H, m), 3.71-3.85 (2H, m), 3.86-4.12 (5H, m), 4.18-4.33 (3H, m), 6.52 (1H, s), 7.18-7.25 (1H, m), 8.16 (2H, s)

The compounds of Examples are shown in the following tables. MS in the tables means actual measured value. The compounds of Examples 2 to 21, 23, 25 to 32, 34 to 55 and 57 to 62 in the following tables were produced according to the methods described in the above-mentioned Examples, or methods analogous thereto.

TABLE 1-1

| Ex. No. | IUPAC Name | Structure | Additive | MS |
|---|---|---|---|---|
| 1 | rac-N-[(6S,7R)-2-methyl-7-({[(1s,4S)-4-phenylcyclohexyl]oxy}methyl)-4,5,6,7-tetrahydropyrazolo[1,5-a]pyridin-6-yl]methanesulfonamide | 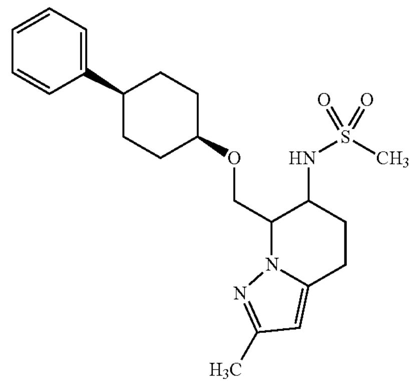 [SMILES: Cc1cc2n(n1)C(CO[C@H]1CC[C@@H](c3ccccc3)CC1)C(NS(C)(=O)=O)CC2] | | 418.1 |
| 2 | rac-N-[(6S,7R)-2-ethyl-7-({[(1s,4S)-4-phenylcyclohexyl]oxy}methyl)-4,5,6,7-tetrahydropyrazolo[1,5-a]pyridin-6-yl]methanesulfonamide | 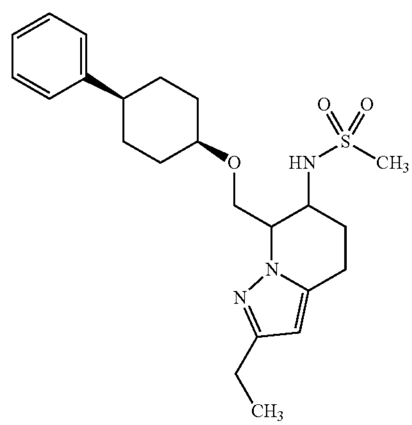 [SMILES: CCc1cc2n(n1)C(CO[C@H]1CC[C@@H](c3ccccc3)CC1)C(NS(C)(=O)=O)CC2] | | 432.1 |
| 3 | rac-N-[(6S,7R)-2-methyl-7-({[1-(pyrimidin-2-yl)piperidin-4-yl]oxy}methyl)-4,5,6,7-tetrahydropyrazolo[1,5-a]pyridin-6-yl]methanesulfonamide | 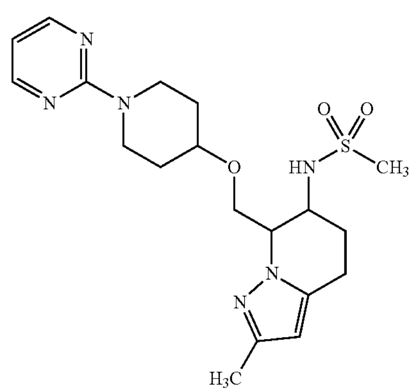 [SMILES: Cc1cc2n(n1)C(COC1CCN(c3ncccn3)CC1)C(NS(C)(=O)=O)CC2] | | 421.0 |

TABLE 1-1-continued

| Ex. No. | IUPAC Name | Structure | Additive | MS |
|---|---|---|---|---|
| 4 | rac-N-[(6S,7R)-7-({[1-(5-fluoropyrimidin-2-yl)piperidin-4-yl]oxy}methyl)-2-methyl-4,5,6,7-tetrahydropyrazolo[1,5-a]pyridin-6-yl]methanesulfonamide | 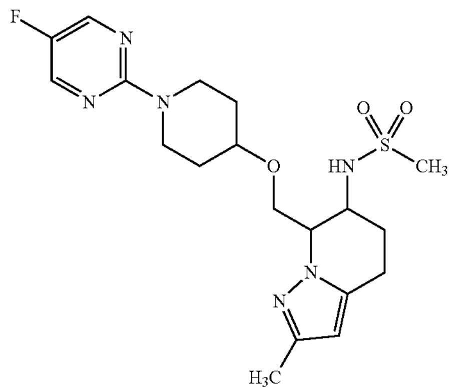 [SMILES: Cc1cc2n(n1)C(COC1CCN(c3ncc(F)cn3)CC1)C(NS(C)(=O)=O)CC2] | | 439.0 |
| 5 | rac-N-[(5R,6S)-2-methyl-5-({[(1s,4S)-4-phenylcyclohexyl]oxy}methyl)-5,6,7,8-tetrahydro[1,2,4]triazolo[1,5-a]pyridin-6-yl]methanesulfonamide | 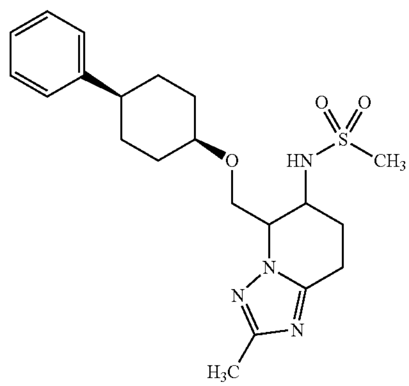 [SMILES: Cc1nc2n(n1)C(CO[C@H]1CC[C@@H](c3ccccc3)CC1)C(NS(C)(=O)=O)CC2] | | 419.3 |
| 6 | rac-N-[(5R,6S)-5-({[(1s,4S)-4-phenylcyclohexyl]oxy}methyl)-5,6,7,8-tetrahydro[1,2,4]triazolo[1,5-a]pyridin-6-yl]methanesulfonamide | 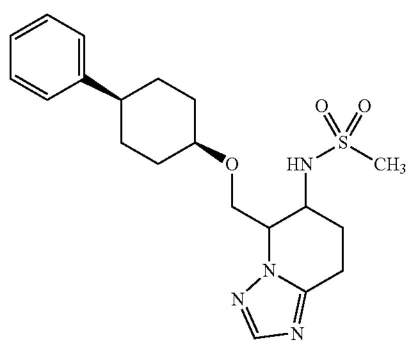 [SMILES: CS(=O)(=O)NC1CCc2ncnn2C1CO[C@H]1CC[C@@H](c2ccccc2)CC1] | | 405.2 |
| 7 | rac-N-{(6S,7S)-7-[([1,1'-biphenyl]-3-yl)methyl]-2-methyl-4,5,6,7-tetrahydropyrazolo[1,5-a]pyridin-6-yl}methanesulfonamide | 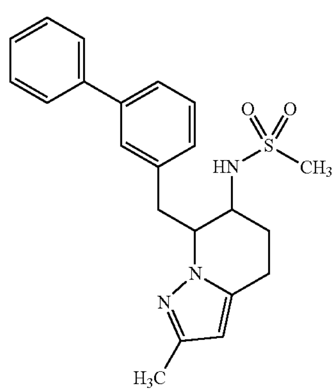 [SMILES: Cc1cc2n(n1)C(Cc1cccc(-c3ccccc3)c1)C(NS(C)(=O)=O)CC2] | | 396.3 |

TABLE 1-1-continued

| Ex. No. | IUPAC Name | Structure | Additive | MS |
|---|---|---|---|---|
| 8 | rac-N-{(6S,7S)-7-[([1,1'-biphenyl]-3-yl)methyl]-2-ethyl-4,5,6,7-tetrahydropyrazolo[1,5-a]pyridin-6-yl}methanesulfonamide | 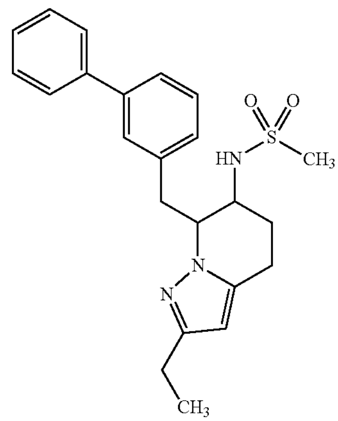 [SMILES: CCc1cc2n(n1)C(Cc1cccc(-c3ccccc3)c1)C(NS(C)(=O)=O)CC2] | | 410.3 |
| 9 | rac-N-[(6S,7R)-7-({[1-(5-fluoropyrimidin-2-yl)piperidin-4-yl]oxy}methyl)-4,5,6,7-tetrahydropyrazolo[1,5-a]pyridin-6-yl]methanesulfonamide | 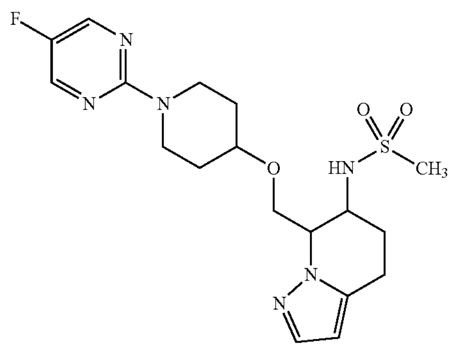 [SMILES: CS(=O)(=O)NC1CCc2ccnn2C1COC1CCN(c2ncc(F)cn2)CC1] | | 425.2 |
| 10 | rac-N-[(6S,7R)-7-({[1-(5-fluoropyrimidin-2-yl)piperidin-4-yl]oxy}methyl)-3-methyl-4,5,6,7-tetrahydro[1,2,3]triazolo[1,5-a]pyridin-6-yl]methanesulfonamide | 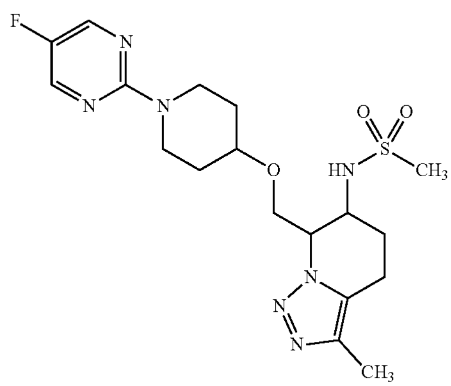 [SMILES: Cc1cnn2c1CCC(NS(C)(=O)=O)C2COC1CCN(c2ncc(F)cn2)CC1] | | 440.2 |
| 11 | rac-N-[(6S,7R)-7-({[1-(5-fluoropyrimidin-2-yl)piperidin-4-yl]oxy}methyl)-3-methyl-4,5,6,7-tetrahydropyrazolo[1,5-a]pyridin-6-yl]methanesulfonamide | 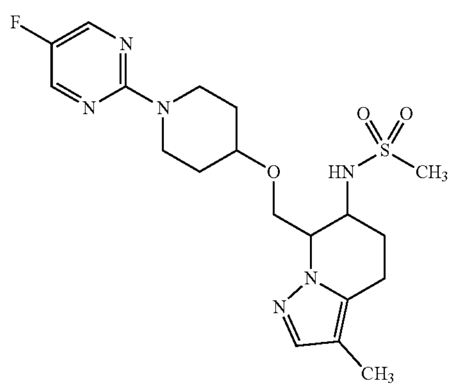 | | 439.3 |

TABLE 1-1-continued

| Ex. No. | IUPAC Name | Structure | Additive | MS |
|---|---|---|---|---|
| 12 | rac-N-[(6S,7R)-7-({[1-(5-fluoropyrimidin-2-yl)piperidin-4-yl]oxy}methyl)-2,3-dimethyl-4,5,6,7-tetrahydropyrazolo[1,5-a]pyridin-6-yl]methanesulfonamide | 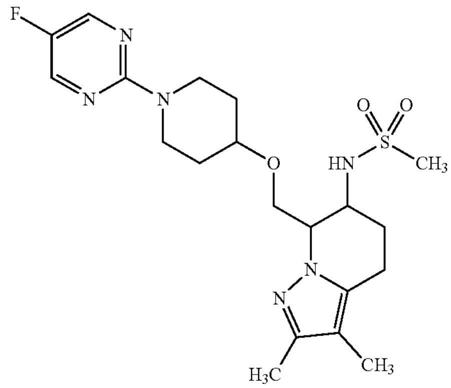 | | 453.0 |
| 13 | rac-N-{(6S,7S)-7-[(2'-fluoro[1,1'-biphenyl]-3-yl)methyl]-2-methyl-4,5,6,7-tetrahydropyrazolo[1,5-a]pyridin-6-yl}methanesulfonamide | 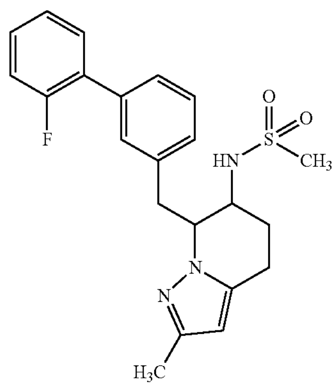 [SMILES: Cc1cc2n(n1)C(Cc1cccc(-c3ccccc3F)c1)C(NS(C)(=O)=O)CC2] | | 414.2 |
| 14 | rac-N-{(6S,7S)-7-[(3'-fluoro[1,1'-biphenyl]-3-yl)methyl]-2-methyl-4,5,6,7-tetrahydropyrazolo[1,5-a]pyridin-6-yl}methanesulfonamide | 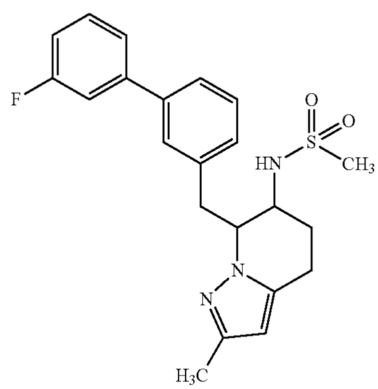 [SMILES: Cc1cc2n(n1)C(Cc1cccc(-c3cccc(F)c3)c1)C(NS(C)(=O)=O)CC2] | | 414.2 |
| 15 | rac-N-[(6S,7R)-3-chloro-7-({[1-(5-fluoropyrimidin-2-yl)piperidin-4-yl]oxy}methyl)-2-methyl-4,5,6,7-tetrahydropyrazolo[1,5-a]pyridin-6-yl]methanesulfonamide | 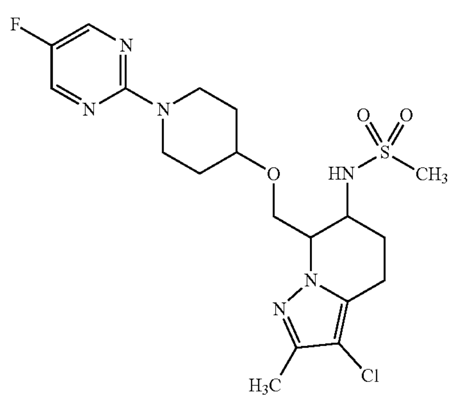 [SMILES: Cc1nn2c(c1Cl)CCC(NS(C)(=O)=O)C2COC1CCN(c2ncc(F)cn2)CC1] | | 472.9 |

TABLE 1-1-continued

| Ex. No. | IUPAC Name | Structure | Additive | MS |
|---|---|---|---|---|
| 16 | rac-N-[(6S,7S)-7-[([1,1'-biphenyl]-3-yl)methyl]-2-(propan-2-yl)-4,5,6,7-tetrahydro-2H-indazol-6-yl]methanesulfonamide | 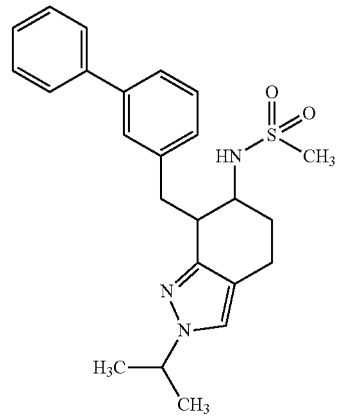 [SMILES: CC(C)n1cc2c(n1)C(Cc1cccc(-c3ccccc3)c1)C(NS(C)(=O)=O)CC2] | | 424.2 |
| 17 | rac-N-{(4S,5S)-4-[([1,1'-biphenyl]-3-yl)methyl]-2-methyl-4,5,6,7-tetrahydro-1,3-benzothiazol-5-yl}methanesulfonamide | 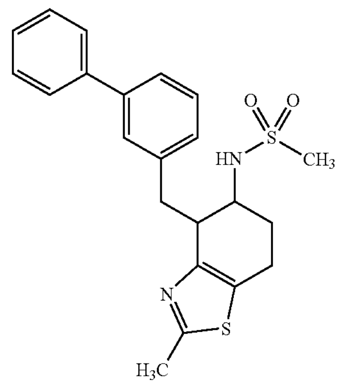 [SMILES: Cc1nc2c(s1)CCC(NS(C)(=O)=O)C2Cc1cccc(-c2ccccc2)c1] | | 413.2 |
| 18 | rac-N-[(6S,7S)-2-methyl-7-{[3-(pyridin-2-yl)phenyl]methyl}-4,5,6,7-tetrahydropyrazolo[1,5-a]pyridin-6-yl]methanesulfonamide | 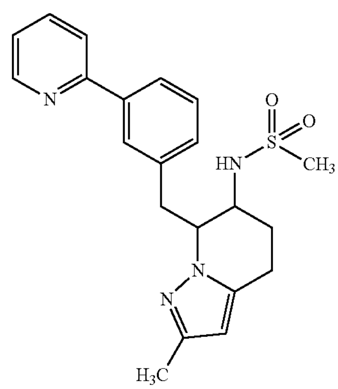 [SMILES: Cc1cc2n(n1)C(Cc1cccc(-c3ccccn3)c1)C(NS(C)(=O)=O)CC2] | | 397.2 |
| 19 | rac-N-[(6S,7S)-2-methyl-7-{[3-(6-methylpyridin-2-yl)phenyl]methyl}-4,5,6,7-tetrahydropyrazolo[1,5-a]pyridin-6-yl]methanesulfonamide | 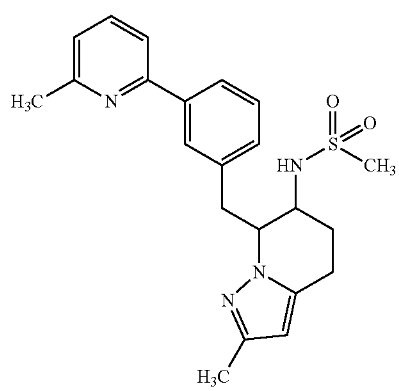 [SMILES: Cc1cccc(-c2cccc(CC3C(NS(C)(=O)=O)CCc4cc(C)nn43)c2)n1] | | 411.2 |

TABLE 1-1-continued

| Ex. No. | IUPAC Name | Structure | Additive | MS |
|---|---|---|---|---|
| 20 | rac-N-{(6S,7S)-7-[([1,1'-biphenyl]-3-yl)methyl]-2-ethyl-4,5,6,7-tetrahydro-2H-indazol-6-yl}methanesulfonamide | 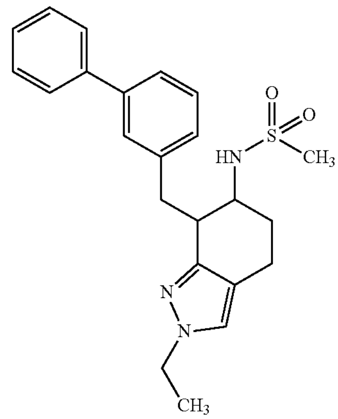 [SMILES: CCn1cc2c(n1)C(Cc1cccc(-c3ccccc3)c1)C(NS(C)(=O)=O)CC2] | | 410.2 |
| 21 | rac-N-{(6S,7S)-7-[([1,1'-biphenyl]-3-yl)methyl]-2-methyl-4,5,6,7-tetrahydro-2H-indazol-6-yl}methanesulfonamide | 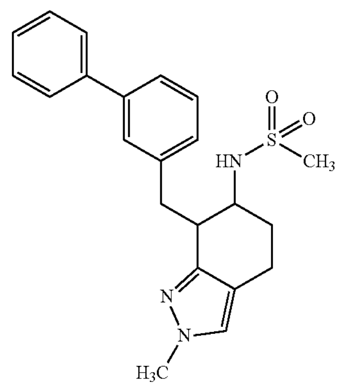 [SMILES: Cn1cc2c(n1)C(Cc1cccc(-c3ccccc3)c1)C(NS(C)(=O)=O)CC2] | | 396.3 |
| 22 | rac-N-{(7S,8S)-8-[([1,1'-biphenyl]-3-yl)methyl]-5,6,7,8-tetrahydroquinolin-7-yl}methanesulfonamide | 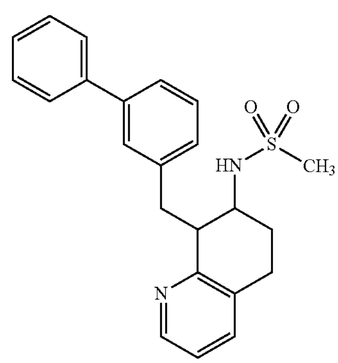 [SMILES: CS(=O)(=O)NC1CCc2cccnc2C1Cc1cccc(-c2ccccc2)c1] | | 393.3 |
| 23 | rac-N-[(6S,7S)-7-[([1,1'-biphenyl]-3-yl)methyl]-2-(propan-2-yl)-4,5,6,7-tetrahydropyrazolo[1,5-a]pyridin-6-yl]methanesulfonamide | 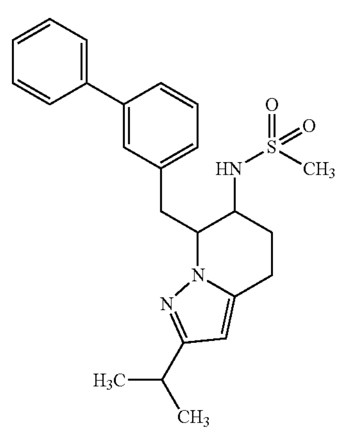 [SMILES: CC(C)c1cc2n(n1)C(Cc1cccc(-c3ccccc3)c1)C(NS(C)(=O)=O)CC2] | | 424.3 |

TABLE 1-1-continued

| Ex. No. | IUPAC Name | Structure | Additive | MS |
|---|---|---|---|---|
| 24 | rel-N-[(6S,7R)-7-({[1-(5-fluoropyrimidin-2-yl)piperidin-4-yl]oxy}methyl)-2-(propan-2-yl)-4,5,6,7-tetrahydropyrazolo[1,5-a]pyridin-6-yl]methanesulfonamide with shorter retention time | 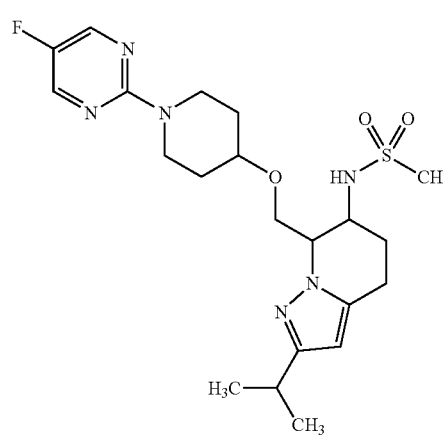 | | 467.2 |
| 25 | rel-N-[(6S,7R)-7-({[1-(5-fluoropyrimidin-2-yl)piperidin-4-yl]oxy}methyl)-2-(propan-2-yl)-4,5,6,7-tetrahydropyrazolo[1,5-a]pyridin-6-yl]methanesulfonamide with longer retention time obtained by SFC (column: CHIRALPAK OJ-H, mobile phase: carbon dioxide/0.1% aqueous ammonia in MeOH) | 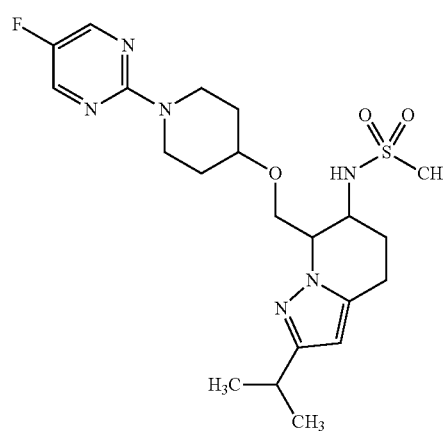 | | 467.2 |
| 26 | rac-N-[(6S,7S)-7-{[6-(3-fluorophenyl)pyridin-2-yl]methyl}-2-(propan-2-yl)-4,5,6,7-tetrahydropyrazolo[1,5-a]pyridin-6-yl]methanesulfonamide | 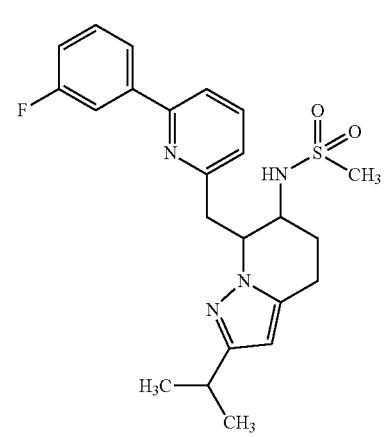 [SMILES: CC(C)c1cc2n(n1)C(Cc1cccc(-c3cccc(F)c3)n1)C(NS(C)(=O)=O)CC2] | CF3COOH | 443.2 |

TABLE 1-1-continued

| Ex. No. | IUPAC Name | Structure | Additive | MS |
|---|---|---|---|---|
| 27 | rac-N-[(6S,7S)-7-{[6-(3,5-difluorophenyl)pyridin-2-yl]methyl}-2-(propan-2-yl)-4,5,6,7-tetrahydropyrazolo[1,5-a]pyridin-6-yl]methanesulfonamide | 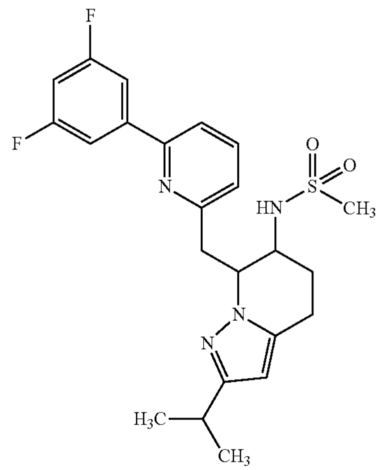 [SMILES: CC(C)c1cc2n(n1)C(Cc1cccc(-c3cc(F)cc(F)c3)n1)C(NS(C)(=O)=O)CC2] | CF3COOH | 461.2 |
| 28 | rac-N-[(6S,7R)-2-ethyl-7-({[1-(pyrimidin-2-yl)piperidin-4-yl]oxy}methyl)-4,5,6,7-tetrahydropyrazolo[1,5-a]pyridin-6-yl]methanesulfonamide | 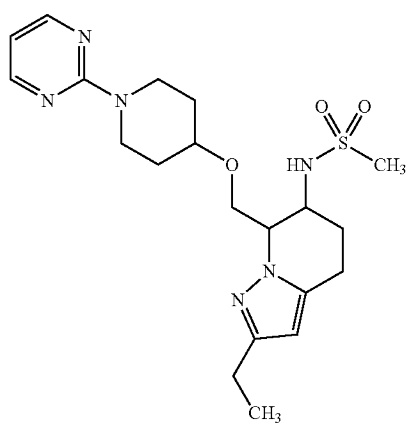 | | 435.3 |
| 29 | rac-N-[(6S,7R)-7-({[1-(2-fluorophenyl)piperidin-4-yl]oxy}methyl)-2-(propan-2-yl)-4,5,6,7-tetrahydropyrazolo[1,5-a]pyridin-6-yl]methanesulfonamide | 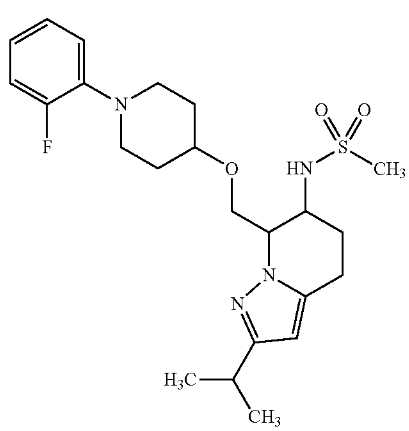 [SMILES: CC(C)c1cc2n(n1)C(COC1CCN(c3ccccc3F)CC1)C(NS(C)(=O)=O)CC2] | | 465.2 |

TABLE 1-1-continued

| Ex. No. | IUPAC Name | Structure | Additive | MS |
|---|---|---|---|---|
| 30 | rac-N-[(6S,7S)-7-[([1,1-biphenyl]-3-yl)methyl]-2-(2-hydroxypropan-2-yl)-4,5,6,7-tetrahydropyrazolo[1,5-a]pyridin-6-yl]methanesulfonamide | 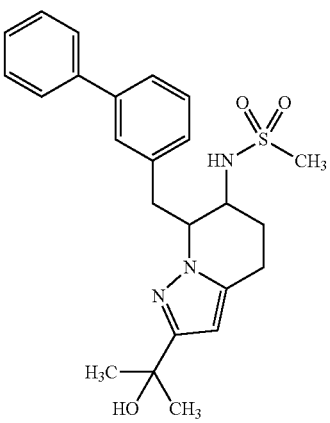 [SMILES: CC(C)(O)c1cc2n(n1)C(Cc1cccc(-c3ccccc3)c1)C(NS(C)(=O)=O)CC2] | | 440.2 |
| 31 | rel-N-[(6S,7R)-2-ethyl-7-({[1-(5-fluoropyrimidin-2-yl)piperidin-4-yl]oxy}methyl)-4,5,6,7-tetrahydropyrazolo[1,5-a]pyridin-6-yl]methanesulfonamide with shorter retention time obtained by SFC (column: CHIRALPAK AD-H, mobile phase: carbon dioxide/0.1% aqueous ammonia in MeOH) | 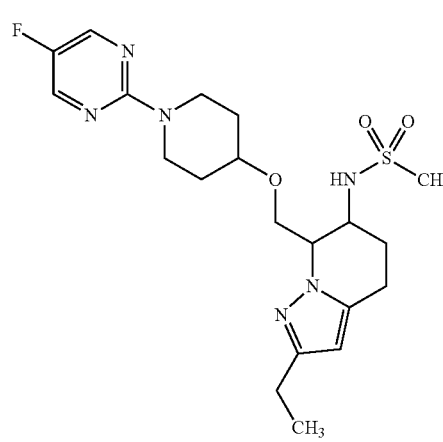 | | 453.3 |
| 32 | rac-N-[(6S,7R)-3-chloro-2-ethyl-7-({[1-(pyrimidin-2-yl)piperidin-4-yl]oxy}methyl)-4,5,6,7-tetrahydropyrazolo[1,5-a]pyridin-6-yl]methanesulfonamide | 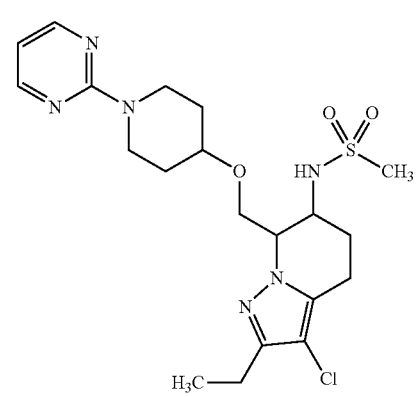 [SMILES: CCc1nn2c(c1Cl)CCC(NS(C)(=O)=O)C2COC1CCN(c2ncccn2)CC1] | | 469.2 |

TABLE 1-1-continued

| Ex. No. | IUPAC Name | Structure | Additive | MS |
|---|---|---|---|---|
| 33 | rel-N-[(6S,7R)-2-ethyl-7-({[1-(5-fluoropyrimidin-2-yl)piperidin-4-yl]oxy}methyl)-4,5,6,7-tetrahydropyrazolo[1,5-a]pyridin-6-yl]methanesulfonamide with longer retention time | 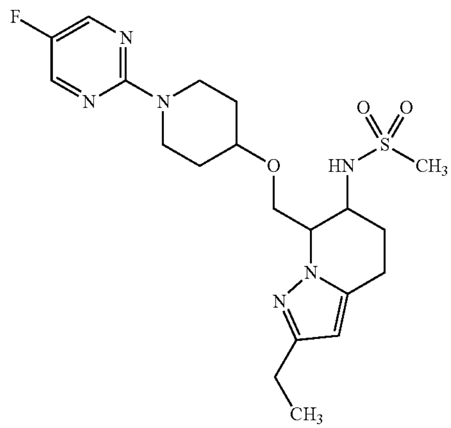 [SMILES: CCc1cc2n(n1)C(COC1CCN(c3ncc(F)cn3)CC1)C(NS(C)(=O)=O)CC2] | | 453.2 |
| 34 | rac-N-[(6S,7S)-7-[([1,1'-biphenyl]-3-yl)methyl]-2-(hydroxymethyl)-4,5,6,7-tetrahydropyrazolo[1,5-a]pyridin-6-yl]methanesulfonamide | 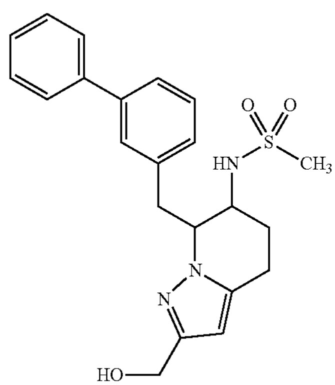 [SMILES: CS(=O)(=O)NC1CCc2cc(CO)nn2C1Cc1cccc(-c2ccccc2)c1] | | 412.3 |
| 35 | rac-(6S,7S)-7-[([1,1'-biphenyl]-3-yl)methyl]-6-[(methanesulfonyl)amino]-N,N-dimethyl-4,5,6,7-tetrahydropyrazolo[1,5-a]pyridine-2-carboxamide | 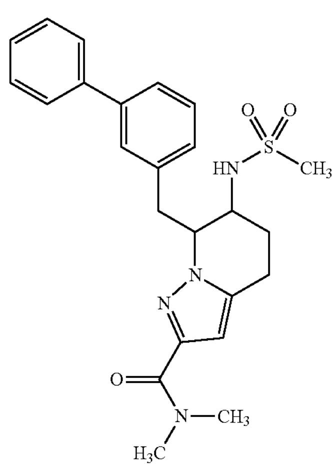 [SMILES: CN(C)C(=O)c1cc2n(n1)C(Cc1cccc(-c3ccccc3)c1)C(NS(C)(=O)=O)CC2] | | 453.3 |

TABLE 1-1-continued

| Ex. No. | IUPAC Name | Structure | Additive | MS |
|---|---|---|---|---|
| 36 | N-[(6SR,7SR)-7-[([1,1'-biphenyl]-3-yl)methyl]-2-(1-hydroxyethyl)-4,5,6,7-tetrahydropyrazolo[1,5-a]pyridin-6-yl]methanesulfonamide with shorter retention time obtained by HPLC (column: Xtimate C18, mobile phase: acetonitrile/0.05% aqueous ammonia) | 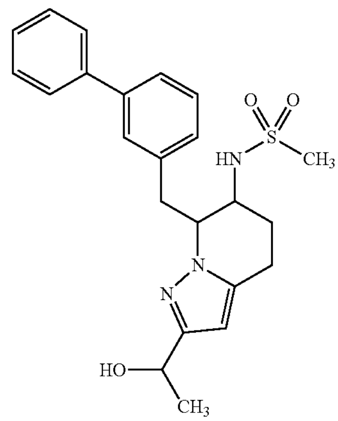 [SMILES: CC(O)c1cc2n(n1)C(Cc1cccc(-c3ccccc3)c1)C(NS(C)(=O)=O)CC2] | | 426.3 |
| 37 | rac-N-{(6S,7S)-7-[([1,1'-biphenyl]-3-yl)methyl]-2-cyano-4,5,6,7-tetrahydropyrazolo[1,5-a]pyridin-6-yl}methanesulfonamide | 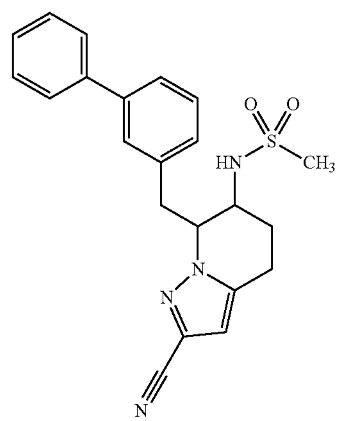 [SMILES: CS(=O)(=O)NC1CCc2cc(C#N)nn2C1Cc1cccc(-c2ccccc2)c1] | | 407.2 |
| 38 | N-[(6SR,7SR)-7-[([1,1'-biphenyl]-3-yl)methyl]-2-(1-hydroxyethyl)-4,5,6,7-tetrahydropyrazolo[1,5-a]pyridin-6-yl]methanesulfonamide with longer retention time obtained by HPLC (column: Xtimate C18, mobile phase: acetonitrile/0.05% aqueous ammonia) | 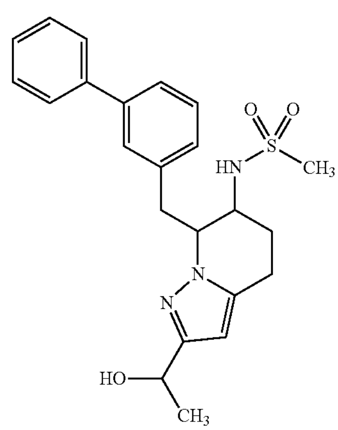 [SMILES: CC(O)c1cc2n(n1)C(Cc1cccc(-c3ccccc3)c1)C(NS(C)(=O)=O)CC2] | | 426.3 |

TABLE 1-1-continued

| Ex. No. | IUPAC Name | Structure | Additive | MS |
|---|---|---|---|---|
| 39 | rac-N-[(6S,7R)-2-ethyl-7-({[1-(5-methoxypyrimidin-2-yl)piperidin-4-yl]oxy}methyl)-4,5,6,7-tetrahydropyrazolo[1,5-a]pyridin-6-yl]methanesulfonamide | 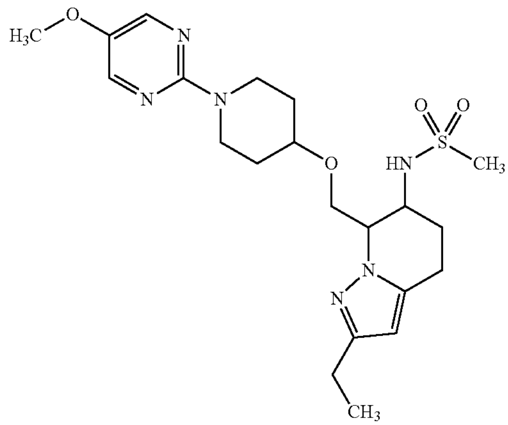 | | 465.3 |
| 40 | rac-N-[(6S,7R)-2-ethyl-7-({[1-(5-fluoro-4-methoxypyrimidin-2-yl)piperidin-4-yl]oxy}methyl)-4,5,6,7-tetrahydropyrazolo[1,5-a]pyridin-6-yl]methanesulfonamide | 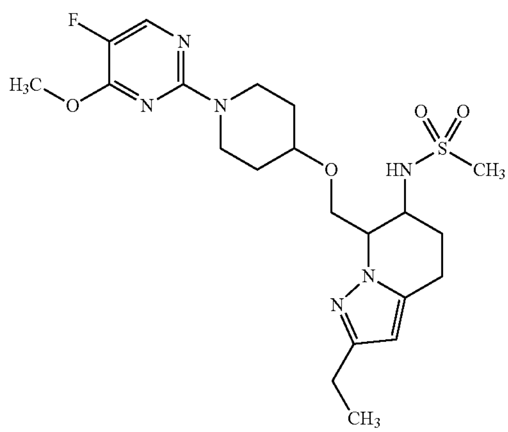 | | 483.2 |
| 41 | rac-N-[(6S,7R)-2-ethyl-7-({[1-(5-fluoro-4-methylpyrimidin-2-yl)piperidin-4-yl]oxy}methyl)-4,5,6,7-tetrahydropyrazolo[1,5-a]pyridin-6-yl]methanesulfonamide | 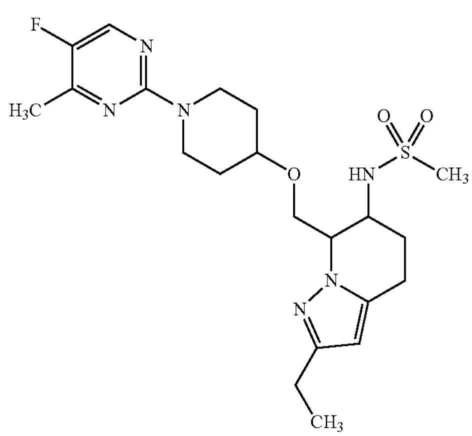 [SMILES: CCc1cc2n(n1)C(COC1CCN(c3ncc(F)c(C)n3)CC1)C(NS(C)(=O)=O)CC2] | | 467.2 |

TABLE 1-1-continued

| Ex. No. | IUPAC Name | Structure | Additive | MS |
|---|---|---|---|---|
| 42 | rac-N-[(6S,7R)-2-ethyl-7-({[1-(pyridin-2-yl)piperidin-4-yl]oxy}methyl)-4,5,6,7-tetrahydropyrazolo[1,5-a]pyridin-6-yl]methanesulfonamide | 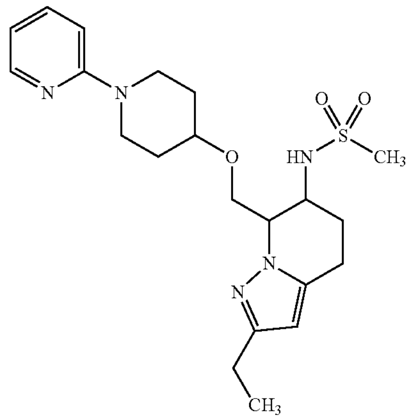 | | 434.2 |
| 43 | rac-N-[(6S,7R)-2-ethyl-7-({[1-(quinazolin-2-yl)piperidin-4-yl]oxy}methyl)-4,5,6,7-tetrahydropyrazolo[1,5-a]pyridin-6-yl]methanesulfonamide | 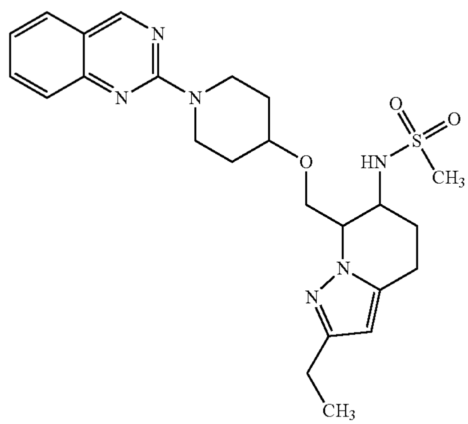 [SMILES: CCc1cc2n(n1)C(COC1CCN(c3ncc4ccccc4n3)CC1)C(NS(C)(=O)=O)CC2] | | 485.3 |
| 44 | rac-N-[(6S,7S)-7-({[1-(5-fluoropyrimidin-2-yl)piperidin-4-yl]oxy}methyl)-2-(propan-2-yl)-4,5,6,7-tetrahydro-2H-indazol-6-yl]methanesulfonamide | 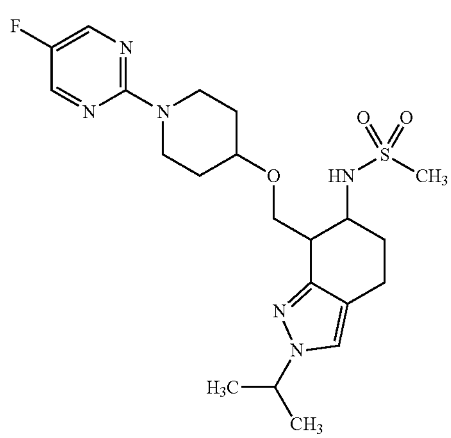 [SMILES: CC(C)n1cc2c(n1)C(COC1CCN(c3ncc(F)cn3)CC1)C(NS(C)(=O)=O)CC2] | | 467.2 |

TABLE 1-1-continued

| Ex. No. | IUPAC Name | Structure | Additive | MS |
|---|---|---|---|---|
| 45 | rac-N-[(6S,7R)-2-ethyl-7-({[1-(pyrimidin-2-yl)piperidin-4-yl]oxy}methyl)-4,5,6,7-tetrahydropyrazolo[1,5-a]pyridin-6-yl]ethanesulfonamide | 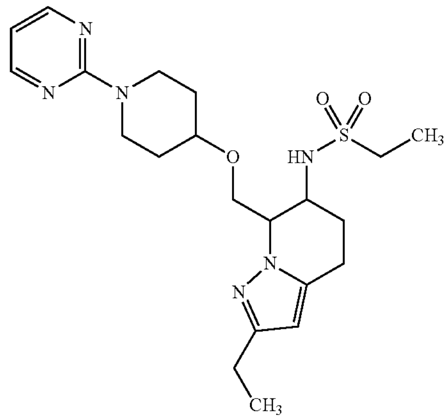 [SMILES: CCc1cc2n(n1)C(COC1CCN(c3ncccn3)CC1)C(NS(=O)(=O)CC)CC2] | | 449.3 |
| 46 | rac-N-[(6S,7R)-2-ethyl-7-{[(1-phenylpiperidin-4-yl)oxy]methyl}-4,5,6,7-tetrahydropyrazolo[1,5-a]pyridin-6-yl]methanesulfonamide | 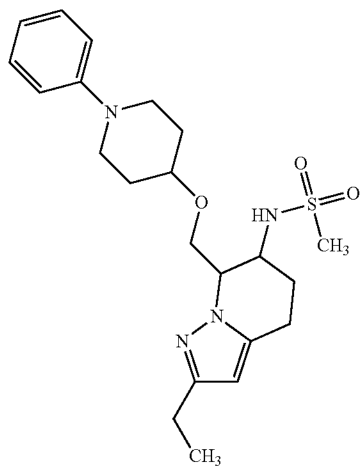 [SMILES: CCc1cc2n(n1)C(COC1CCN(c3ccccc3)CC1)C(NS(C)(=O)=O)CC2] | | 433.3 |
| 47 | rac-N-[(6S,7S)-2-(propan-2-yl)-7-({[1-(pyrimidin-2-yl)piperidin-4-yl]oxy}methyl)-4,5,6,7-tetrahydro-2H-indazol-6-yl]methanesulfonamide | 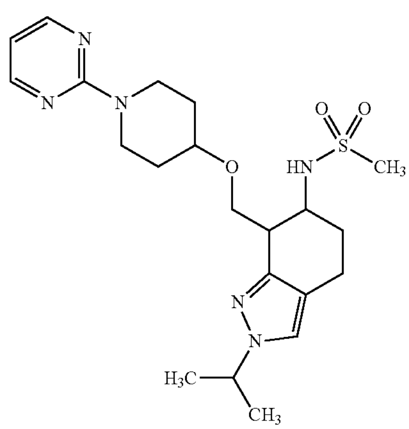 [SMILES: CC(C)n1cc2c(n1)C(COC1CCN(c3ncccn3)CC1)C(NS(C)(=O)=O)CC2] | | 449.3 |

TABLE 1-1-continued

| Ex. No. | IUPAC Name | Structure | Additive | MS |
|---|---|---|---|---|
| 48 | N-[(6SR,7RS)-2-(1-hydroxyethyl)-7-({[1-(pyrimidin-2-yl)piperidin-4-yl]oxy}methyl)-4,5,6,7-tetrahydropyrazolo[1,5-a]pyridin-6-yl]methanesulfonamide | 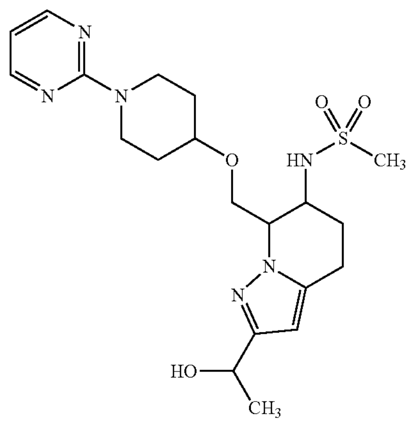 | | 451.3 |
| 49 | rac-N-[(5R,6S)-2-(propan-2-yl)-5-({[1-(pyrimidin-2-yl)piperidin-4-yl]oxy}methyl)-5,6,7,8-tetrahydro[1,2,4]triazolo[1,5-a]pyridin-6-yl]methanesulfonamide | 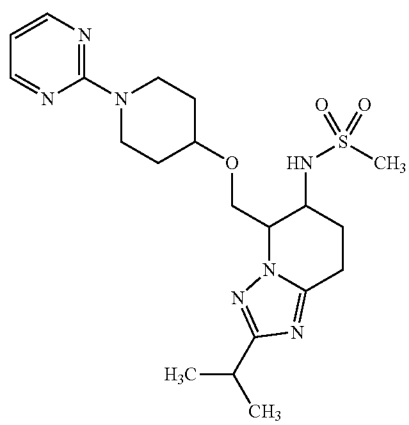 [SMILES: CC(C)c1nc2n(n1)C(COC1CCN(c3ncccn3)CC1)C(NS(C)(=O)=O)CC2] | | 450.3 |
| 50 | N-[(6SR,7RS)-3-chloro-2-(1-hydroxyethyl)-7-({[1-(pyrimidin-2-yl)piperidin-4-yl]oxy}methyl)-4,5,6,7-tetrahydropyrazolo[1,5-a]pyridin-6-yl]methanesulfonamide | 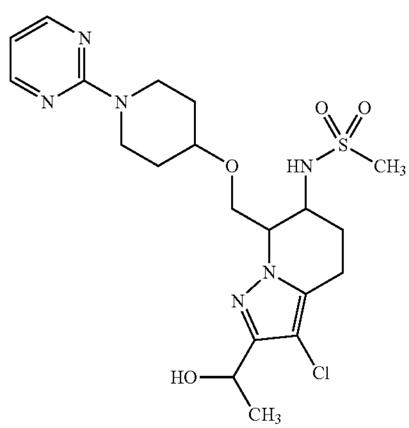 [SMILES: CC(O)c1nn2c(c1Cl)CCC(NS(C)(=O)=O)C2COC1CCN(c2ncccn2)CC1] | | 485.2 |

TABLE 1-1-continued

| Ex. No. | IUPAC Name | Structure | Additive | MS |
|---|---|---|---|---|
| 51 | rac-N-[(6S,7R)-2-(2-hydroxypropan-2-yl)-7-({[1-(pyrimidin-2-yl)piperidin-4-yl]oxy}methyl)-4,5,6,7-tetrahydropyrazolo[1,5-a]pyridin-6-yl]methanesulfonamide | 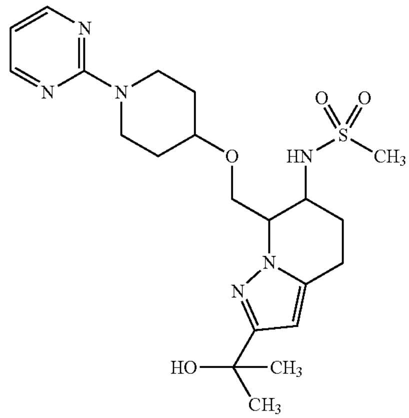 [SMILES: CC(C)(O)c1cc2n(n1)C(COC1CCN(c3ncccn3)CC1)C(NS(C)(=O)=O)CC2] | | 465.2 |
| 52 | rac-N-[(6S,7R)-3-bromo-2-ethyl-7-({[1-(5-fluoropyrimidin-2-yl)piperidin-4-yl]oxy}methyl)-4,5,6,7-tetrahydropyrazolo[1,5-a]pyridin-6-yl]methanesulfonamide | 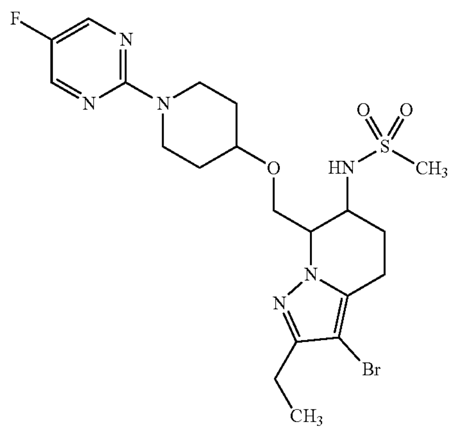 [SMILES: CCc1nn2c(c1Br)CCC(NS(C)(=O)=O)C2COC1CCN(c2ncc(F)cn2)CC1] | | 531.1 |
| 53 | rac-N-[(6S,7R)-3-chloro-2-(2-hydroxypropan-2-yl)-7-({[1-(pyrimidin-2-yl)piperidin-4-yl]oxy}methyl)-4,5,6,7-tetrahydropyrazolo[1,5-a]pyridin-6-yl]methanesulfonamide | 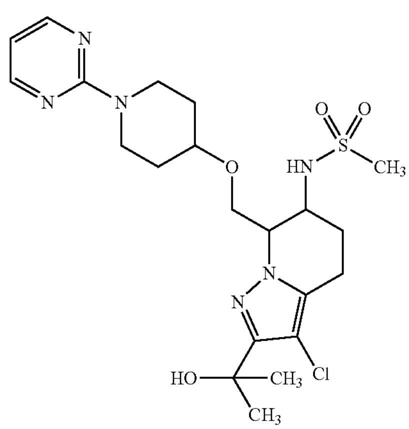 [SMILES: CC(C)(O)c1nn2c(c1Cl)CCC(NS(C)(=O)=O)C2COC1CCN(c2ncccn2)CC1] | | 499.2 |

TABLE 1-1-continued

| Ex. No. | IUPAC Name | Structure | Additive | MS |
|---|---|---|---|---|
| 54 | rac-N-[(5R,6S)-2-ethyl-5-({[1-(pyrimidin-2-yl)piperidin-4-yl]oxy}methyl)-5,6,7,8-tetrahydro[1,2,4]triazolo[1,5-a]pyridin-6-yl]methanesulfonamide | 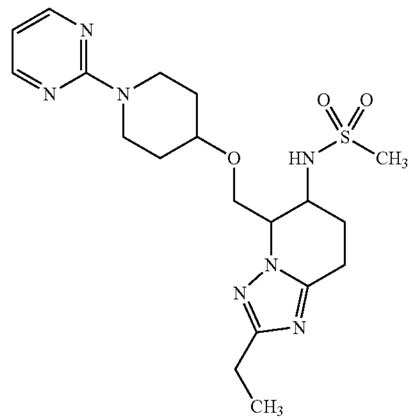 [SMILES: CCc1nc2n(n1)C(COC1CCN(c3ncccn3)CC1)C(NS(C)(=O)=O)CC2] | | 436.3 |
| 55 | rel-N⁻1⁻,N⁻1⁻-dimethyl-N⁻2⁻-{(7S,8S)-2-methyl-8-[(3'-methyl[1,1'-biphenyl]-3-yl)methyl]-5,6,7,8-tetrahydroimidazo[1,2-a]pyridin-7-yl}ethanediamide with shorter retention time obtained by SFC (column: CHIRALPAK AD, mobile phase: carbon dioxide/0.1% aqueous ammonia in EtOH) | 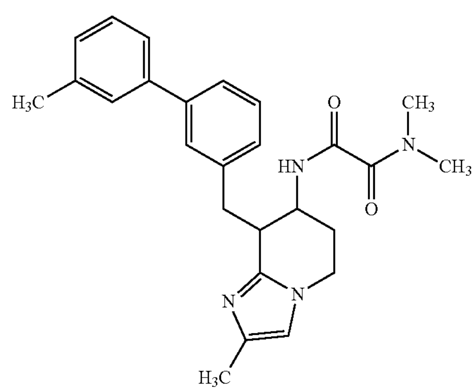 | | 431.3 |
| 56 | rel-N-[(6S,7R)-2-(propan-2-yl)-7-({[1-(pyrimidin-2-yl)piperidin-4-yl]oxy}methyl)-4,5,6,7-tetrahydropyrazolo[1,5-a]pyridin-6-yl]methanesulfonamide with longer retention time | 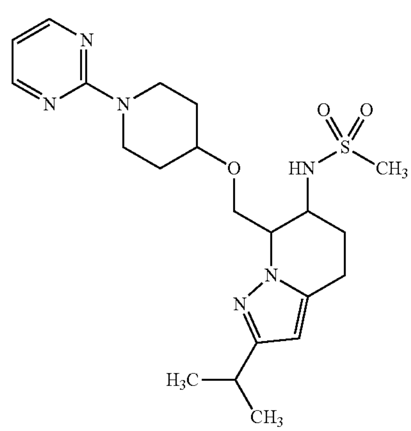 [SMILES: CC(C)c1cc2n(n1)C(COC1CCN(c3ncccn3)CC1)C(NS(C)(=O)=O)CC2] | | 449.3 |

TABLE 1-1-continued

| Ex. No. | IUPAC Name | Structure | Additive | MS |
|---|---|---|---|---|
| 57 | rel-N-{(7S,8S)-8-[(3'-fluoro[1,1'-biphenyl]-3-yl)methyl]-2-methyl-5,6,7,8-tetrahydroimidazo[1,2-a]pyridin-7-yl}methanesulfonamide with shorter retention time obtained by SFC (column: CHIRALPAK AD, mobile phase: carbon dioxide/0.1% aqueous ammonia in EtOH) | 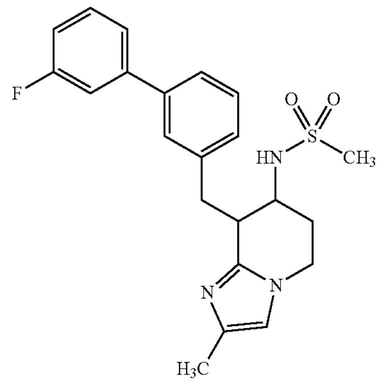 [SMILES: Cc1cn2c(n1)C(Cc1cccc(-c3cccc(F)c3)c1)C(NS(C)(=O)=O)CC2] | | 414.3 |
| 58 | rel-N-{(7S,8S)-8-[(3'-fluoro[1,1'-biphenyl]-3-yl)methyl]-2-methyl-5,6,7,8-tetrahydroimidazo[1,2-a]pyridin-7-yl}ethanesulfonamide with shorter retention time obtained by SFC (column: CHIRALPAK AD, mobile phase: carbon dioxide/0.1% aqueous ammonia in EtOH) | 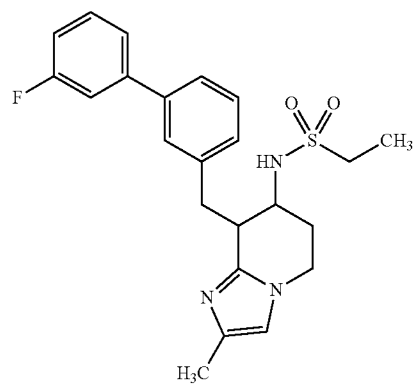 [SMILES: CCS(=O)(=O)NC1CCn2cc(C)nc2C1Cc1cccc(-c2cccc(F)c2)c1] | | 428.2 |
| 59 | rel-N-[(6S,7R)-2-ethyl-7-({[1-(pyrimidin-2-yl)piperidin-4-yl]oxy}methyl)-4,5,6,7-tetrahydropyrazolo[1,5-a]pyridin-6-yl]methanesulfonamide with shorter retention time obtained by HPLC (column: Chiralcel OD, mobile phase: hexane/EtOH/diethylamine) | 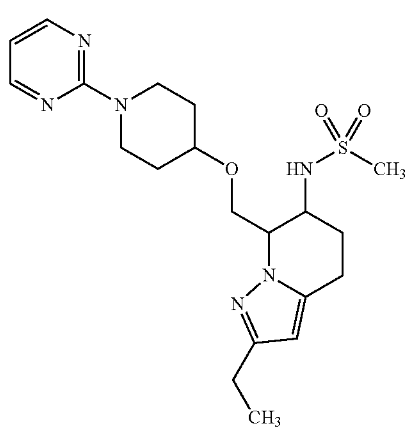 [SMILES: CCc1cc2n(n1)C(COC1CCN(c3ncccn3)CC1)C(NS(C)(=O)=O)CC2] | | 435.3 |

TABLE 1-1-continued

| Ex. No. | IUPAC Name | Structure | Additive | MS |
|---|---|---|---|---|
| 60 | rel-N-[(6S,7R)-2-ethyl-7-({[1-(pyrimidin-2-yl)piperidin-4-yl]oxy}methyl)-4,5,6,7-tetrahydropyrazolo[1,5-a]pyridin-6-yl]methanesulfonamide with longer retention time obtained by HPLC (column: Chiralcel OD, mobile phase: hexane/EtOH/diethylamine) | 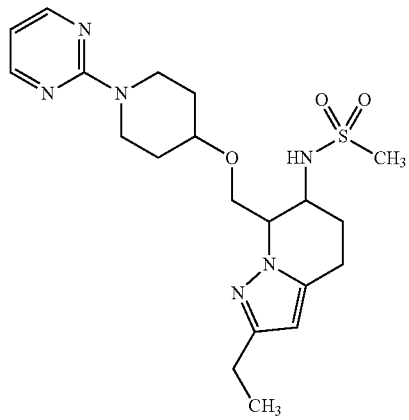 [SMILES: CCc1cc2n(n1)C(COC1CCN(c3ncccn3)CC1)C(NS(C)(=O)=O)CC2] | | 435.3 |
| 61 | rel-N-[(6S,7R)-2-(propan-2-yl)-7-({[1-(pyrimidin-2-yl)piperidin-4-yl]oxy}methyl)-4,5,6,7-tetrahydropyrazolo[1,5-a]pyridin-6-yl]methanesulfonamide with shorter retention time obtained by HPLC (column: CHIRALPAK ID, mobile phase: hexane/EtOH/diethylamine) | 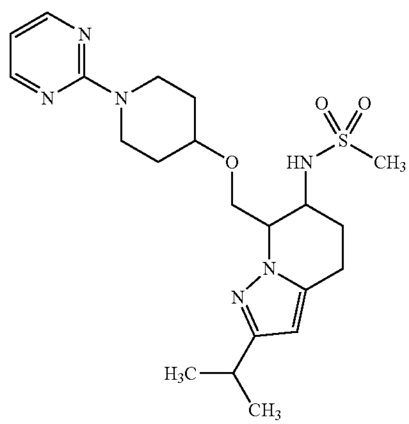 [SMILES: CC(C)c1cc2n(n1)C(COC1CCN(c3ncccn3)CC1)C(NS(C)(=O)=O)CC2] | | 449.3 |
| 62 | rac-N-{(7S,8S)-8-[([1,1'-biphenyl]-3-yl)methyl]-2-methyl-5,6,7,8-tetrahydroquinolin-7-yl}methanesulfonamide | 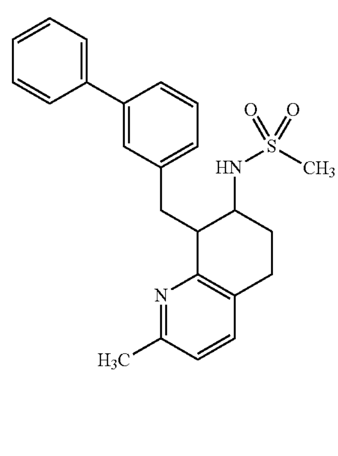 [SMILES: Cc1ccc2c(n1)C(Cc1cccc(-c3ccccc3)c1)C(NS(C)(=O)=O)CC2] | | 407.3 |

TABLE 1-1-continued

| Ex. No. | IUPAC Name | Structure | Additive | MS |
|---|---|---|---|---|
| 63 | (2S)-N-[(7S*,8S*)-8-({[1-(5-fluoropyrimidin-2-yl)piperidin-4-yl]oxy}methyl)-2-methyl-5,6,7,8-tetrahydroimidazo[1,2-a]pyridin-7-yl]oxolane-2-carboxamide, which was derived from tert-butyl 4-{[(7S*,8S*)-2-methyl-7-{[(2S)-oxolane-2-carbonyl]amino}-5,6,7,8-tetrahydroimidazo[1,2-a]pyridin-8-yl]methoxy}piperidine-1-carboxylate with longer retention time obtained by SFC (column: CHIRALPAK IC-3, mobile phase: carbon dioxide/0.05% diethylamine in EtOH) | 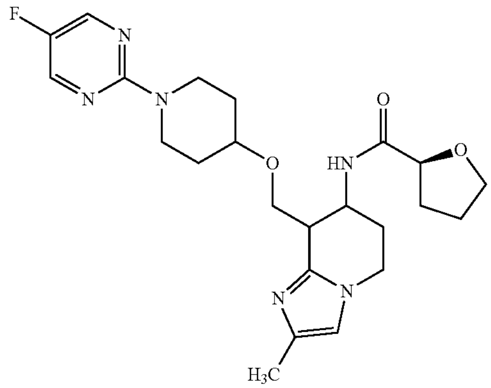 [SMILES: Cc1cn2c(n1)C(COC1CCN(c3ncc(F)cn3)CC1)C(NC(=O)[C@@H]1CCCO1)CC2] | | 459.3 |

Experimental Example 1

Obtainment of Cell Stably Expressing Human Orexin Type 2 Receptor (hOX2R)

To obtain a cell clone stably expressing human orexin type 2 receptor, human orexin type 2 receptor cDNA was inserted into pcDNA3.1(+) plasmid vector (Invitrogen), and a plasmid DNA for expression of human orexin type 2 receptor (pcDNA3.1(+)/hOX2R) was cloned. The plasmid DNA was introduced into CHO-dhfr cell by an electroporation method, and human orexin type 2 receptor expressing clone cells were obtained by limiting dilution method by using G418 drug resistance as a selection marker.

Experimental Example 2

Measurement of Orexin Type 2 Receptor Agonist Activity

CHO cells forcibly expressing human OX2 receptor were seeded in each well of 384 well black transparent bottom plate (BD Falcon) at 7,500 cells/well, and cultured for one day in a 5% $CO_2$ incubator at 37° C. After removal of the medium in the cell plate, assay buffer A containing a calcium indicator (HBSS (Thermo Fisher Scientific), 20 mM HEPES (Thermo Fisher Scientific), 0.1% BSA (Sigma-Aldrich), 2.5 μg/mL Fluo-4 AM (DOJINDO Chemical), 0.08% Pluronic F127 (DOJINDO Chemical), 1.25 mM probenecid (DOJINDO Chemical)) was added at 30 μL/well. The plate was stood for 30 min in a 5% $CO_2$ incubator at 37° C., and further stood at room temperature for 30 min. A test compound prepared by diluting with assay buffer B (HBSS, 20 mM HEPES, 0.1% BSA) was added at 10 μL/well, and the fluorescence value was measured by FDSSpCELL (Hamamatsu Photonics K. K.) every one sec for 1 min, and thereafter every two sec for 1 min 40 sec. The activity (%) of the test compound was calculated assuming that variation in the fluorescence value when DMSO was added instead of the test compound was 0%, and variation in the fluorescence value when orexin A (human) (PEPTIDE INSTITUTE, INC.) was added at the final concentration of 10 nM was 100%. The activity of each compound at the concentration of 3 μM was shown in Table 2. As is clear from the results, the compound of the present invention was shown to have an agonist activity on human orexin type 2 receptor.

TABLE 2

| Example No. | OX2R agonist activity (3 μM, %) |
|---|---|
| 1 | 104 |
| 2 | 107 |
| 3 | 82 |
| 4 | 98 |
| 5 | 99 |
| 6 | 85 |
| 7 | 77 |
| 8 | 92 |
| 9 | 85 |
| 10 | 69 |
| 12 | 102 |
| 15 | 91 |
| 16 | 84 |
| 17 | 62 |
| 22 | 63 |
| 23 | 109 |
| 24 | 111 |
| 28 | 102 |
| 29 | 80 |
| 32 | 92 |
| 33 | 91 |
| 36 | 105 |
| 40 | 96 |
| 41 | 80 |
| 42 | 80 |
| 44 | 94 |
| 45 | 101 |
| 47 | 98 |
| 50 | 92 |
| 52 | 95 |
| 56 | 100 |
| 57 | 94 |
| 58 | 95 |
| 59 | 101 |
| 62 | 72 |
| 63 | 92 |

Formulation Example 1 (Production of Capsule)

| | |
|---|---|
| 1) compound of Example 1 | 30 mg |
| 2) crystalline cellulose | 10 mg |

-continued

| 3) lactose | 19 mg |
|---|---|
| 4) magnesium stearate | 1 mg |
| total | 60 mg |

1), 2), 3) and 4) are mixed and filled in a gelatin capsule.

Formulation Example 2 (Production of Tablet)

| 1) compound of Example 1 | 30 g |
|---|---|
| 2) lactose | 50 g |
| 3) cornstarch | 15 g |
| 4) calcium carboxymethylcellulose | 44 g |
| 5) magnesium stearate | 1 g |
| 1000 tablets | 140 g in total |

The total amount of 1), 2), 3) and 30 g of 4) are kneaded with water, vacuum dried and sieved. The sieved powder is mixed with 14 g of 4) and 1 g of 5), and the mixture is punched by a tableting machine. In this way, 1000 tablets containing 30 mg of the compound of Example 1 per tablet are obtained.

INDUSTRIAL APPLICABILITY

The compound of the present invention has an orexin type 2 receptor agonist activity, and is useful as an agent for the prophylaxis or treatment of narcolepsy.

This application is based on patent application No. 2018-232993 filed on Dec. 12, 2018 in Japan, the contents of which are encompassed in full herein.

The invention claimed is:

1. A compound represented by the formula:

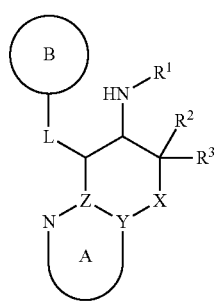

(I)

wherein $R^1$ is an optionally substituted $C_{1-6}$ alkylsulfonyl group, an optionally substituted mono- or di-$C_{1-6}$ alkylaminosulfonyl group, an optionally substituted 3- to 6-membered cyclylsulfonyl group, a formylcarbonyl group, a carboxycarbonyl group, a carbamoylcarbonyl group, an optionally substituted $C_{1-6}$ alkyl-carbonyl group, an optionally substituted $C_{1-6}$ alkoxy-carbonyl group, an optionally substituted mono- or di-$C_{1-6}$ alkyl-carbamoyl group, an optionally substituted $C_{1-6}$ alkyl-carbonyl-carbonyl group, an optionally substituted $C_{1-6}$ alkoxy-carbonyl-carbonyl group, an optionally substituted mono- or di-$C_{1-6}$ alkyl-carbamoyl-carbonyl group or an optionally substituted 3- to 6-membered cyclylcarbonyl group;

$R^2$ and $R^3$ are each independently a hydrogen atom, an optionally substituted $C_{1-6}$ alkyl group or a halogen atom;

X is an optionally substituted methylene group or an oxygen atom;

Y and Z are each independently a carbon atom or a nitrogen atom;

Ring A is an optionally substituted 5- or 6-membered nitrogen-containing aromatic heterocycle;

L is an optionally substituted methylene group, an oxygen atom, —O-$L^1$-, -$L^1$-O— or -$L^1$-$L^2$-;

$L^1$ and $L^2$ are each independently an optionally substituted methylene group; and Ring B is an optionally further substituted 4- to 7-membered ring, or a salt thereof.

2. The compound or salt according to claim 1, wherein $R^1$ is, (1) a $C_{1-6}$ alkylsulfonyl group, (2) a mono- or di-$C_{1-6}$ alkyl-carbamoyl-carbonyl group, or (3) a 3- to 6-membered non-aromatic heterocyclylcarbonyl group;

$R^2$ and $R^3$ are both hydrogen atoms;

X is a methylene group;

Y and Z are each independently a carbon atom or a nitrogen atom;

Ring A is a 5- or 6-membered aromatic heterocycle optionally substituted by 1 to 3 substituents selected from (a) a halogen atom, (b) a cyano group, (c) a $C_{1-6}$ alkyl group optionally substituted by 1 to 3 hydroxy groups, and (d) a mono- or di-$C_{1-6}$ alkyl-carbamoyl group;

L is a methylene group or —O—$CH_2$—; and

Ring B is a 6-membered ring further substituted by 1 to 3 substituents selected from (a) a $C_{6-14}$ aryl group optionally substituted by 1 to 3 substituents selected from (i) a halogen atom, and (ii) a $C_{1-6}$ alkyl group, and (b) a 5- or 6-membered monocyclic aromatic heterocyclic group or a 8- to 14-membered fused polycyclic aromatic heterocyclic group, each optionally substituted 1 to 3 substituents selected from (i) a halogen atom, (ii) a $C_{1-6}$ alkyl group, and (iii) a $C_{1-6}$ alkoxy group.

3. The compound or salt according to claim 1, wherein $R^1$ is, (1) a $C_{1-6}$ alkylsulfonyl group, (2) a mono- or di-$C_{1-6}$ alkyl-carbamoyl-carbonyl group, or (3) a tetrahydrofurylcarbonyl group;

$R^2$ and $R^3$ are both hydrogen atoms;

X is a methylene group;

Y and Z are each independently a carbon atom or a nitrogen atom;

Ring A is (1) a pyrazole ring optionally substituted by 1 to 3 substituents selected from (a) a halogen atom, (b) a cyano group, (c) a $C_{1-6}$ alkyl group optionally substituted by 1 to 3 hydroxy groups, and (d) a mono- or di-$C_{1-6}$ alkyl-carbamoyl group, (2) a triazole ring optionally substituted by 1 to 3 $C_{1-6}$ alkyl groups, (3) an imidazole ring optionally substituted by 1 to 3 $C_{1-6}$ alkyl groups, (4) a thiazole ring optionally substituted by 1 to 3 $C_{1-6}$ alkyl groups, or (5) a pyridine ring optionally substituted by 1 to 3 $C_{1-6}$ alkyl groups;

L is a methylene group or —O—$CH_2$—; and

Ring B is (1) a cyclohexane ring further substituted by 1 to 3 $C_{6-14}$ aryl groups, (2) a piperidine ring further substituted by 1 to 3 substituents selected from (a) a $C_{6-14}$ aryl group optionally substituted by 1 to 3 halogen atoms, and (b) a pyridyl group, a pyrimidinyl group or a quinazolinyl group, each optionally substituted 1 to 3 substituents selected from (i) a halogen atom, (ii) a $C_{1-6}$ alkyl group, and (iii) a $C_{1-6}$ alkoxy group, (3) a benzene ring further substituted by 1 to 3 substituents selected from (a) a $C_{6-14}$ aryl group optionally substituted by 1 to 3 substituents selected from (i) a halogen atom, and (ii) a $C_{1-6}$ alkyl group, and (b) a pyridyl group optionally substituted by 1 to 3 $C_{1-6}$ alkyl groups, or (4) a pyridine ring further substituted by 1 to 3 $C_{6-14}$ aryl groups optionally substituted by 1 to 3 halogen atoms.

4. The compound or salt according to claim 1, wherein $R^1$ is a $C_{1-6}$ alkylsulfonyl group;

$R^2$ and $R^3$ are both hydrogen atoms;

X is a methylene group;

Y and Z are each independently a carbon atom or a nitrogen atom;

Ring A is a pyrazole ring optionally substituted by 1 to 3 $C_{1-6}$ alkyl groups;

L is —O—$CH_2$—; and

Ring B is a piperidine ring further substituted by 1 to 3 pyrimidinyl groups optionally substituted by 1 to 3 halogen atoms.

5. The compound of claim 1, which is N-[7-({[1-(5-Fluoropyrimidin-2-yl) piperidin-4-yl]oxy}methyl)-2-(propan-2-yl)-4,5,6,7-tetrahydropyrazolo[1,5-a]pyridin-6-yl]methanesulfonamide or a salt thereof.

6. The compound of claim 1, which is N-[2-Ethyl-7-({[1-(5-fluoropyrimidin-2-yl) piperidin-4-yl]oxy}methyl)-4,5,6,7-tetrahydropyrazolo[1,5-a]pyridin-6-yl]methanesulfonamide or a salt thereof.

7. The compound of claim 1, which is N-[2-(Propan-2-yl)-7-({[1-(pyrimidin-2-yl) piperidin-4-yl]oxy}methyl)-4,5,6,7-tetrahydropyrazolo[1,5-a]pyridin-6-yl]methanesulfonamide or a salt thereof.

8. A medicament comprising the compound or salt according to claim 1.

9. The medicament according to claim 8, which is an orexin type 2 receptor agonist.

10. The medicament according to claim 8, which is an agent for the prophylaxis or treatment of narcolepsy.

11. The compound or salt according to claim 1 for use in the prophylaxis or treatment of narcolepsy.

12. A method for activating an orexin type 2 receptor in a mammal, which comprises administering an effective amount of the compound or salt according to claim 1 to the mammal.

13. A method for treating narcolepsy in a mammal, which comprises administering an effective amount of the compound or salt according to claim 1 to the mammal.

* * * * *